(12) United States Patent
Denison et al.

(10) Patent No.: US 12,397,156 B2
(45) Date of Patent: Aug. 26, 2025

(54) DEVICES, SYSTEMS, AND METHODS FOR INCONTINENCE CONTROL

(71) Applicant: Amber Therapeutics Ltd, London (GB)

(72) Inventors: Timothy Denison, Oxford (GB); Stefan De Wachter, Antwerp (BE); Charles Knowles, London (GB); Aidan Crawley, London (GB)

(73) Assignee: Amber Therapeutics Holdings Limited, London (GB)

( * ) Notice: Subject to any disclaimer, the term of this patent is extended or adjusted under 35 U.S.C. 154(b) by 0 days.

(21) Appl. No.: 18/734,326

(22) Filed: Jun. 5, 2024

(65) Prior Publication Data

US 2024/0424296 A1 Dec. 26, 2024

Related U.S. Application Data

(63) Continuation of application No. 18/213,225, filed on Jun. 22, 2023, now Pat. No. 12,064,625, which is a continuation of application No. 18/068,020, filed on Dec. 19, 2022, now Pat. No. 12,059,564, which is a continuation of application No. 17/692,611, filed on Mar. 11, 2022, now Pat. No. 11,565,109.

(Continued)

(51) Int. Cl.
*A61N 1/36* (2006.01)
*A61N 1/05* (2006.01)

(52) U.S. Cl.
CPC ....... *A61N 1/36007* (2013.01); *A61N 1/0551* (2013.01); *A61N 1/36139* (2013.01)

(58) Field of Classification Search
CPC .................................................. A61N 1/36007
USPC ........................................................... 607/41
See application file for complete search history.

(56) References Cited

U.S. PATENT DOCUMENTS

| 3,942,535 A | 3/1976 | Schulman |
| 5,733,313 A | 3/1998 | Barreras et al. |

(Continued)

FOREIGN PATENT DOCUMENTS

| AU | 2019204642 A1 | 7/2019 |
| CA | 3160396 A1 | 6/2021 |

(Continued)

OTHER PUBLICATIONS

Fischell, R. E., et al., "A Long-Lived, Reliable, Rechargeable Cardiac Pacemaker", Engineering in Medicine, vol. 1, 1975, 34 pages.

(Continued)

*Primary Examiner* — Nadia A Mahmood
(74) *Attorney, Agent, or Firm* — Knobbe, Martens, Olson & Bear, LLP

(57) ABSTRACT

Provided are devices and methods for preventing an episode of incontinence in an individual in need thereof. The devices comprise a sensor and a stimulator electrode that can be implanted into the body of the individual. Once the device is implanted in the individual, the sensor of the device senses a parameter that is associated with a response from the individual that is intended to prevent an episode of incontinence. Then, the device provides an electrical stimulation using the electrode that, together with the response, helps to prevent the episode of incontinence.

90 Claims, 18 Drawing Sheets

Related U.S. Application Data

(60) Provisional application No. 63/160,322, filed on Mar. 12, 2021.

(56) References Cited

U.S. PATENT DOCUMENTS

| | | | |
|---|---|---|---|
| 6,055,456 A | 4/2000 | Gerber | |
| 7,295,881 B2 | 11/2007 | Cohen et al. | |
| 7,328,068 B2 | 2/2008 | Spinelli et al. | |
| 7,415,308 B2 | 8/2008 | Gerber et al. | |
| 7,522,061 B2 | 4/2009 | Rondoni et al. | |
| 7,647,112 B2 | 1/2010 | Tracey et al. | |
| 7,684,873 B2 | 3/2010 | Gerber | |
| 7,686,760 B2 | 3/2010 | Anderson et al. | |
| 7,702,385 B2 | 4/2010 | Moffitt et al. | |
| 7,729,772 B2 | 6/2010 | Williams et al. | |
| 7,774,069 B2 | 8/2010 | Olson et al. | |
| 7,855,653 B2 | 12/2010 | Rondoni et al. | |
| 7,891,085 B1 | 2/2011 | Kuzma et al. | |
| 7,894,913 B2 | 2/2011 | Boggs et al. | |
| 7,912,555 B2 | 3/2011 | Swoyer et al. | |
| 7,974,703 B2 | 7/2011 | Goetz et al. | |
| 7,996,092 B2 | 8/2011 | Mrva et al. | |
| 8,019,423 B2 | 9/2011 | Possover | |
| 8,036,756 B2 | 10/2011 | Swoyer et al. | |
| 8,068,910 B2 | 11/2011 | Gerber et al. | |
| 8,072,338 B2 | 12/2011 | Rondoni et al. | |
| 8,121,691 B2 | 2/2012 | Gerber et al. | |
| 8,165,695 B2 | 4/2012 | Diubaldi et al. | |
| 8,260,436 B2 | 9/2012 | Gerber et al. | |
| 8,260,439 B2 | 9/2012 | Diubaldi et al. | |
| 8,295,933 B2 | 10/2012 | Gerber et al. | |
| 8,352,026 B2 | 1/2013 | Diubaldi | |
| 8,428,735 B2 | 4/2013 | Littlewood et al. | |
| 8,435,166 B2 | 5/2013 | Burnett et al. | |
| 8,457,758 B2 | 6/2013 | Olson et al. | |
| 8,494,643 B2 | 7/2013 | Cowan et al. | |
| 8,521,292 B2 | 8/2013 | Wei et al. | |
| 8,583,256 B2 | 11/2013 | Tracey et al. | |
| 8,612,018 B2 | 12/2013 | Gillbe | |
| 8,626,314 B2 | 1/2014 | Swoyer et al. | |
| 8,630,711 B1 | 1/2014 | Wark et al. | |
| 8,639,342 B2 | 1/2014 | Possover | |
| 8,644,938 B2 | 2/2014 | Craggs | |
| 8,688,238 B2 | 4/2014 | Gerber | |
| 8,706,232 B2 | 4/2014 | Su et al. | |
| 8,706,233 B2 | 4/2014 | Su et al. | |
| 8,738,148 B2 | 5/2014 | Olson et al. | |
| 8,744,585 B2 | 6/2014 | Gerber et al. | |
| 8,751,003 B2 | 6/2014 | Diubaldi et al. | |
| 8,805,508 B2 | 8/2014 | Gerber et al. | |
| 8,825,165 B2 | 9/2014 | Possover | |
| 8,886,321 B2 | 11/2014 | Rohrer et al. | |
| 8,983,612 B2 | 3/2015 | Fang et al. | |
| 8,989,861 B2 | 3/2015 | Su et al. | |
| 9,005,102 B2 | 4/2015 | Burnett et al. | |
| 9,072,886 B2 | 7/2015 | Gaunt et al. | |
| 9,089,693 B2 | 7/2015 | Swoyer et al. | |
| 9,089,699 B2 | 7/2015 | Su et al. | |
| 9,108,025 B2 | 8/2015 | Spenser et al. | |
| 9,114,261 B2 | 8/2015 | Yonce | |
| 9,155,855 B2 | 10/2015 | Tebbutt et al. | |
| 9,155,885 B2 | 10/2015 | Wei et al. | |
| 9,168,374 B2 | 10/2015 | Su | |
| 9,173,678 B2 | 11/2015 | Siegel et al. | |
| 9,192,763 B2 | 11/2015 | Gerber et al. | |
| 9,220,895 B2 | 12/2015 | Siff et al. | |
| 9,259,587 B2 | 2/2016 | Goetz et al. | |
| 9,265,927 B2 | 2/2016 | Yonce et al. | |
| 9,272,140 B2 | 3/2016 | Gerber | |
| 9,289,607 B2 | 3/2016 | Su et al. | |
| 9,327,117 B2 | 5/2016 | Denison et al. | |
| 9,381,351 B2 | 7/2016 | Haessler | |
| 9,433,783 B2 | 9/2016 | Wei et al. | |
| 9,446,235 B2 | 9/2016 | Su et al. | |
| 9,463,324 B2 | 10/2016 | Olson et al. | |
| 9,480,840 B2 | 11/2016 | Rohrer et al. | |
| 9,498,633 B2 | 11/2016 | Laing et al. | |
| 9,555,246 B2 | 1/2017 | Jiang et al. | |
| 9,561,366 B2 | 2/2017 | Wei et al. | |
| 9,597,520 B2 | 3/2017 | Gillbe et al. | |
| 9,623,243 B2 | 4/2017 | Chancellor et al. | |
| 9,623,253 B2 | 4/2017 | Perryman et al. | |
| 9,630,004 B2 | 4/2017 | Rajguru et al. | |
| 9,707,390 B2 | 7/2017 | Ahmed | |
| 9,707,391 B2 | 7/2017 | Ahmed | |
| 9,707,396 B2 | 7/2017 | Su et al. | |
| 9,724,509 B2 | 8/2017 | Su et al. | |
| 9,724,511 B2 | 8/2017 | Wei et al. | |
| 9,737,707 B2 | 8/2017 | Haessler et al. | |
| 9,757,584 B2 | 9/2017 | Burnett | |
| 9,764,132 B2 | 9/2017 | Rohrer et al. | |
| 9,782,583 B2 | 10/2017 | Sharma | |
| 9,789,252 B2 | 10/2017 | Gerber et al. | |
| 9,821,112 B2 | 11/2017 | Olson et al. | |
| 9,855,423 B2 | 1/2018 | Jiang et al. | |
| 9,861,547 B2 | 1/2018 | Crunick et al. | |
| 9,950,159 B2 | 4/2018 | Beck et al. | |
| 9,956,404 B2 | 5/2018 | Brink et al. | |
| 9,993,639 B2 | 6/2018 | Gerber | |
| 9,999,532 B2 | 6/2018 | Mische | |
| 9,999,763 B2 | 6/2018 | Shiroff et al. | |
| 10,004,557 B2 | 6/2018 | Gross | |
| 10,016,599 B2 | 7/2018 | Lockwood et al. | |
| 10,035,020 B2 | 7/2018 | Wang et al. | |
| 10,046,164 B2 | 8/2018 | Gerber | |
| 10,076,661 B2 | 9/2018 | Wei et al. | |
| 10,086,197 B2 | 10/2018 | Lin et al. | |
| 10,143,850 B2 | 12/2018 | Cowan et al. | |
| 10,195,419 B2 | 2/2019 | Shiroff et al. | |
| 10,201,702 B2 | 2/2019 | Bonde et al. | |
| 10,213,604 B2 | 2/2019 | Dinsmoor et al. | |
| 10,220,205 B2 | 3/2019 | Bhadra et al. | |
| 10,227,713 B2 | 3/2019 | Ganatra et al. | |
| 10,232,175 B2 | 3/2019 | Possover | |
| 10,238,451 B2 | 3/2019 | Sachs et al. | |
| 10,238,877 B2 | 3/2019 | Kaula et al. | |
| 10,245,439 B1 | 4/2019 | Schwarz et al. | |
| 10,315,031 B2 | 6/2019 | Brink et al. | |
| 10,384,067 B2 | 8/2019 | Jiang et al. | |
| 10,391,313 B2 | 8/2019 | Moffitt et al. | |
| 10,471,255 B2 | 11/2019 | Imran | |
| 10,478,249 B2 | 11/2019 | Gross et al. | |
| 10,478,612 B2 | 11/2019 | Schepis et al. | |
| 10,478,619 B2 | 11/2019 | Lee et al. | |
| 10,493,270 B2 | 12/2019 | Ahmed | |
| 10,518,086 B2 | 12/2019 | Su et al. | |
| 10,525,268 B2 | 1/2020 | Torgerson | |
| 10,531,944 B2 | 1/2020 | Lamraoui | |
| 10,543,366 B2 | 1/2020 | Christopherson et al. | |
| 10,549,087 B2 | 2/2020 | Yoo et al. | |
| 10,556,104 B2 | 2/2020 | Gerber | |
| 10,561,835 B2 | 2/2020 | Gerber | |
| 10,583,284 B2 | 3/2020 | Peters et al. | |
| 10,583,298 B2 | 3/2020 | Wang et al. | |
| 10,603,502 B2 | 3/2020 | Cogan et al. | |
| 10,674,963 B2 | 6/2020 | Toth | |
| 10,744,260 B2 | 8/2020 | Gerber et al. | |
| 10,751,533 B2 | 8/2020 | Edgerton et al. | |
| 10,758,723 B2 | 9/2020 | Fang et al. | |
| 10,765,355 B2 | 9/2020 | Nelson et al. | |
| 10,828,490 B2 | 11/2020 | Sachs et al. | |
| 10,835,748 B2 | 11/2020 | Ackermann et al. | |
| 10,994,134 B2 | 5/2021 | Thor | |
| 10,994,140 B2 | 5/2021 | Yeh et al. | |
| 11,013,911 B2 | 5/2021 | Swoyer et al. | |
| 11,045,650 B2 | 6/2021 | Brink et al. | |
| 11,077,301 B2 | 8/2021 | Creasey et al. | |
| 11,103,723 B2 | 8/2021 | Deisseroth et al. | |
| 11,110,271 B1 | 9/2021 | Schobben et al. | |
| 11,116,985 B2 | 9/2021 | Jiang et al. | |
| 11,147,966 B2 | 10/2021 | Tranchina et al. | |
| 11,167,138 B2 | 11/2021 | Patel et al. | |
| 11,198,006 B1 | 12/2021 | Nijlunsing et al. | |
| 11,213,340 B2 | 1/2022 | Su et al. | |

(56) References Cited

U.S. PATENT DOCUMENTS

| | | |
|---|---|---|
| 11,224,748 B2 | 1/2022 | Dinsmoor et al. |
| 11,229,788 B1 | 1/2022 | John et al. |
| 11,285,321 B2 | 3/2022 | Ganguly et al. |
| 11,305,110 B2 | 4/2022 | Toong et al. |
| 11,318,319 B2 | 5/2022 | Schobben et al. |
| 11,324,947 B2 | 5/2022 | Kaula et al. |
| 11,406,822 B2 | 8/2022 | Hvalsøe et al. |
| 11,413,452 B2 | 8/2022 | Shepherd et al. |
| 11,420,052 B2 | 8/2022 | Doskocil et al. |
| 11,426,579 B2 | 8/2022 | John et al. |
| 11,446,490 B2 | 9/2022 | Doskocil |
| 11,529,513 B2 | 12/2022 | John et al. |
| 11,534,200 B2 | 12/2022 | Bonde et al. |
| 11,565,109 B2 | 1/2023 | Denison et al. |
| 11,571,575 B2 | 2/2023 | Su et al. |
| 11,596,792 B2 | 3/2023 | Campean et al. |
| 11,633,593 B2 | 4/2023 | John et al. |
| 11,638,814 B2 | 5/2023 | Doskocil et al. |
| 11,642,540 B2 | 5/2023 | Bornzin et al. |
| 11,672,978 B2 | 6/2023 | Su et al. |
| 11,712,557 B2 | 8/2023 | Toong et al. |
| 11,730,411 B2 | 8/2023 | Jiang et al. |
| 11,752,334 B2 | 9/2023 | Yoo et al. |
| 11,766,561 B2 | 9/2023 | Mishra et al. |
| 11,779,761 B2 | 10/2023 | Druke et al. |
| 11,794,001 B2 | 10/2023 | Imran |
| 11,794,009 B2 | 10/2023 | Tai |
| 11,826,427 B2 | 11/2023 | Garibyan et al. |
| 11,839,762 B2 | 12/2023 | Doskocil et al. |
| 11,844,943 B2 | 12/2023 | Rajguru et al. |
| 11,850,434 B2 | 12/2023 | Knudsen et al. |
| 11,896,734 B2 | 2/2024 | Williams et al. |
| 11,896,824 B2 | 2/2024 | Doskocil |
| 11,911,614 B2 | 2/2024 | Grill et al. |
| 11,918,806 B2 | 3/2024 | Wong et al. |
| 11,925,801 B2 | 3/2024 | Wei et al. |
| 11,925,802 B2 | 3/2024 | Tai |
| 11,957,894 B2 | 4/2024 | Chasensky et al. |
| 12,059,564 B2 | 8/2024 | Denison et al. |
| 12,064,625 B2 | 8/2024 | Denison et al. |
| 2002/0055761 A1 | 5/2002 | Mann et al. |
| 2003/0045919 A1 | 3/2003 | Swoyer et al. |
| 2003/0100930 A1 | 5/2003 | Cohen et al. |
| 2005/0216069 A1 | 9/2005 | Cohen et al. |
| 2006/0004421 A1 | 1/2006 | Bennett et al. |
| 2006/0020297 A1 | 1/2006 | Gerber et al. |
| 2006/0035882 A1 | 2/2006 | Koga et al. |
| 2006/0122660 A1 | 6/2006 | Boveja et al. |
| 2006/0247723 A1 | 11/2006 | Gerber et al. |
| 2007/0100387 A1 | 5/2007 | Gerber |
| 2007/0150034 A1 | 6/2007 | Rooney et al. |
| 2008/0103570 A1 | 5/2008 | Gerber |
| 2008/0300649 A1 | 12/2008 | Gerber et al. |
| 2009/0036945 A1 | 2/2009 | Chancellor et al. |
| 2009/0054950 A1 | 2/2009 | Stephens |
| 2009/0254144 A1 | 10/2009 | Bhadra et al. |
| 2010/0094372 A1 | 4/2010 | Grill et al. |
| 2012/0010680 A1 | 1/2012 | Wei et al. |
| 2012/0197336 A1 | 8/2012 | Su |
| 2013/0041430 A1 | 2/2013 | Wang et al. |
| 2013/0289664 A1 | 10/2013 | Johanek |
| 2013/0331905 A1 | 12/2013 | Haessler |
| 2014/0058474 A1 | 2/2014 | Haessler |
| 2014/0163579 A1 | 6/2014 | Tischendorf et al. |
| 2014/0309708 A1 | 10/2014 | Sharma |
| 2015/0080906 A1 | 3/2015 | Fjorback et al. |
| 2016/0045731 A1 | 2/2016 | Simon et al. |
| 2016/0263376 A1* | 9/2016 | Yoo ................... A61N 1/36017 |
| 2016/0338902 A1 | 11/2016 | St et al. |
| 2017/0001003 A1 | 1/2017 | Pivonka et al. |
| 2017/0095667 A1 | 4/2017 | Yakovlev et al. |
| 2017/0173327 A1 | 6/2017 | Wei et al. |
| 2017/0231547 A1 | 8/2017 | Imran |
| 2018/0008311 A1 | 1/2018 | Shiroff et al. |
| 2018/0078760 A1 | 3/2018 | Lee et al. |
| 2018/0214691 A1 | 8/2018 | Famm et al. |
| 2018/0289971 A1 | 10/2018 | Yeh et al. |
| 2018/0296497 A1 | 10/2018 | Schepis et al. |
| 2019/0110732 A1 | 4/2019 | Toth et al. |
| 2019/0117974 A1 | 4/2019 | Creasey et al. |
| 2019/0143102 A1 | 5/2019 | Romero-Ortega et al. |
| 2019/0247664 A1 | 8/2019 | Irazoqui et al. |
| 2019/0269924 A1 | 9/2019 | Su et al. |
| 2019/0290902 A1 | 9/2019 | Romero-Ortega et al. |
| 2019/0336763 A1 | 11/2019 | Spurling et al. |
| 2019/0374776 A1 | 12/2019 | Mishra et al. |
| 2020/0046552 A1 | 2/2020 | Velis et al. |
| 2020/0069939 A1 | 3/2020 | Imran |
| 2020/0101294 A1 | 4/2020 | Torgerson |
| 2020/0139018 A1 | 5/2020 | Martin et al. |
| 2020/0139115 A1 | 5/2020 | Verity |
| 2020/0147375 A1 | 5/2020 | Su et al. |
| 2020/0171312 A1 | 6/2020 | Dinsmoor et al. |
| 2020/0171313 A1 | 6/2020 | Dinsmoor et al. |
| 2020/0230406 A1 | 7/2020 | Brink et al. |
| 2020/0246617 A1 | 8/2020 | Errico et al. |
| 2020/0338267 A1 | 10/2020 | Gerber et al. |
| 2020/0376266 A1 | 12/2020 | Toong et al. |
| 2020/0397361 A1 | 12/2020 | Nelson et al. |
| 2021/0069513 A1 | 3/2021 | Beer et al. |
| 2021/0085962 A1 | 3/2021 | Patel |
| 2021/0101008 A1 | 4/2021 | Sandgren et al. |
| 2021/0113834 A1 | 4/2021 | Wong et al. |
| 2021/0175727 A1 | 6/2021 | Schobben et al. |
| 2021/0187291 A1 | 6/2021 | Iyer et al. |
| 2021/0268278 A1 | 9/2021 | Agahari |
| 2021/0275808 A1 | 9/2021 | Jacobson et al. |
| 2021/0299442 A1 | 9/2021 | Wei et al. |
| 2021/0315638 A1 | 10/2021 | Townley et al. |
| 2021/0330981 A1 | 10/2021 | Mishra et al. |
| 2021/0346695 A1 | 11/2021 | Grill et al. |
| 2021/0361952 A1 | 11/2021 | Bonde et al. |
| 2021/0379382 A1 | 12/2021 | John et al. |
| 2022/0022951 A1 | 1/2022 | Townley |
| 2022/0088373 A1 | 3/2022 | Burnett |
| 2022/0105348 A1 | 4/2022 | Brink et al. |
| 2022/0111211 A1 | 4/2022 | Li et al. |
| 2022/0118245 A1 | 4/2022 | Hvalsoe et al. |
| 2022/0134105 A1 | 5/2022 | Hvalsoe et al. |
| 2022/0134118 A1 | 5/2022 | Johnson |
| 2022/0143394 A1 | 5/2022 | John et al. |
| 2022/0143403 A1 | 5/2022 | Offutt et al. |
| 2022/0152402 A1 | 5/2022 | Mueller et al. |
| 2022/0176128 A1 | 6/2022 | Dinsmoor et al. |
| 2022/0193406 A1 | 6/2022 | Imran |
| 2022/0193428 A1 | 6/2022 | Martens et al. |
| 2022/0218985 A1 | 7/2022 | Schobben et al. |
| 2022/0218986 A1 | 7/2022 | Schobben et al. |
| 2022/0233848 A1 | 7/2022 | Gad et al. |
| 2022/0233860 A1 | 7/2022 | Hamner et al. |
| 2022/0241599 A1 | 8/2022 | Fischer et al. |
| 2022/0266012 A1 | 8/2022 | Hamner et al. |
| 2022/0288388 A1 | 9/2022 | Rondoni et al. |
| 2022/0288389 A1 | 9/2022 | Denison et al. |
| 2022/0323751 A1 | 10/2022 | Sharma |
| 2022/0331584 A1 | 10/2022 | Offutt et al. |
| 2022/0331586 A1 | 10/2022 | Offutt et al. |
| 2022/0331589 A1 | 10/2022 | Bittner et al. |
| 2022/0339443 A1 | 10/2022 | Schobben et al. |
| 2022/0347461 A1 | 11/2022 | Campean et al. |
| 2022/0361941 A1 | 11/2022 | Townley |
| 2022/0395686 A1 | 12/2022 | Tai |
| 2022/0401747 A1 | 12/2022 | Possover |
| 2022/0409896 A1 | 12/2022 | John et al. |
| 2023/0001185 A1 | 1/2023 | Schobben et al. |
| 2023/0021801 A1 | 1/2023 | Sridhar et al. |
| 2023/0029600 A1 | 2/2023 | Pivonka et al. |
| 2023/0042557 A1 | 2/2023 | Bennett et al. |
| 2023/0059066 A1 | 2/2023 | Sridhar et al. |
| 2023/0074492 A1 | 3/2023 | Offutt et al. |
| 2023/0079328 A1 | 3/2023 | Matton et al. |
| 2023/0083643 A1 | 3/2023 | Toong et al. |
| 2023/0103791 A1 | 4/2023 | Davis et al. |
| 2023/0113727 A1 | 4/2023 | Van et al. |

(56) References Cited

U.S. PATENT DOCUMENTS

| | | |
|---|---|---|
| 2023/0121038 A1 | 4/2023 | John et al. |
| 2023/0130942 A1 | 4/2023 | Denison et al. |
| 2023/0139116 A1 | 5/2023 | Wiygul et al. |
| 2023/0149709 A1 | 5/2023 | Romero-Ortega et al. |
| 2023/0157604 A1 | 5/2023 | Imran |
| 2023/0158306 A1 | 5/2023 | Jiang et al. |
| 2023/0166113 A1 | 6/2023 | Nesbitt et al. |
| 2023/0166116 A1 | 6/2023 | Crites-Bachert |
| 2023/0173274 A1 | 6/2023 | Lee |
| 2023/0211158 A1 | 7/2023 | Grill et al. |
| 2023/0226356 A1 | 7/2023 | Toong et al. |
| 2023/0233853 A1 | 7/2023 | Zirpel et al. |
| 2023/0256244 A1 | 8/2023 | John et al. |
| 2023/0264019 A1 | 8/2023 | Doskocil et al. |
| 2023/0271005 A1 | 8/2023 | Ostroff et al. |
| 2023/0277844 A1 | 9/2023 | Errico et al. |
| 2023/0302287 A1 | 9/2023 | Jiang et al. |
| 2023/0347145 A1 | 11/2023 | Denison et al. |
| 2023/0364413 A1 | 11/2023 | Romaniw et al. |
| 2023/0381504 A1 | 11/2023 | Yoo et al. |
| 2023/0390461 A1 | 12/2023 | Crook et al. |
| 2023/0414950 A1 | 12/2023 | Maharbiz et al. |
| 2024/0024667 A1 | 1/2024 | Coates et al. |
| 2024/0074888 A1 | 3/2024 | Bennett et al. |
| 2024/0075295 A1 | 3/2024 | Tesfayesus |
| 2024/0087736 A1 | 3/2024 | Errico et al. |
| 2024/0091538 A1 | 3/2024 | Fraga et al. |
| 2024/0123224 A1 | 4/2024 | Lysy et al. |
| 2024/0123225 A1 | 4/2024 | Paralikar et al. |
| 2024/0278022 A1 | 8/2024 | Mishra et al. |
| 2024/0359007 A1 | 10/2024 | Arora et al. |

FOREIGN PATENT DOCUMENTS

| | | |
|---|---|---|
| CN | 101460218 A | 6/2009 |
| EP | 1761303 A2 | 3/2007 |
| EP | 1940510 A2 | 7/2008 |
| EP | 1967519 A1 | 9/2008 |
| EP | 1981589 A1 | 10/2008 |
| EP | 2023819 A1 | 2/2009 |
| EP | 2155062 A1 | 2/2010 |
| EP | 2162181 A1 | 3/2010 |
| EP | 2166950 A1 | 3/2010 |
| EP | 2314585 A1 | 4/2011 |
| EP | 2389975 A1 | 11/2011 |
| EP | 2717961 A1 | 4/2014 |
| EP | 2861145 A1 | 4/2015 |
| EP | 2841008 B1 | 9/2017 |
| EP | 3212162 A2 | 9/2017 |
| EP | 3242712 A1 | 11/2017 |
| EP | 3270834 A2 | 1/2018 |
| EP | 3157620 A4 | 4/2018 |
| EP | 3310429 A1 | 4/2018 |
| EP | 3191172 A4 | 5/2018 |
| EP | 3318304 A1 | 5/2018 |
| EP | 3331601 A1 | 6/2018 |
| EP | 3253441 A4 | 8/2018 |
| EP | 3180072 B1 | 11/2018 |
| EP | 3364870 A4 | 4/2019 |
| EP | 3468657 A1 | 4/2019 |
| EP | 3481494 A1 | 5/2019 |
| EP | 3532154 A1 | 9/2019 |
| EP | 3573519 A1 | 12/2019 |
| EP | 3589248 A1 | 1/2020 |
| EP | 3319685 B1 | 8/2020 |
| EP | 3180070 B1 | 4/2021 |
| EP | 3813647 A1 | 5/2021 |
| EP | 3866913 A1 | 8/2021 |
| EP | 3762092 A4 | 12/2021 |
| EP | 3924035 A1 | 12/2021 |
| EP | 3969102 A1 | 3/2022 |
| EP | 3976169 A1 | 4/2022 |
| EP | 4021518 A1 | 7/2022 |
| EP | 4069062 A1 | 10/2022 |
| EP | 4093485 A1 | 11/2022 |
| EP | 3057652 B1 | 7/2023 |
| EP | 4240436 A1 | 9/2023 |
| EP | 3560552 B1 | 12/2023 |
| EP | 4308219 A1 | 1/2024 |
| EP | 4326391 A1 | 2/2024 |
| GB | 2414410 A | 11/2005 |
| WO | 01/83029 A1 | 11/2001 |
| WO | 2007/074916 A1 | 7/2007 |
| WO | 2007/082382 A1 | 7/2007 |
| WO | 2007/130168 A1 | 11/2007 |
| WO | 2008/147612 A1 | 12/2008 |
| WO | 2008/150590 A1 | 12/2008 |
| WO | 2008/153726 A2 | 12/2008 |
| WO | 2009/134475 A1 | 11/2009 |
| WO | 2009/137119 A1 | 11/2009 |
| WO | 2010/111321 A2 | 9/2010 |
| WO | 2011/156288 A2 | 12/2011 |
| WO | 2015/059570 A1 | 4/2015 |
| WO | 2015/196164 A2 | 12/2015 |
| WO | 2016/039768 A1 | 3/2016 |
| WO | 2016/127130 A1 | 8/2016 |
| WO | 2016/154076 A2 | 9/2016 |
| WO | 2016/203258 A1 | 12/2016 |
| WO | 2016/209997 A1 | 12/2016 |
| WO | 2017/070372 A1 | 4/2017 |
| WO | 2018/038794 A1 | 3/2018 |
| WO | 2018/053336 A1 | 3/2018 |
| WO | 2019/173084 A1 | 9/2019 |
| WO | 2019/209417 A1 | 10/2019 |
| WO | 2020/006048 A1 | 1/2020 |
| WO | 2020/033883 A1 | 2/2020 |
| WO | 2020/165591 A1 | 8/2020 |
| WO | 2020/231440 A1 | 11/2020 |
| WO | 2020/243104 A1 | 12/2020 |
| WO | 2021/042044 A1 | 3/2021 |
| WO | 2021/176219 A1 | 9/2021 |
| WO | 2022/189862 A1 | 9/2022 |
| WO | 2022/200814 A1 | 9/2022 |
| WO | 2023/161720 A1 | 8/2023 |
| WO | 2023/177650 A2 | 9/2023 |
| WO | 2023/230131 A1 | 11/2023 |
| WO | 2023/242367 A1 | 12/2023 |
| WO | 2023/250426 A1 | 12/2023 |
| WO | 2024/003537 A1 | 1/2024 |
| WO | 2024/057025 A1 | 3/2024 |
| WO | 2024/057026 A1 | 3/2024 |

OTHER PUBLICATIONS

Peters et al.: A prospective, single-blind, randomized crossover trial of sacral vs pudendal nerve stimulation for interstitial cystitis. BJU Int. 2007;100:835-839 (2007).

Standring, S. et al., Gray's anatomy. 39th Ed. Amsterdam: Elsevier, Churchill Livingstone. 2005.

Young, R. F., et al., "Electrical stimulation of the trigeminal nerve root for the treatment of chronic facial pain", JNS, vol. 83, No. 1, Jul. 1995, pp. 72-78.

Spinelli et al.: A New Minimally Invasive Procedure for Pudenda! Nerve Stimulation to Treat Neurogenic Bladder: Description of the Method and Preliminary Data. Neurourololgy and Urodynamics. 24:305-309 (2005).

Sterne et al.: RoB 2: a revised tool for assessing risk of bias in randomised trials. BMJ. 366(14898):1-8 (2019).

Su et al.: Electromyographic Responses Across Different Pulse-Widths of Sacral Neuromodulation in Sheep. Neuromodulation. 22:684-689 (2018).

Tai et al.: Bladder Inhibition or Voiding Induced by Pudenda! Nerve Stimulation in Chronic Spinal Cord Injured Cats. Neurourol Urodyn. 26:570-577 (2007).

Talatt, M., Afferent Impulses in the Nerves Supplying the Urinary Bladder, J Physiol (Lon) 1937, vol. 89, pp. 1-13.

Tanagho et al.: Electrical stimulation in the clinical management of the neurogenic bladder. J Urol. 140:1331-1339 (1988).

Thin et al.: Systematic review of the clinical effectiveness of neuromodulation in the treatment of faecal incontinence. Br J Surg. 100:1430-1447 (2013).

(56) References Cited

OTHER PUBLICATIONS

Thomas et al.: A pilot study of chronic pudenda! nerve stimulation for faecal incontinence for those who have failed sacral nerve stimulation. Tech Coloproctl: 18:731-737 (2014).
Thuroff et al.: Chronic stimulation of the sacral roots in dogs. Eur Urol. 9:102-108 (1983).
Thuroff et al.: Functional pattern of sacral root stimulation in dogs. II. Urethral closure. J Urol. 127:1034-1038 (1982).
Thuroff et al.: Mechanisms of urinary continence: an animal model to study urethral responses to stress conditions. J Urol. 127:1202-1206 (1982).
Todd, JK., Afferent Impulses in the Pudenda! Nerves of the Cat, Q J Exp Physiol Cogn Med Sci 1964;49, No. 3, pp. 258-267.
Toth et al.: DyNeuMo Mk-2: An Investigational Circadian-Locked Neuromodulator with Responsive Stimulation for Applied Chronobiology, Conf Proc IEEE Int Conf Syst Man Cybern. 2020:3433-3440 (2020).
Uludag et al.: Effect of sacral neuromodulation on the rectum. Br J Surg. 92:1017-1023 (2005).
Vaganee et al.: Needle Placement and Position of Electrical Stimulation Inside Sacral Foramen Determines Pelvic Floor Electromyographic Response—Implications for Sacral Neuromodulation. Neuromodulation. 22:1-6 (2019).
Vaganee et al.: Neural pathway of bellows response during SNM treatment revisited: Conclusive evidence for direct efferent motor response. Neurourol Urodyn. 39:1-8 (2020).
Vaganee et al.: Pelvic Floor Muscle Electromyography as a Guiding Tool During Lead Placement and (Re) Programming in Sacral Neuromodulation Patients: Validity, Reliability, and Feasibility of the Technique. Neuromodulation. 23:1-8 (2020).
Van Asselt, E. et al., "A comparative study of voiding in rat and guinea pig: simultaneous measurement of flow rate and pressure", Am J Physiol, 1995, vol. 269, R98-103.
Van Breda et al.: Subject-Controlled, On-demand, Dorsal Genital Nerve Stimulation to Treat Urgency Urinary Incontinence; a Pilot. Front Neurosci. 10(24):1-7 (2016).
Vansteensel et al.: Fully Implanted Brain-Computer Interface in a Locked-In Patient with ALS. The New England Journal of Medicine. 375(21):2060-2066 (2016).
Vodusek et al.: Detrusor Inhibition Induced by Stimulation of Pudenda! Nerve Afferents. Neurourology and Urodynamics. 5:381-389 (1986).
Vodusek et al.: Detrusor inhibition on selective pudenda! nerve stimulation in the perineum. Neurourol Urodyn. 6:389-393 (1988).
Wang et al.: Efficacy of Electrical Pudenda! Nerve Stimulation in Treating Female Stress Incontinence. Urology. pp. 1-10 (2016). dx.doi.org/doi: 10.1016/j.urology.2016.02.027.
Wang et al.: Efficacy of Electrical Pudenda! Nerve Stimulation versus Transvaginal Electrical Stimulation in Treating Female Idiopathic Urgency Urinary Incontinence. J Urol. 1-17 (2017) doi:10.1016/j.juro.2017.01.065.
Wang et al.: Long-term efficacy of electrical pudenda! nerve stimulation for urgency-frequency syndrome in women. Int Urogynecol J. 25:397-402 (2014).
Wang et al.: Simultaneous perinea! ultrasound and vaginal pressure measurement prove the action of electrical pudenda! nerve stimulation in treating female stress incontinence. BJU Int. 110:1338-1343 (2012).
Wei et al.: Functional Electrical Stimulation as a Neuroprosthetic Methodology for Enabling Closed-loop Urinary Incontinence Treatment, Proceedings ofthe5th International IEEE Embs Conference on Neural Engineering. pp. 650-654 (2011).
Wenzel et al.: Closed Loop Electrical Control of Urinary Continence. The Journal of Urology. 175:1559-1563 (2006).
Wenzel et al.: Detecting the onset of hyper-reflexive bladder contractions from the electrical activity of the pudenda! nerve. IEEE Trans Neural Syst Rehabil Eng. 13(3):428-435 (2005).
Wenzel et al.: Detection of neurogenic detrusor contractions from the activity of the external anal sphincter in cat and human. Neurourol Urodyn. 25:140-147 (2005).
Woock et al.: Activation and inhibition of the micturition reflex by penile afferents in the cat. Am J Physiol Regul Integr Comp Physiol. 294:R1880-1889 (2008).
Woock et al.: Mechanisms of Reflex Bladder Activation by Pudenda! Afferents. Am J Physiol Regul Integr Comp Physiol. 300:R398-407 (2011).
Woock, J.P., "Intraurethral stimulation evokes bladder responses via 2 distinct reflex pathways", J Urol, 2009, vol. 182, pp. 366-373.
Wunderlich et al.: The overlapping innervation of the two sides of the external anal sphincter by the pudenda! nerves. J Neural Sci. 59:97-109 (1983).
Wyndaele et al. Mechanisms of pelvic organ crosstalk: 1. Peripheral modulation of bladder inhibition by colorectal distention in rats. J Urol. 190:765-71 (2013).
Wyndaele et al.: Detrusor overactivity. Does it represent a difference if patients feel the involuntary contractions?. The Journal of Urology. 172:1915-1918 (2004).
Yoo et al.: Bladder Activation by Selective Stimulation of Pudenda! Nerve Afferents in the Cat. Exp Neural. 212 (1):218-225 (2008).
Herschorn et al.: Could Reduced Fluid Intake Cause the Placebo Effect Seen in Overactive Bladder Clinical Trials? Analysis of a Large Solifenacin Integrated Database Urology. 106:55-59 (2017).
Hokanson et al.: Stimulation of the sensory pudenda! nerve increases bladder capacity in the rat. Am J Physiol Renal Physiol.314:F543-F550 (2018).
Horvath et al.: Conditional and continuous electrical stimulation increase cystometric capacity in persons with spinal cord injury Neurourol Urodyn. 29(3):401-407 (2010).
Huang et al.: Preservation of pudenda! afferents in sacral rhizotomies. Neurosurgery. 41:411-415 (1997).
Ioannidis et al.: Better reporting of harms in randomized trials: an extension of the CONSORT statement, Ann Intern Med, 2004;141:781-788.
Irwin et al.: Population-based survey of urinary incontinence, overactive bladder, and other lower urinary tract symptoms in five countries: results of the EPIC study. Eur Urol. 50:1306-1314; discussion 1314-5 (2006).
Ishigooka et al.: Electrical pelvic floor stimulation in the management of urinary incontinence due to neuropathic overactive bladder. Front Med Biol Eng. 5(1):1-10 (1993).
Ishigooka et al.: Modulation of the urethral pressure by high-frequency block stimulus in dogs. Eur Urol. 25:334-337 (1994).
Jairam et al.: Onset of Action of Sacral Neuromodulation in Lower Urinary Tract Dysfunction—What is the Optimal Duration of Test Stimulation? The Journal of Urology. 199:1584-1590 (2018).
Janneck, C., "Electric stimulation of the bladder and the anal sphincter—a new way to treat the neurogenic bladder", Anorectal Malformations and Associated Diseases, Progress in Pediatric Surgery, 1976, vol. pp. 119-139.
Janssen et al.: Measurement properties of the EQ-5D-5L compared to the EQ-5D-3L across eight patient groups: a multi-country study. Qual Life Res. 22:1717-1727 (2013).
Jiang, HH. et al. "Electrical stimulation of the pudenda! nerve promotes neuroregeneration and functional recovery from stress urinary incontinence in a rat model" Am J Physiol Renal Physiol, 2018, vol. 315, F1555-F1564.
Jiang, HH. et al., "Effects of acute selective pudenda! nerve electrical stimulation after simulated childbirth injury", Am J Physiol Renal Physiol, 2013, vol. 304, F239-F247.
Jimenez-Shahed, J., "Device profile of the percept PC deep brain stimulation system for the treatment of Parkinson's disease and related disorders", Expert Rev Med Devices, 2021, vol. 18, pp. 319-332.
Jones et al.: A Joint Mechanism of Action for Sacral Neuromodulation for Bladder and Bowel Dysfunction? Urology. 97:13-19 (2016).
Jottard et al.: Endoscopic trans gluteal minimal-invasive approach for nerve liberation (ENTRAMI technique) in case of pudenda! and/or cluneal neuralgia by entrapment: One-year follow-up. Neurourol Urodyn. 39:1-5 (2020).
Jottard et al.: Pilot study: pudenda! neuromodulation combined with pudenda! nerve release in case of chronic perinea! pain syndrome. The ENTRAMI technique: early results, Int Urogynecol J. pp. 1-6 (2020).

(56) References Cited

OTHER PUBLICATIONS

Jottard et al.: The ENTRAMI technique: Endoscopic transgluteal minimal invasive technique for implantation of a pudenda! electrode under full visual control: A cadaver study. Neurourol Urodyn. 38:130-134 (2019).
Juenemann et al.: Clinical significance of sacral and pudenda! nerve anatomy. J Urol. 139:74-80 (1988).
Jung, SY, et al., "Urethral afferent nerve activity affects the micturition reflex; implication for the relationship between stress incontinence and detrusor instability", J Urol,1999;162:204-212.
Kamm et al.: Rectal mucosal electrosensory testing—evidence for a rectal sensory neuropathy in idiopathic constipation. Dis Colon Rectum. 33:419-423 (1990).
Kiff et al.: Evidence of pudenda! neuropathy in patients with perineal descent and chronic straining at stool. Gut. 25:1279-1282 (1984).
Kiff et al.: Slowed conduction in the pudenda! nerves in idiopathic (neurogenic) faecal incontinence. BrJ Surg. 71:614-616 (1984).
Knight et al.: Conditional neuromodulation of neurogenic detrusor overactivity using transrectal stimulation in patients with spinal cord injury: A proof of principle study. Neurourol Urodyn. 37:385-393 (2018).
Knowles et al.: New concepts in the pathophysiology of fecal incontinence. Annals of Laparoscopic and Endoscopic Surgery. 7(15):1-19 (2022).
Knowles et al.: Prospective randomized double-blind study of temporary sacral nerve stimulation in patients with rectal evacuatory dysfunction and rectal hyposensitivity. Ann Surg. 255:643-649 (2012).
Knowles et al.: Sensory and autonomic neuropathy in patients with idiopathic slow-transit constipation. Br J Surg. 86:54-60 (1999).
Knowles et al.: Surgery for constipation: systematic review and clinical guidance: Paper 1: Introduction & Methods Colorectal Dis. 19(Suppl 3):5-16 (2017).
Knowles et al.: The science behind programming algorithms for sacral neuromodulation. Colorectal Dis. 23:592-602 (2021).
Krier et al.: Physiological, morphological, and histochemical properties of cat external anal sphincter. Am J Physiol. 255:G772-G778 (1988).
Kruse et al.: Modulation of the spinobulbospinal micturition reflex pathway in cats. Am J Physiol. 262:R478-R484 (1992).
Landin et al.: Technology Integration Methods for Bi-directional Brain-computer Interfaces and XR-based Interventions. Conf Proc IEEE Int Conf Syst Man Cybern. Europe PMC Funders Group. 3695-3701 (2020).
Le Feser et al.: Pudenda! nerve stimulation induces urethral contraction and relaxation. Am J Physiol. 277:R1368-R1375 (1999).
Lee et al.: Semiconditional electrical stimulation of pudenda! nerve afferents stimulation to manage neurogenic detrusor overactivity in patients with spinal cord injury. Ann Rehabil Med. 35:605-612 (2011).
Lee. S,, et al., "A meta-analysis of the placebo response in antimuscarinic drug trials for overactive bladder" BMC Med Res Methodol, 2009; vol. 9, No. 55., pp. 1-2.
Li et al.: Short-term Clinical Efficacy of Electric Pudenda! Nerve Stimulation on Neurogenic Lower Urinary Tract Disease: A Pilot Research. Urology. pp. 1-22 doi.org/10.1016/j. urology.2017.10.047 (2017).
Lindstrom et al.: The neurophysiological basis of bladder inhibition in response to intravaginal electrical stimulation. J Urol. 129:405-410 (1983).
Loukas et al.: Anatomical and surgical considerations of the sacrotuberous ligament and its relevance in pudenda! nerve entrapment syndrome. Surg Radial Anat. 28:163-169 (2006).
Luber, K.M., "The definition, Prevalence, and Risk Factors for Stress Urinary Incontinence", Reviews in Urology, 2004, vol. 6, Suppl 3, pp. S3-S9.
Lubowski et al.: Faecal incontinence associated with reduced pelvic sensation. Br J Surg. 75:1086-1088 (1988).
Lyon et al.: Pudenda! but not tibial nerve stimulation inhibits bladder contractions induced by stimulation of pontine micturition center in cats. Am J Physiol Regul Integr Comp Physiol. 310:R366-R374 (2016).
Madbouly, K.M. et al., "Temporary sacral nerve stimulation in patients with fecal incontinence owing to rectal hyposensitivity: a prospective, double-blind study", Surgery, 2015, vol. 157, pp. 56-63.
Martens et al.: Minimal invasive electrode implantation for conditional stimulation of the dorsal genital nerve in neurogenic detrusor overactivity. Spinal Cord. 49:566-572 (2011).
Martens et al.: Surgical access for electrical stimulation of the pudenda! and dorsal genital nerves in the overactive bladder: a review. J Urol. 186:798-804 (2011).
Matharu G, et al., "Relationship Between Urinary Symptoms Reported in a Postal Questionnaire and Urodynamic Diagnosis", Neurouroloy and Urodynamics, 2005, vol. 24, pp. 100-105.
Matzel et al.: Electrical stimulation of sacral spinal nerves for treatment of faecal incontinence. Lancet. 346:1124-1127 (1995).
Matzel et al.: Neuroanatomy of the striated muscular anal continence mechanism. Implications for the use of neurostimulation. Dis Colon Rectum. 33:666-673 (1990).
Matzel et al.: Sacral Neuromodulation: Standardized Electrode Placement Technique. Neuromodulation. 20:816-824 (2017).
McCallum et al.: Gastric Pacing Improves Emptying and Symptoms in Patients With Gastroparesis. Gastroenterology. 114:456-461 (1998).
McCrery et al.: Treatment of Urinary Urgency Incontinence Using a Rechargeable SNM System: 6-Month Results of the ARTISAN-SNM Study, The Journal of Urology. 1-15 (2019) doi:10.1097/JU.0000000000000458.
Abrams, P. et al., "The standardisation of terminology in lower urinary tract function: report from the standardisation subcommittee of the International Continence Society", Urology, 2003;61:37-49.
Altomare et al.: Long-term outcomes of sacral nerve stimulation for faecal incontinence Br J Surg. (102):407-415 (2015).
Amundsen et al.: The Refractory Overactive Bladder: Sacral NEuromodulation vs. BoTulinum Toxin Assessment: ROSETTA trial, Contemp Clin Trials. 37(2):272-283 (2014).
Arakalitis et al.: Healthcare professional's choice for surgical management of stress urinary incontinence in a U.K. tertiary hospital, Eur J Obstet Gynecol Reprod Biol. 263:7-14 (2021).
Auchincloss et al.: The reliability of surface EMG recorded from the pelvic floor muscles, Journal of Neuroscience Methods. 182:85-96 (2009).
Avery et al.: ICIQ: A Brief and Robust Measure for Evaluating the Symptoms and Impact of Urinary Incontinence. Neurourol Urodyn. 2004;23:322-330.
Barber et al.: Innervation of the female levator ani muscles. Am J Obstet Gynecol. 187:64-71 (2002).
Barrington, F.J.F., "The component reflexes of micturition in the cat. Part III", Brain 1941;54:239-243.
Barrington, F.J.F., "The component reflexes of micturition in the cat. Parts I and II", Brain 1931;54:177-188.
Benson, K., et al., "One-year outcomes of the ARTISAN-SNM study with the Axonics System for the treatment of urinary urgency incontinence", Neurourol Urodyn 2020;39:1482-1488.
Bhadra, N. et al., "High frequency electrical conduction block of the pudenda! nerve", J Neural Eng, 2006, vol. 3, No. 2, pp. 180-187.
Binnie, NR et al., "Use of the pudenda-anal reflex in the treatment of neurogenic faecal incontinence", Gut, 1990, vol. 31, pp. 1051-1055.
Bock, S. et al., "First experiences with pudenda! nerve stimulation in fecal incontinence: a technical report", Tech Coloproctol, 2010, vol. 14, pp. 41-44.
Boggs, J et al., "Frequency-dependent selection of reflexes by pudendal afferents in the cat", J Physiol, 2006, vol. 577, pp. 115-126.
Bosch, JL., "The bion device: a minimally invasive implantable ministimulator for pudendal nerve neuromodulation in patients with detrusor overactivity incontinence", Urol Clin North Am, 2005;32:109-112.

(56) References Cited

OTHER PUBLICATIONS

Bosch, RJ, et al., "Perinea! pudenda! neurotomy versus selective neurotomy of the S2 somatic contribution to the pudenda! nerve. Effects on sacral-root-stimulated bladder and urethral responses in the dog", Urol Int, 1992;48:48-52.

Brink, TS, et al., "A Chronic, Conscious Large Animal Platform to Quantify Therapeutic Effects of Sacral Neuromodulation on Bladder Function", J Urol, 2015, vol. 194, pp. 252-258.

Chan, AW, et al., "SPIRIT 2013 statement: defining standard protocol items for clinical trials", Ann Intern Med, 2013;158:200-7.

Chan, C.L. et al., "Rectal sensorimotor dysfunction in patients with urge faecal incontinence: evidence from prolonged manometric studies", Gut, 2005, vol. 54, pp. 1263-1272.

Chartier-Kastler, E, et al., "Neuromodulation sacree avec le systeme InterStim: resultats du registre national francais", Progres en urologie, 2011;21:209-17.

Cong et al.: Effects of Acute Sacral Neuromodulation at Different Pulse Widths on Bladder Overactivity in Pigs. Int Neurourol J. 23:109-115 (2019).

Craggs, M. et al., "Neuromodulation oftheLower Urinary Tract", Exp Physiol, 1999, vol. 84, pp. 149-160.

Cumpston et al.: Updated guidance for trusted systematic reviews: a new edition of the Cochrane Handbook for Systematic Reviews of Interventions, Cochrane Database Syst Rev 10:ED000142 (2019).

Dalmose, A.L., , et al., "Conditional stimulation of the dorsal penile/clitoral nerve may increase cystometric capacity in patients with spinal cord injury", Neurourol Urodyn, 2003;22:130-137.

Desprez, C, et al., "Ten-year Evaluation of a Large Retrospective Cohort Treated by Sacral Nerve Modulation for Fecal Incontinence: Results of a French Multicenter Study", Ann Surg, 2022, vol. 275, No. 4, pp. 735-742.

Evers et al.: Reversal of sensory deficit through sacral neuromodulation in an animal model of fecal incontinence. Neurogastroenterol Motil. 28:665-673 (2016).

Evers, J, et al., "Systematic Review of Animal Models Used in Research of Origins and Treatments of Fecal Incontinence", Dis Colon Rectum, 2017; vol. 60, No. 6, pp. 614-626.

Farthing, M.J.G .et al., "Sensibility of Rectum to Distension and Anorectal Distension Reflex in Ulcerative-Colitis" Gut 1978, vol. 19, pp. 64-69.

Fassov, J.L. et al., "A Randomized, Controlled, Crossover Study of Sacral Nerve Stimulation for Irritable Bowel Syndrome", Ann Surg, 2014, vol. 260, No. 1, pp. 31-36.

Fjorback, M.V., et al., "Event driven electrical stimulation of the dorsal penile/clitoral nerve for management of neurogenic detrusor overactivity in multiple sclerosis", Neurourol Urodyn, 2006;25:349-355.

Flisser et al.: Urodynamic Classification of Patients with Symptoms of Overactive Bladder. The Journal of Urology. 169:529-533; discussion 533-534 (2003).

Fowler et al.: The neural control of micturition. Nat Rev Neurosci. 9:453-66 (2008).

Freedman et al.: Combined bladder neck suspension and augmentation cystoplasty for neuropathic incontinence in female patients. British Journal of Urology. 73:621-624 (1994).

Garry, R.C. et al., "Reflexes Involving the External Urethral Sphincter in the Cat", J Physiol, 1959, vol. 149, pp. 653-665.

George et al.: A new minimally invasive technique for pudenda! nerve stimulation. Colorectal Dis. 14:98-103 (2011).

George et al.: Pudenda! nerve stimulation for bowel dysfunction in complete cauda equina syndrome. Ann Surg. 259(3):502-507 (2014).

Godec, C., et al., "Electrical stimulation for incontinence. Technique, selection, and results", Urology, 1976; vol. 7, No. 4, pp. 388-397.

Goldman et al.: Long Term Clinical Results on Treatment of Urinary Urgency Incontinence with the Axonics Rechargeable Sacral Neuromodulation System. Journal of Urology. 203(45):E554-E555 (2020).

Goldman, H.B. et al., "Dorsal Genital Nerve Stimulation for the Treatment of Overactive Bladder Symptoms", Neurourol Urodyn 2008, vol. 27, No. 6, pp. 499-503.

Gonzalez E. et al, "Sensory pudendal nerve stimulation increases bladder capacity through sympathetic mechanisms in cyclophosphamide-induced cystitis rats", Neurourol Urodyn 2019, vol. 38, pp. 135-143.

Grigorescu, B.A. et al., "Innervation of the levator ani muscles: description of the nerve branches to the pubococcygeus, iliococcygeus, and puborectalis muscles", Int Urogynecol J Pelvic Floor Dysfunct, 2008;19:107-116.

Groen, J, et al., "Chronic pudenda! nerve neuromodulation in women with idiopathic refractory detrusor overactivity incontinence: results of a pilot study with a novel minimally invasive implantable mini-stimulator", Neurourol Urodyn 2005;24:226-30.

Grover M, et al., "Survey of geriatricians on the effect of fecal incontinence on nursing home referral", J Am Geriatr Soc, 2010;58:1058-62.

Gustafson, K.J, et al., "Fascicular anatomy and surgical access of the human pudenda! nerve", World J Urol, 2005;23:411-418.

Hannestad, Y., et al., "A community-based epidemiological survey of female urinary incontinence: the Norwegian EPINCONT study", The Journal of Clinical Epidemiology, 2000, vol. 53, pp. 1150-1157.

Hansen, J. et al., "Treatment of neurogenic detrusor overactivity in spinal cord injured patients by conditional electrical stimulation", J Urol, 2005, vol. 173, pp. 2035-2039.

Heinze, K. et al., "Comparative pilot study of implantation techniques for pudenda! neuromodulation: technical and clinical outcome in first 20 patients with chronic pelvic pain", World J Urol, 2015, vol. 33, pp. 289-294.

Heitmann et al.: Understanding the physiology of human defaecation and disorders of continence and evacuation. Nat Rev Gastroenterol Hepatol. 18:751-769 (2021).

Henry et al.: Assessment of pelvic-floor disorders and incontinence by electrophysiological recording ofthe anal reflex. Lancet. 1:1290-1291 (1978).

Herdman et al.: Development and preliminary testing of the new five-level version of EQ-5D (EQ-5D-5L). Qual Life Res. 20:1727-1736 (2011).

McGee et al.: Selective co-stimulation of pudenda! afferents enhances bladder activation and improves voiding efficiency. Neurourol Urodyn. 33(8):1272-1278 (2014).

Meyer et al.: Stimulated pressure profile at rest: a noninvasive method for assessing urethral sphincter function. Urology. 52(4):679-684 (1998).

Minagawa et al.: Mechanisms of pelvic organ cross-talk: 2. Impact of colorectal distention on afferent nerve activity of the rat bladder. J Urol. 190:1123-1130 (2013).

Moher et al.: Preferred reporting items for systematic reviews and meta-analyses: the PRISMA statement. BMJ. 339 (b2535):1-8 (2009).

Nissenkorn et al.: Patient-adjusted intermittent electrostimulation for treating stress and urge urinary incontinence. BJU International. 94:105-109 (2004).

No Author, "Excellence in Continence Care: Practical guidance for commissioners, and leaders in health and social care", NHS England, retrieved from internet https://www.england.nhs.uk/publication/excellence-in-continence-care/, retrieved on Mar. 9, 2022, pp. 1-24.

No Author, "MRC/DH/MHRA Joint Project: Risk-adapted Approaches to the Management of Clinical Trials of Investigational Medicinal Products", MHRA, retrieved from internet https://assets.publishing.service.gov.uk/government/uploads/system/uploads/attachment_data/file/343677/Risk-adapted_approaches_to_the_management_of_clinical_trials_of_investigational_medicinal_products.pdf. Version: Oct. 10, 2011, pp. 1-31.

No Author, "The economic impact of incontinence in Australia", Deloitte Access Economics, Continence Foundation of Australia, 2011, pp. 1-76.

O'Bichere et al.: New, simple approach for maximal pudenda! nerve exposure: anomalies and prospects for functional reconstruction. Dis Colon Rectum. 43(7):956-960 (2000).

Ohlsson et al.: Effects of external and direct pudenda! nerve maximal electrical stimulation in the treatment of the uninhibited overactive bladder. Br J Urol. 64:374-80 (1989).

(56) References Cited

OTHER PUBLICATIONS

Oliver et al.: Measuring the sensations of urge and bladder filling during cystometry in urge incontinence and the effects of neuromodulation. Neurourol Urodyn. 22:7-16 (2003).
Opisso et al.: Patient controlled versus automatic stimulation of pudenda! nerve afferents to treat neurogenic detrusor overactivity. J Urol. 180:1403-1408 (2008).
Opisso et al.: Subject-controlled stimulation of dorsal genital nerve to treat neurogenic detrusor overactivity at home. Neurourol Urodyn. 32:1004-1009 (2013).
Opisso et al.: Urethral sphincter EMG-controlled dorsal penile/clitoral nerve stimulation to treat neurogenic detrusor overactivity. J Neural Eng. 8:036001 pp. 1-9 (2011).
Parks, AG et al, "Sphincter denervation in anorectal incontinence and rectal prolapse", Gut, 1977, vol. 18:656-665.
Peeters et al.: Long-term follow-up of sacral neuromodulation for lower urinary tract dysfunction. BJU Int. 113:789-794 (2014).
Peng et al.: Improved Bladder Emptying in Urinary Retention by Electrical Stimulation of Pudenda! Afferents. J Neural Eng. 5:144-154 (2008).
Peng et al.: Pudenda! neuromodulation with a closed-loop control strategy to improve bladder functions in the animal study. 35th Annual International Conferences of the IEEE EMBS 201. 3626-3629 (2013).
Peng et al.: Role of pudenda! afferents in voiding efficiency in the rat. Am J Physiol Regul Integr Comp Physiol. 294: R660-R672 (2008).
Percy et al.: Electrophysiological study of motor nerve supply of pelvic floor. Lancet. 1:16-17 (1981).
Perry et al.: An epidemiological study to establish the prevalence of urinary symptoms and felt need in the community: the Leicestershire MRC Incontinence Study. Leicestershire MRC Incontinence Study Team. J Public Health Med, 22:427-434 (2000).
Peters et al. Randomized trial of percutaneous tibial nerve stimulation versus Sham efficacy in the treatment of overactive bladder syndrome: results from the SUmiT trial. J Urol 183:1438-43 (2010).
Peters et al.: Pilot Study Exploring Chronic Pudenda! Neuromodulation as a Treatment Option for Pain Associated with Pudenda! Neuralgia. Low Urin Tract Symptoms. 7:138-142 (2015).
Peters et al.: Sacral versus pudenda! nerve stimulation for voiding dysfunction: a prospective, single-blinded, randomized, crossover trial. Neurourol Urodyn. 24:643-647 (2005).
Peters, KM, et al., "Chronic pudendal neuromodulation: expanding available treatment options for refractory urologic symptoms", Neurourol Urodyn, 2010;29:1267-71.
Peters, KM., "Alternative approaches to sacral nerve stimulation", Int Urogynecol J, 2010;21:1559-1563.
Peyronnet et al.: A Comprehensive Review of Overactive Bladder Pathophysiology: On the Way to Tailored Treatment. Eur Urol. 75:988-1000 (2019).
Pezzella et al.: Two-year outcomes of the ARTISAN-SNM study for the treatment of urinary urgency incontinence using the Axonics rechargeable sacral neuromodulation system. Neurourol Urodyn. 40:714-721 (2021).
Possover, M., "A new technique of laparoscopic implantation of stimulation electrode to the pudenda! nerve for treatment of refractory fecal incontinence and/or overactive bladder with urinary incontinence" J Minim Invasive Gynecol, 2014;21:729.
Possover, M., "A novel implantation technique for pudendal nerve stimulation for treatment of overactive bladder and urgency incontinence", J Minim Invasive Gynecol, 2014, pp. 1-20, doi:10.1016/j.jmig.2014.03.026.
Previnaire et al.: Is there a place for pudendal nerve maximal electrical stimulation for the treatment of detrusor hyperreflexia in spinal cord injury patients?. Spinal Cord. 36:100-103 (1998).
Previnaire et al.: Short-term effect of pudenda! nerve electrical stimulation on detrusor hyperreflexia in spinal cord injury patients: importance of current strength. Paraplegia. 34:95-99 (1996).

Reitz, A, et al., "Afferent fibers of the pudendal nerve modulate sympathetic neurons controlling the bladder neck", Neurourol Urodyn, 2003;22:597-601.
Richardson et al.: Anticholinergic drugs and risk of dementia: case-control study. BMJ. 361:k1315 (2018).
Rogers et al.: Disposable pudenda! nerve stimulator: evaluation of the standard instrument and new device. Gut. 29:1131-1133 (1988).
Rosen et al.: Sacral nerve stimulation as a treatment for fecal incontinence. Gastroenterology. 121:536-541 (2001).
Rubin et al.: States Worse Than Death Among Hospitalized Patients With Serious Illnesses. JAMA Intern Med. 176:1557-1559 (2016).
Russo et al.: Effective Relief of Pain and Associated Symptoms With Closed-Loop Spinal Cord Stimulation System: Preliminary Results of the Avalon Study. Neuromodulation. 21(1):38-47 (2017).
Russo et al.: Sustained Long-Term Outcomes With Closed-Loop Spinal Cord Stimulation: 12-Month Results of the Prospective, Multicenter, Open-Label Avalon Study. Neurosurgery. 87:E485-E495 (2020).
Sand et al.: Pelvic floor stimulation: effect on urethral closure pressure profile In: Ostergard DR aBA, ed. Urodynamics and the Evaluation of Female Incontinence, A Practical Guide. London: Springer. 128-129 (1995).
Schmidt et al.: Micturition and the male genitourinary response to sacral root stimulation. Invest Urol. 17(2):125-129 (1979).
Schmidt et al.: Sacral Nerve Stimulation for Treatment of Refractory Urinary Urge Incontinence. The Journal of Urology. 162:352-357 (1999).
Schmidt, RA., "Technique of Pudenda! Nerve Localization for Block or Stimulation", The Journal of Urology, 1989, vol. 142, pp. 1528-1531.
Schultz-Lampel et al.: Experimental results on mechanisms of action of electrical neuromodulation in chronic urinary retention. World J Urol. 16:301-304 (1998).
Shafik, A., "Perinea! nerve stimulation for urinary sphincter control. Experimental study", Urol Res, 1994;22:151-155.
Siegel et al.: Five-Year Follow up Results of a Prospective, Multicenter Study of Patients with Overactive Bladder Treated with Sacral Neuromodulation. The Journal of Urology. 199:229-236 (2018).
Siegel et al.: Results of a prospective, randomized, multicenter study evaluating sacral neuromodulation with InterStim therapy compared to standard medical therapy at 6-months in subjects with mild symptoms of overactive bladder. Neurourol Urodyn. 34:224-30 (2015).
Snellings et al.: Effects of stimulation site and stimulation parameters on bladder inhibition by electrical nerve stimulation. BJU Int. 110:136-143 (2012).
Snooks et al.: Damage to the innervation of the voluntary anal and periurethral sphincter musculature in incontinence: an electrophysiological study. J Neural Neurosurg Psychiatry. 47:1269-1273 (1984).
Snooks et al.: The innervation of the muscles of continence. Ann R Coll Surg Engl. 68:45-49 (1986).
Afshar, P., "A translational platform for prototyping closed-loop neuromodulation systems", Front. Neural Circuits, vol. 6, Jan. 22, 2013, 15 pages.
Afshar, P., et al., "Advancing neuromodulation using a dynamic control framework.", 2011 Annual International Conference of the IEEE Engineering in Medicine and Biology, 2011.
Anjum MF et al., "Multi-night cortico-basal recordings reveal mechanisms of NREM slow-wave suppression and spontaneous awakenings in Parkinson's disease." Nature communications., Feb. 27, 2024, vol. 15, Issue 1, pp. 1793.
Benson. K. et al., "One-year outcomes of the ARTISAN-SNM study with the Axonics System for the treatment of urinary urgency incontinence," Neurourology and urodynamics, vol. 39, Issue 5, 2020, pp. 1482-1488.
Biardeau, X., "Optimization of electrical stimulation/modulation therapies in the management of neurogenic and non-neurogenic lower urinary tract dysfunction.", Diss. University of Antwerp, 2024, pp. 239.
Birder. L.A. et al., "Urethral sensation: basic mechanisms and clinical expressions," International Journal of Urology, vol. 21, 2014, pp. 13-16.

(56) References Cited

OTHER PUBLICATIONS

Blok, B., et al., "Two-year safety and efficacy outcomes for the treatment of overactive bladder using a long-lived rechargeable sacral neuromodulation system.", Neurourology and Urodynamics, vol. 39, Issue. 4, 2020, pp. 1108-1114.

Blok. B. et al., "Programming settings and recharge interval in a prospective study of a rechargeable sacral neuromodulation system for the treatment of overactive bladder," Neurourology and Urodynamics, vol. 37, Issue S2, 2018, pp. S17-S22.

Blok. B. et al., "Three month clinical results with a rechargeable sacral neuromodulation system for the treatment of overactive bladder," Neurourology and urodynamics, vol. 37, Issue S2, 2018, pp. S9-S16.

Borton D A et al., "Developing collaborative platforms to advance neurotechnology and its translation." Neuron., Oct. 28, 2020, vol. 108, Issue 2, pp. 286-301.

Botha. C. et al., "Preliminary report: modulation of parasympathetic nervous system tone influences oesophageal pain hypersensitivity," Gut, vol. 64, Issue 4, 2015, pp. 611-617.

Carrington, E. V. et al., "Sa2032 Anal Evoked Potentials At 'Twitch' Threshold: A New Method for Exploration of Anal Sensory Function", Neurogastroenterology & Motility, vol. 62, No. Suppl 1, Jun. 2013, 1 page.

Cui et al., "Acute to long-term characteristics of impedance recordings during neurostimulation in humans." Journal of neural engineering., Apr. 3, 2024, vol. 21, Issue 2, pp. 026022.

D'Ancona. C. et al., "The International Continence Society (ICS) report on the terminology for adult male lower urinary tract and pelvic floor symptoms and dysfunction," Neurourology and urodynamics, vol. 38, Issue 2, 2019, pp. 433-477.

De Bock et al., "Influence of nerve transsections and combined bladder filling on intravesical electrostimulation-induced bladder contraction in the rat," European urology, vol. 56, Issue 3, 2009, pp. 527-533.

De Wacher, et al., "Can a faked cystometry deceive patients in their perception of filling sensations? A study on the reliability of spontaneously reported cystometric filling sensations in patients with non-neurogenic lower urinary tract dysfunction," Neurourology and Urodynamics: Official Journal of the International Continence Society, vol. 27, Issue 5, 2008, pp. 395-398.

De Wachter et al., "New technologies and applications in sacral neuromodulation: an update," Advances in therapy, vol. 37, 2020, pp. 637-643.

De Wachter et al., "Sacral neuromodulation: mechanism of action," European urology focus, vol. 6, Issue 5, 2020, pp. 823-825.

Deli A, et al., "Bioelectronic Zeitgebers: targeted neuromodulation to re-establish circadian rhythms." In2023 IEEE International Conference on Systems, Man, and Cybernetics (SMC) Oct. 1, 2023, IEEE., pp. 2301-2308.

Denison, T., et al., "A 2 μW 100 nV/rtHz Chopper-Stabilized Instrumentation Amplifier for Chronic Measurement of Neural Field Potentials", IEEE Journal of Solid-State Circuits, vol. 42, No. 12, Dec. 2007, pp. 2934-2945.

Devane, L. A. et al., "Acute lumbosacral nerve stimulation does not affect anorectal motor function in a rodent model", Neurogastroenterology & Motility, vol. 28, No. 3, Mar. 2016, pp. 358-363.

Dudding, T. C. et al., "Sacral Nerve Stimulation With Interstim® For The Treatment Of Faecal Incontinence Refractory To Conservative Treatment: A Cost-Utility Analysis", European Society of Coloproctology Dublin, HTA Consulting, Sep. 23-25, 2015, 1 page.

Duddling. T.C. et al., "Reprogramming sacral neuromodulation for sub-optimal outcomes: evidence and recommendations for clinical practice," Neuromodulation: Technology at the Neural Interface, vol. 24, Issue 7, 2021, pp. 1247-1257.

Eggermont. M. et al., "Innervation of the Epithelium and Lamina Propria of the Urethra of the Female Rat," The Anatomical Record, vol. 302, Issue 2, 2019, pp. 201-214.

Eggermont. M. et al., "Regional structural and functional specializations in the urethra of the female rat: evidence for complex physiological control systems," The Anatomical Record, vol. 301, Issue 7, 2018, pp. 1276-1289.

Feldmann L K, et al., "Toward therapeutic electrophysiology: beta-band suppression as a biomarker in chronic local field potential recordings." npj Parkinson's Disease. Apr. 19, 2022, vol. 8, Issue 1, pp. 44.

Fleming J E, et al., "Embedding digital chronotherapy into bioelectronic medicines." Iscience. Apr. 15, 2022, vol. 25, Issue 4, pp. 1-13.

Fleming J E, et al., "From dawn till dusk: Time-adaptive bayesian optimization for neurostimulation." PLOS Computational Biology., Dec. 13, 2023, vol. 19, Issue 12, pp. e1011674.

Gillespie, J. I., et al., "On the origins of the sensory output from the bladder: the concept of afferent noise.", BJU international, vol. 103, No. 10, 2009, pp. 1324-1333.

Goldman. H.B. et al., "International Continence Society best practice statement for use of sacral neuromodulation," Neurourology and urodynamics, vol. 37, Issue 5, 2018, pp. 1823-1848.

Grossi, U. et al., "Clinical utility of anorectal manometry for the diagnosis of dyssynergic defaecation: blinded assessment reveals that existing criteria do not differentiate between patients and controls", Neurogastroenterology & Motility, vol. 65, Sep. 2014, 11 pages.

Grossi. U. et al., "Diagnostic accuracy study of anorectal manometry for diagnosis of dyssynergic defecation," Gut, vol. 65, Issue 3, 2016, pp. 447-455.

Gunduz A et al., "Adding wisdom to 'smart'bioelectronic systems: a design framework for physiologic control including practical examples." Bioelectronics in medicine., Mar. 1, 2019, vol. 2, Issue 1, pp. 29-41.

Heesakkers. J. et al., "A prospective study to assess the effectiveness and safety of the BlueWind System in the treatment of patients diagnosed with urgency urinary incontinence," Neurourology and Urodynamics, vol. 43, Issue 7, 2024, pp. 1491-1503.

Heesakkers. J. et al., "LBA01-05 Pivotal Study of a Novel Wirelessly Powered, Patient Tailored Programmed, Tibial Neurostimulator for the Treatment of Patients With Overactive Bladder," Journal of Urology, vol. 209, Supplement 4, 2023, pp. e1178.

Herroelen, S., et al., "Pudendal nerve stimulation for treatment of lower urinary tract symptoms: A systematic review of safety, technical feasibility and clinical efficacy.", Continence, 2024.

Horrocks, E. et al., "PTU-051 Post-Partum Defecatory Dysfunction: A Complex Problem Involving Co-Existing Faecal Incontinence and Rectal Evacuatory Disorder", GI physiology, vol. 62, No. Suppl 1, Jun. 2013, 1 page.

International Search Report and Written Opinion received for PCT Patent Application No. PCT/GB24/052215, mailed on Jan. 13, 2025, 19 pages.

Invitation to Pay Additional Fees received for PCT Patent Application No. PCT/GB2024/052215, mailed on Nov. 22, 2024, 10 pages.

Jottard, K., "Surgical innovations in the treatment of pudendal and/or cluneal nerve entrapment syndrome.", Diss. University of Antwerp, 2022.

Jottard. K. et al., "Diagnosis and treatment of pudendal and inferior cluneal nerve entrapment syndrome: a narrative review," Acta Chirurgica Belgica, vol. 122, Issue 6, 2022, pp. 379-389.

Kavoosi A, et al., "MorpheusNet: Resource efficient sleep stage classifier for embedded on-line systems." In2023 IEEE International Conference on Systems, Man, and Cybernetics (SMC), Oct. 1, 2023, IEEE., pp. 2315-2320.

Knowles. C.H. et al., "The science behind programming algorithms for sacral neuromodulation," Colorectal Disease, vol. 23, Issue 3, 2021, pp. 592-602.

Kremen V et al., "Continuous active probing and modulation of neural networks with a wireless implantable system." In2017 IEEE biomedical circuits and systems conference (BioCAS), Oct. 19, 2017, IEEE., pp. 1-4.

Lehur. P. et al., "Programming algorithms for sacral neuromodulation: clinical practice and evidence—recommendations for day-to-day practice," Neuromodulation: Technology at the Neural Interface, vol. 23, Issue 8, 2020, pp. 1121-1129.

(56) References Cited

OTHER PUBLICATIONS

Leong. R.K. et al., "Current information on sacral neuromodulation and botulinum toxin treatment for refractory idiopathic overactive bladder syndrome: a review," Urologia internationalis, vol. 84, Issue 3, 2010, pp. 245-253.
Leong. R.K. et al., "PNE versus 1st stage tined lead procedure: a direct comparison to select the most sensitive test method to identify patients suitable for sacral neuromodulation therapy," Neurourology and urodynamics, vol. 30, Issue 7, 2011, pp. 1249-1252.
Maeda, Y. et al., "Sacral nerve stimulation for faecal incontinence and constipation: a European consensus statement", Colorectal Dis., vol. 17, No. 4, Apr. 2015, pp. 74-87.
Marcelissen. T. et al., "Psychological and psychiatric factors as predictors for success in sacral neuromodulation treatment," BJU International—British Journal of Urology, vol. 108, Issue 11, 2011, pp. 1834-1837.
Marcelissen. T. et al., "Sacral neuromodulation as a treatment for neuropathic clitoral pain after abdominal hysterectomy," International urogynecology journal, vol. 21, 2010, pp. 1305-1307.
Mehnert. U. et al., "The management of urine storage dysfunction in the neurological patient," SN Comprehensive Clinical Medicine, vol. 1, 2019, pp. 160-182.
Naimi. H. et al., "An innovative, non-invasive sensation meter allows for a more comprehensive understanding of bladder sensation events: a prospective study in participants with normal bladder function," Neurourology and urodynamics, vol. 38, Issue 1, 2019, pp. 208-214.
Neels, H., "Pelvic floor dysfunction in women: tackling barriers.", University of Antwerp, 2018.
Okun et al., "Definition of implanted neurological device abandonment: a systematic review and consensus statement." JAMA network open., Apr. 1, 2024, vol. 7, Issue 4, pp. e248654-e248654.
Peterken F et al., "Adapting the Finetech-Brindley Sacral Anterior Root Stimulator for Bioelectronic Medicine." In2021 43rd Annual International Conference of the IEEE Engineering in Medicine & Biology Society (EMBC), Nov. 1, 2021, IEEE., pp. 6406-6411.
Petkos K, et al., A high-performance 8 nV/v Hz 8-channel wearable and wireless system for real-time monitoring of bioelectrical signals. Journal of neuroengineering and rehabilitation. Dec. 2019, vol. 16, pp. 1-24.
Pezella. A. et al., "Two-year outcomes of the ARTISAN-SNM study for the treatment of urinary urgency incontinence using the Axonics rechargeable sacral neuromodulation system," Neurourology and urodynamics, vol. 40, Issue 2, 2021, pp. 714-721.
Pochopien, M. et al., "PMD85—Cost-Utility Analysis of Sacral Nerve Stimulation for The Treatment of Fecal Incontinence Refractory to Conservative Treatment: Looking for Optimal Treatment Path", Value in Health, ISPOR, vol. 18, No. 7, Nov. 2015, 359 pages.
Puyuelo, O., et al., "Real-life after sacral nerve modulation implantation: Rate, reasons, and risk factors for mid-term follow-up discontinuation.", Progres en Urologie, vol. 33, Issue. 17, 2023, pp. 1047-1061.
Quaghebeur, J. et al., "A brief physiology and pathophysiology of the bladder," Annals of Translational Medicine, vol. 12, Issue 2, 2024, 8 pages.
Quaghebeur, J. et al., "A critical analysis of integral theory statements concerning pathogenesis of LUTS and chronic pelvic pain," Pelviperineology, vol. 43, Issue 1, 2024, pp. 30-39.
Quaghebeur, J. et al., "Peripheral muscle force balance/imbalance in neurological binary control of bladder function and dysfunction," Annals of Translational Medicine, vol. 12, Issue 2, 2024, 10 pages.
Quaghebeur. J. et al, "The integral theory, pelvic floor biomechanics, and binary innervation," International Neurourology Journal, vol. 28, Issue 3, 2024, pp. 181-184.
Roarr B N, et al., "OMNI: Open Mind Neuromodulation Interface for accelerated research and discovery." In2021 10th International IEEE/EMBS Conference on Neural Engineering (NER), May 4, 2021, IEEE., pp. 985-988.

Sakakibara, R., et al., "Lower urinary tract dysfunction in uncommon neurological diseases, Part III: A report of the Neuro-urology Promotion Committee of the International Continence Society.", Continence, vol. 11, 2024.
Sermon et al., "1: 2 entrainment is not a device-induced artefact, except when it is." Brain stimulation., Feb. 6, 2024, vol. 17, Issue 2, pp. 149.
Seth, J. et al., "Single Centre Randomised Pilot Study Of Two Regimens (30 Mins Daily Or 30 Mins Weekly For 12 Weeks) Of Transcutaneous Tibial Nerve Stimulation Using A Novel Device For Treating Multiple Sclerosis-Related Overactive Bladder Symptoms", Journal of Neurology, Neurosurgery and Psychiatry, vol. 86, No. 11, 2015, 1 page.
Sinha, S., et al., "Lower urinary tract dysfunction in uncommon neurological diseases, Part II: A report of the Neuro-urology Promotion Committee of the International Continence Society.", Continence, vol. 7, 2023.
Sladky V, et al., "Integrated human-machine interface for closed-loop stimulation using implanted and wearable devices." In2022 IEEE International Conference on Systems, Man, and Cybernetics (SMC), Oct. 9, 2022, IEEE., pp. 1730-1735.
Sorkhabi M M et al., "A neurostimulator system for real, sham, and multi-target transcranial magnetic stimulation." Journal of neural engineering., Apr. 12, 2022, vol. 19, Issue 2, pp. 026035.
Sorkhabi M M, et al., "Design analysis and circuit topology optimization for programmable magnetic neurostimulator." In2021 43rd Annual International Conference of the IEEE Engineering in Medicine & Biology Society (EMBC), Nov. 1, 2021, IEEE., pp. 6384-6389.
Sorkhabi M, et al., "Estimation of the Motor Threshold for Near-Rectangular Stimuli Using the Hodgkin-Huxley Model." Computational intelligence and neuroscience., 2021, vol. 2021, Issue 1, pp. 4716161.
Sorkhabi MM, et al., "Numerical modeling of plasticity induced by quadri-pulse stimulation." IEEE Access., Feb. 8, 2021, vol. 9, pp. 26484-26490.
Tilborghs. S. et al., "Sacral neuromodulation for the treatment of overactive bladder: systematic review and future prospects," Expert review of medical devices, vol. 19, Issue 2, 2022, pp. 161-187.
Toth. R et al., "DyNeuMo Mk-2: an investigational circadian-locked neuromodulator with responsive stimulation for applied chronobiology," 2020 IEEE International Conference on Systems, Man, and Cybernetics (SMC). IEEE, 2020, pp. 3433-3440.
Tu. L.M. et al., "Initial clinical experience with selective bladder denervation for refractory overactive bladder," Neurourology and Urodynamics, vol. 38, Issue 2, 2019, pp. 644-652.
Vaganee. D. et al., "Needle placement and position of electrical stimulation inside sacral foramen determines pelvic floor electromyographic response-implications for sacral neuromodulation," Neuromodulation: Technology at the Neural Interface, vol. 22, Issue 6, 2019, pp. 709-715.
Vaganee. D. et al., "Repeatability of tools to assist in the follow up and troubleshooting of sacral neuromodulation patients using the sensory response," Neurourology and Urodynamics, vol. 38, Issue 2, 2019, pp. 801-808.
Van Meel et al., "Repeated ice water tests and electrical perception threshold determination to detect a neurologic cause of detrusor overactivity," Urology, vol. 70, Issue 4, 2007, pp. 772-776.
Voorham. J.C. et al., "The effect of EMG biofeedback assisted pelvic floor muscle therapy on symptoms of the overactive bladder syndrome in women: a randomized controlled trial," Neurourology and urodynamics, vol. 36, Issue 7, 2017, pp. 1796-1803.
Wendt K, et al., "Physiologically informed neuromodulation." Journal of the Neurological Sciences., Mar. 15, 2022, vol. 434, pp. 120121.
Wiest C, et al., "Evoked resonant neural activity in subthalamic local field potentials reflects basal ganglia network dynamics." Neurobiology of disease. Mar. 1, 2023, vol. 178, pp. 106019.

(56) References Cited

OTHER PUBLICATIONS

Zamora M, et al., "DyNeuMo Mk-1: Design and pilot validation of an investigational motion-adaptive neurostimulator with integrated chronotherapy." Experimental neurology. May 1, 2022, vol. 351, pp. 113977.

* cited by examiner

DEVICES, SYSTEMS, AND METHODS FOR INCONTINENCE CONTROL

CROSS-REFERENCE

This application is a continuation of U.S. application Ser. No. 18/213,225, filed Jun. 22, 2023, which is a continuation of U.S. application Ser. No. 18/068,020 filed Dec. 19, 2022, which is a continuation of U.S. application Ser. No. 17/692,611, filed Mar. 11, 2022, now U.S. Pat. No. 11,565,109, issued Jan. 31, 2023, which claims the benefit of U.S. Provisional Application No. 63/160,322, filed Mar. 12, 2021, which are incorporated herein by reference in their entirety.

BACKGROUND

Incontinence, or a lack of control over micturition or bowel movements, has many causes but commonly involves injury or weakness of the pelvic floor muscles and the nerves that innervate these muscles and involved organs. Electrical stimulation has been used to treat incontinence by stimulating the muscle directly or the sacral nerve to improve control over micturition and defecation.

SUMMARY

A lack of voluntary control over micturition, defecation, incontinence, or any combination thereof is a problem that can impact quality of life and cause social embarrassment. Urinary incontinence, or loss of bladder control, fecal incontinence, loss of control of bowel movements, or any combination thereof often relate to neurological issues.

Electrical stimulation has been used to treat incontinence by stimulating the muscle directly, sacral nerve, or other pelvic nerves to improve control over micturition and bowel movements. However, electrical nerve stimulation approaches usually only deliver a set stimulation protocol and are not capable of adapting to the condition of the subject. This can result in overstimulating or under stimulating the target area, resulting in inadequate control over micturition or bowel defecation. Therefore, it would be beneficial to deliver an electrical stimulation that accounts for the condition of the subject and adapts the stimulation level accordingly.

Additionally, traditional approaches to treating incontinence overlook that an innate human response (i.e. reflex) to prevent an incontinent event may be insufficient rather than absent. For some individuals who exhibit incontinence events, it may be that an innate mechanism for preventing incontinence is not entirely absent but rather is insufficient. For example, some individuals who suffer from incontinence may experience insufficient preventative response, such as a muscle contraction of at least one pelvic floor muscle to prevent a leakage event in response to an increased intra-abdominal pressure. In some instances, the leakage event may be urine, or alternatively gas or stool. Additionally, some individuals who suffer from stress incontinence may exhibit a delayed response to preventing an incontinence event in response to a stress event. Alternatively, some individuals may suffer from stress incontinence related to urethral hypermobility (i.e., insufficient support) that may lead to an increased pressure transmitted to the bladder and subsequently an incontinence event.

Aspects of the disclosure herein provide a method for preventing an episode of incontinence in an individual in need thereof, the method comprising: (a) implanting a sensor and an stimulator electrode within a body of the individual; (b) sensing, with the sensor electrode, a parameter that is associated with a response from the individual that is intended to prevent an episode of incontinence; and (c) providing an electrical stimulation with the stimulation electrode, that together with the response, prevents the episode of incontinence. In some embodiments, the episode of incontinence comprises urinary incontinence. In some embodiments, the episode of incontinence comprises fecal incontinence. In some embodiments, the sensor is configured to sense a contraction of a muscle of the individual that results in a partial contraction of a sphincter or a pelvic floor muscle that controls bladder or bowel voiding. In some embodiments, the sensor electrode is positioned within the pelvis of the individual. In some embodiments, the stimulator electrode provides an electrical stimulation to the pudendal nerve. In some embodiments, the sensor and the stimulator electrode are located on a single lead. In some embodiments, the method comprises a step of providing a constant electrical stimulation at a lower intensity level than the electrical stimulation provided in step (c). In some embodiments, the episode of incontinence is urinary incontinence and is urge incontinence type. In some embodiments, the intensity or duration of the electrical stimulation provided in step (c) varies according to the response that is sense in step (b). In some embodiments, the response that is sensed in step (b) is insufficient on its own to prevent the episode of incontinence and the electrical stimulation provided in step (b) adds just enough, together with the response, to prevent the episode of incontinence. In some embodiments, the response that is sense in step (b) is insufficient on its own to prevent the episode of incontinence and the electric stimulation provided in step (b), together with the response, prevent the episode on incontinence. In some embodiments, the method comprises a step of implanting a second stimulator electrode, wherein a first stimulator electrode stimulates one pudendal nerve, and the second stimulator electrode stimulates the a different pudendal nerve. In some embodiments, the stimulator electrode stimulates one pudendal nerve, and the different stimulator electrode stimulates another spatially independent region of the same pudendal nerve. In some embodiments, the method comprises a step of implanting a different stimulator electrode, wherein the stimulator electrode stimulates the main trunk of the pudendal nerve and the different stimulator electrode stimulates the distal nerve of the pudendal nerve. In some embodiments, the distal nerve of the pudendal nerve comprises branches thereof the distal pudendal nerve. In some embodiments, the method comprises a step of implanting a different stimulator electrode, wherein the electrode stimulates the trunk of the pudendal nerve the different stimulator electrode stimulates a main branch of the pudendal nerve e.g., dorsal genital nerve. In some embodiments, the method comprises a step of implanting a different stimulator electrode, wherein the first stimulator electrode stimulates a pudendal nerve, and the different stimulator electrode stimulates a sacral spinal nerve. In some embodiments, the individual suffers from urinary incontinence of varying classification. In some cases, the various classification may comprise stress incontinence, urge incontinence, overflow incontinence, or any combination thereof (i.e., mixed incontinence). In some embodiments, the sensor and stimulator electrodes are operatively coupled to a processor and a non-transitory computer readable medium that includes software. In some embodiments, the sensor electrode is calibrated by the individual using an external input device that interfaces with the software. In some embodiments, the software is configured to record a signal from the sensor electrode. In some embodiments, the software is configured to adjust the sensor electrode in response to signal.

In some embodiments, the sensor electrode is configured to sense an EMG signal. In some embodiments, the EMG signal determines that a contraction of at least one pelvic muscle has occurred. In some embodiments, the strength of the EMG signal determines that a contraction of at least one pelvic muscle has occurred. In some embodiments, the strength of the EMG signal is proportional to the strength of the contraction of at least one pelvic muscle.

Aspects of the disclosure herein provide a system for preventing an episode of incontinence in an individual in need thereof, the apparatus comprising: (a) a sensor electrode configured to sense a parameter that is associated with a response from the individual that is intended to prevent the episode of incontinence; (b) an stimulator electrode configured to provide electrical stimulation; (c) a processor operably coupled to the sensor and stimulator electrodes; (d) a non-transitory computer readable storage medium including software configured to cause the processor to: (i) receive the parameter that is associated with the response from the individual that is intended to prevent the episode of incontinence; (ii) analyze the parameter that is associated with the response from the individual that is intended to prevent the episode of incontinence; and (iii) cause the stimulator electrode to provide the electrical stimulation to the individual so that the electrical stimulation together with the response from the individual that is intended to prevent the episode of incontinence prevents the episode of incontinence. In some embodiments, the software comprises analyzing a global positioning system (GPS) location of the individual that in combination with the parameter associated with the response from the individual is intended to prevent the episode of incontinence. In some embodiments, the episode of incontinence comprises urinary incontinence. In some embodiments, the episode of incontinence comprises fecal incontinence. In some embodiments, the episode of incontinence comprises a combination of urinary incontinence and fecal incontinence. In some embodiments, the episode of incontinence comprises urinary stress incontinence. In some embodiments, the sensor electrode is configured to sense a contraction of a muscle of the individual that results in a partial contraction of a sphincter that controls bladder or bowel voiding. In some embodiments, the sensor electrode is positioned within the pelvis of the individual. In some embodiments, the stimulator electrode provides the electrical stimulation to the pudendal nerve. In some embodiments, the sensor and stimulator electrodes are located on a single lead. In some embodiments, the stimulator electrode is configured to provide a constant electrical stimulation at a lower intensity level than the electrical stimulation provided to prevent an episode of incontinence. In some embodiments, the episode of incontinence is urinary incontinence and is urge incontinence type. In some embodiments, an intensity or duration of the electrical stimulation varies according to the response that is sensed. In some embodiments, the response that is sensed by the sensor electrode is insufficient on its own to prevent the episode of incontinence and the electrical stimulation provided adds together with the response, to prevent the episode of incontinence. In some embodiments, the system provides a lower intensity stimulation to the subject, whereby the lower intensity stimulation increased or improves the subject's tolerance to the stimulation signal. In some embodiments, the increase or improvement in the subject's tolerance provides tolerance of higher intensity stimulation signal. In some embodiments, the sensor electrode is configured to sense an EMG signal. In some embodiments, the EMG signal determines that a contraction of at least one pelvic muscle has occurred. In some embodiments, the strength of the EMG signal is proportional to the strength of the contraction of at least one pelvic muscle. In some embodiments, the stimulator electrode comprises a first stimulator electrode and a second stimulator electrode, wherein the first stimulator electrode stimulates a first pudendal nerve, and the second stimulator electrode stimulates a second pudendal nerve. In some embodiments, the individual suffers from urinary incontinence of a mixed type. In some embodiments, the sensor electrode is calibrated by the individual using an external input device that interfaces with the software. In some embodiments, the software is configured to further cause the processor to record a signal from the sensor electrode. In some embodiments, the software is configured to adjust the sensor electrode in response to the signal.

Aspects of the disclosure herein provide a non-transitory computer readable storage medium including software for preventing an episode of incontinence in an individual in need thereof, configured to cause a processor to: (i) receive a parameter by a sensor electrode that is associated with a response from the individual intended to prevent the episode of incontinence; (ii) analyze the parameter that is associated with the response from the individual that is intended to prevent the episode of incontinence; and (iii) cause an stimulator electrode to provide an electrical stimulation to the individual so that the electrical stimulation together with the response from the individual that is intended to prevent the episode of incontinence prevents the episode of incontinence. In some embodiments, the software comprises analyzing a global positioning system (GPS) location of the individual that in combination with the parameter associated with the response from the individual is intended to prevent the episode of incontinence. In some embodiments, the episode of incontinence comprises urinary incontinence. In some embodiments, the episode of incontinence comprises fecal incontinence. In some embodiments, the episode of incontinence comprises urinary stress incontinence. In some embodiments, the sensor electrode is configured to sense a contraction of a muscle of the individual that results in a partial contraction of a sphincter that controls bladder or bowel voiding. In some embodiments, the sensor electrodes, stimulation electrodes, or any combination thereof is positioned within, adjacent, or around the pelvis of the individual. In some embodiments, the stimulator electrode provides the electrical stimulation to the pudendal nerve. In some embodiments, the sensor and stimulator electrodes are located on a single lead. In some embodiments, the stimulator electrode is configured to provide a constant electrical stimulation at a lower intensity level than the electrical stimulation provided to prevent an episode of incontinence. In some embodiments, the episode of incontinence is urinary incontinence and is urge incontinence type. In some embodiments, an intensity or duration of the electrical stimulation varies according to the response that is sensed. In some embodiments, the response that is sensed by the sensor electrode may be insufficient on its own to prevent the episode of incontinence and the electrical stimulation provided adds just enough, together with the response, to prevent the episode of incontinence In some embodiments, the response that is sensed by the sensor electrode may be insufficient on its own to prevent the episode of incontinence and the electrical stimulation provided, together with the response, prevents the episode of incontinence. In some embodiments, the sensor electrode may be configured to sense an EMG signal. In some embodiments, the EMG signal may determine that a contraction of at least one pelvic muscle has occurred. In some embodiments, the strength of the EMG signal may be proportional to the strength of the contraction of at least one pelvic muscle. In some embodiments, the stimulator electrode may comprise a first stimulator electrode and a second stimulator electrode, wherein the first stimulator electrode may stimulate a first pudendal nerve and the second stimulator electrode may stimulate another portion of the pudendal nerve. In some embodiments, the first stimulator electrode may stimulate one pudendal nerve, and the second stimulator electrode may stimulate another spatially independent region of the same pudendal nerve. In some embodiments, the first stimulator electrode may stimulate the main trunk of the pudendal nerve and the second stimulator electrode may stimulate the distal nerve of the pudendal nerve. In some embodiments, the distal nerve of the pudendal nerve may comprise branches thereof the distal pudendal nerve. In some embodiments, the first stimulator electrode may stimulate the trunk of the pudendal nerve and the second stimulator electrode may stimulate a main branch of the pudendal nerve e.g., dorsal genital nerve. In some embodiments, the individual suffers from urinary incontinence of a mixed type. In some embodiments, the sensor electrode is calibrated by the individual using an external input device that interfaces with the software. In some embodiments, the software is configured to further cause the processor to record a signal from the sensor electrode. In some embodiments, the software is configured to adjust the sensor electrode in response to the signal.

Aspects of the disclosure herein provide a device for preventing an episode of incontinence in an individual in need thereof, the device comprising: (a) a sensor electrode configured to sense a parameter that is associated with a response from the individual that is intended to prevent the episode of incontinence; a stimulator electrode configured to provide electrical stimulation; and a processor operatively coupled to the sensor and stimulator electrode. In some embodiments, the episode of incontinence comprises urinary incontinence. In some embodiments, the episode of incontinence comprises fecal incontinence. In some embodiments, the episode of incontinence comprises urinary stress incontinence. In some embodiments, the sensor electrode is configured to sense a contraction of a muscle of the individual that results in a partial contraction of a sphincter that controls bladder or bowel voiding. In some embodiments, the sensor electrode is positioned within the pelvis of the individual. In some embodiments, the stimulator electrode provides the electrical stimulation to the pudendal nerve. In some embodiments, the stimulator electrode is configured to provide a constant electrical stimulation at a lower intensity level than the electrical stimulation provided to prevent an episode of incontinence. In some embodiments, the episode of incontinence is urinary incontinence and is urge incontinence type. In some embodiments, the intensity or duration of the electrical stimulation varies according to the response that is sensed. In some embodiments, the response that is sensed is insufficient on its own to prevent the episode of incontinence and the electrical stimulation provided adds just enough, together with the response, to prevent the episode of incontinence. In some embodiments, the response that is sensed is insufficient on its own to prevent the episode of incontinence and the electrical stimulation provided, together with the response, prevents the episode of incontinence. In some embodiments, the sensor electrode is configured to sense an EMG signal, ENG signal, or any combination thereof. In some embodiments, the EMG signal determines that a contraction of at least one pelvic muscle has occurred. In some embodiments, the strength of the EMG signal is proportional to the strength of the contraction of at least one pelvic muscle. In some embodiments, the stimulator electrode comprises a first stimulator electrode and a second stimulator electrode, wherein the first stimulator electrode stimulates a first pudendal nerve and the second stimulator electrode stimulates a second pudendal nerve. In some embodiments, the individual suffers from urinary incontinence of a mixed type. In some embodiments, the device further comprises a non-transitory computer readable medium that includes software. In some embodiments, the sensor electrode is calibrated by the individual using an external input device that interfaces with the software. In some embodiments, the software is configured to record a signal from the sensor electrode. In some embodiments, the software is configured to adjust the sensor electrode in response to the signal.

Aspects of the disclosure herein provide a method of data processing, said method comprising: (i) receiving a measurement of a parameter previously measured by a sensor electrode, which parameter is predictive of an episode of incontinence in an individual; (ii) analyzing the parameter; and (iii) synthesizing an electrical stimulation signal for the individual, so that when the electrical stimulation signal is provided by a stimulator electrode to the individual, the electrical stimulation signal, together with an effort from the individual that is intended to prevent an episode of incontinence, prevents the episode of incontinence. In some embodiments, the parameter is associated with a response from the individual intended to prevent an episode of incontinence. In some embodiments, the parameter is associated with the individual's effort in trying to prevent an episode of incontinence, and wherein the electrical stimulation signal is synthesized so as to supplement the individual's effort with an electrical stimulation pattern that will, together with the effort from the individual, be sufficient to prevent an episode of incontinence. In some embodiments, the response from the individual is insufficient on its own to prevent the episode of incontinence and the electrical stimulation signal is such that, when applied, it adds enough, together with the response, to prevent the episode of incontinence. In some embodiments, the episode of incontinence comprises urinary incontinence. In some embodiments, the episode of incontinence comprises fecal incontinence. In some embodiments, the episode of incontinence comprises urinary stress incontinence. In some embodiments, the parameter is a signal from a sensor electrode that is configured to sense a contraction of a muscle of the individual related to a partial contraction of a sphincter that controls bladder or bowel voiding. In some embodiments, the electrical stimulation signal is for the electrical stimulation of the pudendal nerve. In some embodiments, the electrical stimulation signal is synthesized to include a constant electrical stimulation component and a measurement parameter specific component. In some embodiments, the episode of incontinence is urinary incontinence and is urge incontinence type. In some embodiments, an intensity or duration of the electrical stimulation that will be provided by the electrical stimulation signal varies according to the value of the parameter that is received. In some embodiments, the parameter is an EMG signal. In some embodiments, the EMG signal determines that a contraction of at least one pelvic muscle has occurred. In some embodiments, a strength of the EMG signal is proportional to the strength of the contraction of at least one pelvic muscle. In some embodiments, the electrical stimulation signal comprises first and second signals for the stimulation of a first pudendal nerve and a second pudendal nerve respectively. In some embodiments, the method further comprises recording the signal previously measured by the sensor electrode. In some embodiments, the method further comprises synthesizing an adjustment signal to adjust the sensor electrode in response to the recorded signal.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
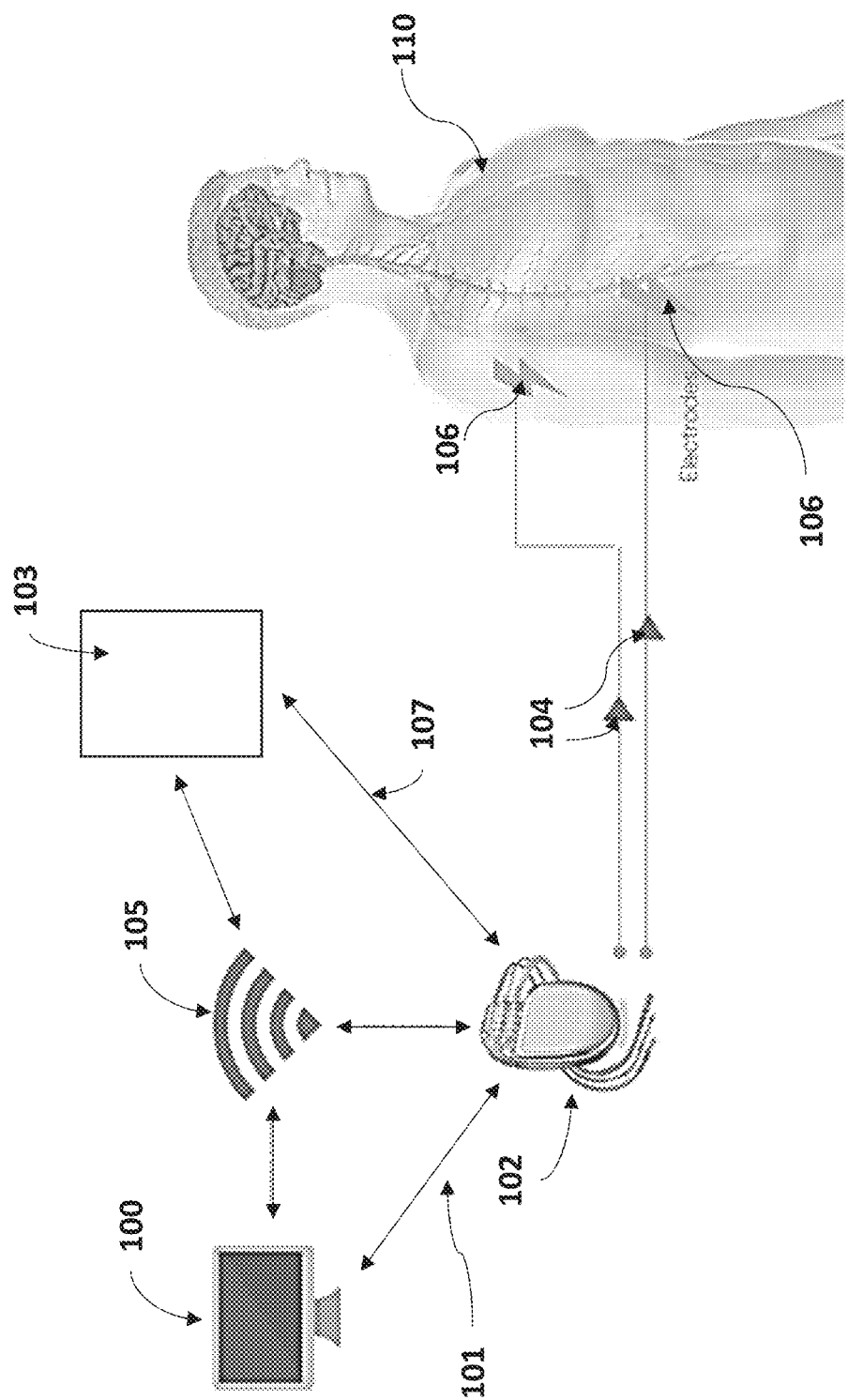
FIG. 1 shows an exemplary embodiment of an open-loop bioelectronic system comprising an implantable pulse generator. The system delivers a predefined stimulation protocol and does not receive input from the subject.

A lack of voluntary control over micturition or defecation, known as urinary and fecal incontinence, respectively, is a problem that can impact quality of life and cause social embarrassment. Urinary and fecal incontinence may affect individuals of all ages. In some cases, older individuals may exhibit a greater probability of incontinence with varied pathophysiology. Both urinary incontinence and fecal incontinence may involve injury, weakness, or overactivity of the pelvic floor muscles, including but not limited to the urethral and anal sphincter, and the nerves that innervate these muscles and involved organs, such as the bladder, rectum, or anus.

Urinary incontinence may be categorized into one of four main types: urge incontinence, stress incontinence, overflow incontinence, and mixed incontinence. Urge incontinence is often due to an overactive bladder. Individuals with urge incontinence have a strong and sudden need to urinate immediately, often leaving them with insufficient time to reach a bathroom. Stress incontinence is usually due to a poorly functioning urethral sphincter muscle or hypermobility of the urethra or bladder neck. An individual may experience stress incontinence during activities such as coughing, sneezing, laughing, or exercise. Overflow incontinence may typically be due to poor bladder contraction or blockage of the urethra. Mixed incontinence may involve features of stress and urge incontinence. Incontinence often involves neurological issues, including but not limited to impaired nerve conduction between the brain and/or the affected muscles, and nervous system conditions or injuries (e.g., multiple sclerosis or stroke), or mental confusion. Other causes of incontinence include but are not limited to weakness of pelvic or urethral muscles and pelvic prolapse.

Fecal incontinence, also referred to as bowel incontinence, is the loss of bowel control, causing an individual to pass stool unexpectedly from the rectum. Fecal incontinence may be categorized into two main types: urge incontinence, and passive incontinence, or a combination thereof. Urge incontinence is due to an overactive bowel. Individuals with urge incontinence have a strong and sudden need to defecate immediately, often leaving them with insufficient time to reach a bathroom. Passive incontinence is when an individual feels no urge to open their bowel although the rectum is full and ready to be voided. Individuals suffering from passive incontinence cannot consciously control their bowel movements and stool can pass without their knowledge.

Incontinence often involves neurological issues, including but not limited to impaired nerve conduction between the brain and/or the affected muscles, and nervous system conditions or injuries (e.g., multiple sclerosis or stroke), or mental confusion. Causes of fecal incontinence include but are not limited to nerve damage, anal sphincter muscle damage, constipation, diarrhea, hemorrhoids, surgery, loss of rectum storage capacity, rectal prolapse, and rectocele.

Electro galvanic stimulation of muscles has been used to treat incontinence by training the pelvic floor muscles thereby improving strength and function and/or by stimulating the sacral nerve to improve control over urination and defecation. However, these electrical nerve stimulation approaches are not able to adapt to the condition and circumstances of the subject and are only capable of delivering a predefined stimulation protocol. This can result in overstimulating or under stimulating the target area, resulting in inadequate control over muscles involved in urination or bowel movements. As such, it would be beneficial to be able to deliver an electrical stimulation that accounts for the condition of the subject and adapts the stimulation level accordingly.

Provided herein are devices, systems, and methods for preventing, and/or reducing the severity of an episode of incontinence in an individual in need thereof. In some instances, the episode of incontinence may comprise urinary incontinence, fecal incontinence, or any combination thereof. The devices, systems and methods disclosed herein may treat a sub-type of incontinence. In some cases, the sub-type of incontinence may comprise urge incontinence, stress incontinence, overflow incontinence, or mixed incontinence.

In some instances, the devices, systems, and methods described herein may increase bladder capacity. Bladder capacity may be measured as the maximum liquid volume a bladder may contain without inducing pain or micturition. In some cases, bladder capacity of a healthy individual as a baseline value may comprise a liquid volume of about 400 milliliters (mL) to about 600 mL. In some cases, bladder capacity may be measured by ultrasound calculations of a still ultrasound image of a subject's bladder. The bladder's volume may be measured by multiplying the length, width, and height of the measured bladder on the still ultrasound image. Alternatively, or in addition to, bladder capacity may be measured by cytometry where a catheter is inserted into the subject's urethra to fill and may measure the volume of urine. In some cases, a subject's bladder capacity may be reduced by disease. In some cases, the devices and systems described herein may increase bladder capacity by a percent increase from baseline bladder capacity. In some instances, bladder capacity may be increased by providing to the patient, an electrical stimulation by the stimulator electrode leads, described herein. In some cases, the stimulator may provide a frequency or pulse width of electrical stimulation, described elsewhere herein.

In some cases, bladder capacity may be increased utilizing either open or closed-loop system, described elsewhere herein. In some instances, bladder capacity may be increased by about 5% to about 75%. In some instances, bladder capacity may be increased by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 70%, about 5% to about 75%, about 10% to about 15%, about 10% to about 20%, about 10% to about 25%, about 10% to about 30%, about 10% to about 35%, about 10% to about 40%, about 10% to about 45%, about 10% to about 50%, about 10% to about 70%, about 10% to about 75%, about 15% to about 20%, about 15% to about 25%, about 15% to about 30%, about 15% to about 35%, about 15% to about 40%, about 15% to about 45%, about 15% to about 50%, about 15% to about 70%, about 15% to about 75%, about 20% to about 25%, about 20% to about 30%, about 20% to about 35%, about 20% to about 40%, about 20% to about 45%, about 20% to about 50%, about 20% to about 70%, about 20% to about 75%, about 25% to about 30%, about 25% to about 35%, about 25% to about 40%, about 25% to about 45%, about 25% to about 50%, about 25% to about 70%, about 25% to about 75%, about 30% to about 35%, about 30% to about 40%, about 30% to about 45%, about 30% to about 50%, about 30% to about 70%, about 30% to about 75%, about 35% to about 40%, about 35% to about 45%, about 35% to about 50%, about 35% to about 70%, about 35% to about 75%, about 40% to about 45%, about 40% to about 50%, about 40% to about 70%, about 40% to about 75%, about 45% to about 50%, about 45% to about 70%, about 45% to about 75%, about 50% to about 70%, about 50% to about 75%, or about 70% to about 75%. In some instances, bladder capacity may be increased by about 5%, about 10%, about 15%, about 20%, about 25%, about 30%, about 35%, about 40%, about 45%, about 50%, about 70%, or about 75%. In some instances, bladder capacity may be increased by at least about 5%, about 10%, about 15%, about 20%, about 25%, about 30%, about 35%, about 40%, about 45%, about 50%, or about 70%. In some instances, bladder capacity may be increased by at most about 10%, about 15%, about 20%, about 25%, about 30%, about 35%, about 40%, about 45%, about 50%, about 70%, or about 75%.

In some cases, the devices, systems, and methods described herein may increase urethral closure pressures. In some cases the urethral closure pressure may be expressed by a profile of pressures. Urethral closure pressure, in some instances, may be described as measurement of integrated pressure curves from the entire length of a subject's urethra. In some instances, urethral closure pressures may be measured by the slow withdrawal of a pressure-measuring catheter through the subject's urethra at a constant rate. In some instances, urethral closure pressures may be measured by a trans-urethral pressure profile catheter. In some cases, transurethral pressure may be measured in units of centimeters of water (cm $H_2O$). In some instances, the devices and systems described herein may increase urethral closure pressure by stimulating one or more nerves of the subject. In some instances, the one or more nerves may comprise the pudendal nerve, sacral nerve, or any combinations or branches thereof. In some cases, the stimulator described elsewhere herein, may provide an electrical stimulation at the subject's nerve, via a stimulator electrode lead at a frequency and/or frequency ranges, described elsewhere herein, to increase urethral closure pressure. In some instances, the urethral closure pressure may comprise about 10 centimeters of water (cm $H_2O$) to about 75 cm $H_2O$. In some instances, the urethral closure pressure may comprise about 10 cm $H_2O$ to about 15 cm $H_2O$, about 10 cm $H_2O$ to about 20 cm $H_2O$, about 10 cm $H_2O$ to about 25 cm $H_2O$, about 10 cm $H_2O$ to about 30 cm $H_2O$, about 10 cm $H_2O$ to about 35 cm $H_2O$, about 10 cm $H_2O$ to about 40 cm $H_2O$, about 10 cm $H_2O$ to about 45 cm $H_2O$, about 10 cm $H_2O$ to about 50 cm $H_2O$, about 10 cm $H_2O$ to about 60 cm $H_2O$, about 10 cm $H_2O$ to about 70 cm $H_2O$, about 10 cm $H_2O$ to about 75 cm $H_2O$, about 15 cm $H_2O$ to about 20 cm $H_2O$, about 15 cm $H_2O$ to about 25 cm $H_2O$, about 15 cm $H_2O$ to about 30 cm $H_2O$, about 15 cm $H_2O$ to about 35 cm $H_2O$, about 15 cm $H_2O$ to about 40 cm $H_2O$, about 15 cm $H_2O$ to about 45 cm $H_2O$, about 15 cm $H_2O$ to about 50 cm $H_2O$, about 15 cm $H_2O$ to about 60 cm $H_2O$, about 15 cm $H_2O$ to about 70 cm $H_2O$, about 15 cm $H_2O$ to about 75 cm $H_2O$, about 20 cm $H_2O$ to about 25 cm $H_2O$, about 20 cm $H_2O$ to about 30 cm $H_2O$, about 20 cm $H_2O$ to about 35 cm $H_2O$, about 20 cm $H_2O$ to about 40 cm $H_2O$, about 20 cm $H_2O$ to about 45 cm $H_2O$, about 20 cm $H_2O$ to about 50 cm $H_2O$, about 20 cm $H_2O$ to about 60 cm $H_2O$, about 20 cm $H_2O$ to about 70 cm $H_2O$, about 20 cm $H_2O$ to about 75 cm $H_2O$, about 25 cm $H_2O$ to about 30 cm $H_2O$, about 25 cm $H_2O$ to about 35 cm $H_2O$, about 25 cm $H_2O$ to about 40 cm $H_2O$, about 25 cm $H_2O$ to about 45 cm $H_2O$, about 25 cm $H_2O$ to about 50 cm $H_2O$, about 25 cm $H_2O$ to about 60 cm $H_2O$, about 25 cm $H_2O$ to about 70 cm $H_2O$, about 25 cm $H_2O$ to about 75 cm $H_2O$, about 30 cm $H_2O$ to about 35 cm $H_2O$, about 30 cm $H_2O$ to about 40 cm $H_2O$, about 30 cm $H_2O$ to about 45 cm $H_2O$, about 30 cm $H_2O$ to about 50 cm $H_2O$, about 30 cm $H_2O$ to about 60 cm $H_2O$, about 30 cm $H_2O$ to about 70 cm $H_2O$, about 30 cm $H_2O$ to about 75 cm $H_2O$, about 35 cm $H_2O$ to about 40 cm $H_2O$, about 35 cm $H_2O$ to about 45 cm $H_2O$, about 35 cm $H_2O$ to about 50 cm $H_2O$, about 35 cm $H_2O$ to about 60 cm $H_2O$, about 35 cm $H_2O$ to about 70 cm $H_2O$, about 35 cm $H_2O$ to about 75 cm $H_2O$, about 40 cm $H_2O$ to about 45 cm $H_2O$, about 40 cm $H_2O$ to about 50 cm $H_2O$, about 40 cm $H_2O$ to about 60 cm $H_2O$, about 40 cm $H_2O$ to about 70 cm $H_2O$, about 40 cm $H_2O$ to about 75 cm $H_2O$, about 45 cm $H_2O$ to about 50 cm $H_2O$, about 45 cm $H_2O$ to about 60 cm $H_2O$, about 45 cm $H_2O$ to about 70 cm $H_2O$, about 45 cm $H_2O$ to about 75 cm $H_2O$, about 50 cm $H_2O$ to about 60 cm $H_2O$, about 50 cm $H_2O$ to about 70 cm $H_2O$, about 50 cm $H_2O$ to about 75 cm $H_2O$, about 60 cm $H_2O$ to about 70 cm $H_2O$, about 60 cm $H_2O$ to about 75 cm $H_2O$, or about 70 cm $H_2O$ to about 75 cm $H_2O$. In some instances, the urethral closure pressure may comprise about 10 cm $H_2O$, about 15 cm $H_2O$, about 20 cm $H_2O$, about 25 cm $H_2O$, about 30 cm $H_2O$, about 35 cm $H_2O$, about 40 cm $H_2O$, about 45 cm $H_2O$, about 50 cm $H_2O$, about 60 cm $H_2O$, about 70 cm $H_2O$, or about 75 cm $H_2O$. In some instances, the urethral closure pressure may comprise at least about 10 cm $H_2O$, about 15 cm $H_2O$, about 20 cm $H_2O$, about 25 cm $H_2O$, about 30 cm $H_2O$, about 35 cm $H_2O$, about 40 cm $H_2O$, about 45 cm $H_2O$, about 50 cm $H_2O$, about 60 cm $H_2O$, or about 70 cm $H_2O$. In some instances, the urethral closure pressure may comprise at most about 15 cm $H_2O$, about 20 cm $H_2O$, about 25 cm $H_2O$, about 30 cm $H_2O$, about 35 cm $H_2O$, about 40 cm $H_2O$, about 45 cm $H_2O$, about 50 cm $H_2O$, about 60 cm $H_2O$, about 70 cm $H_2O$, or about 75 cm $H_2O$.

The devices and systems described herein may comprise one or more sensor electrodes, one or more stimulator electrodes, a processor, a power source, or any combination thereof. In some instances, the one or more stimulator electrodes, one or more sensor electrodes, processor, power source, or any combination thereof may be implanted into the body of the individual. In some instances, the one or more stimulator electrodes, one or more sensor electrodes, processor, power source, or any combination thereof may be placed superficially on the body of the individual. In some instances, the processor, power source, or any combination thereof may be implanted into the body of the individual. In some instances, the device may comprise a wireless transmission module capable of transmitting and receiving wireless data wireless by and between a remote device (e.g., a mobile phone, a tablet, a computer, etc.) and the incontinence prevention device described herein. In some cases, the device may be implantable into an individual. Alternatively, the device may comprise a hermetically sealed connector placed on the individual's skin superficially that may electrically couple to a remote device by a cable. In some instances, the individual may manually modify or change the one or more sensor electrode or one or more stimulator electrode parameters through a graphical user interface. In some instances, the device may automatically modify or change the one or more sensor electrode or one or more stimulator electrode parameters.

In some cases, an implanted sensor electrode of the device may be configured to sense one or more parameters that may be associated with a response of an episode of incontinence or an attempt of the individual in trying to prevent an episode of incontinence. In some cases, the parameter may comprise an electromyography (EMG) signal that may be predictive of an episode of incontinence. In some instances, EMG signals may comprise electrical activity of muscles, specifically from action potentials in muscle fibers. In some cases, the parameter may comprise an electroneurogram (ENG). In some cases, an electroneurogram may comprise electrical activity from one or more neurons and typically refers to recordings made from bundles of axons in peripheral nerves. In some cases, the parameter may comprise a change of electric impedance caused by physical deformation of the sensor electrode material. In some instances, the physical deformation may comprise stretching, compression, or any combination thereof. Alternatively, the parameter may comprise a change in pressure, velocity, acceleration, or 3-D spatial direction. In some instances, 3-D spatial direction may be determined by GPS signal. The GPS signal, in some cases, may indicate and recognize when the individual is in proximity to locations such as the individual's home. In some instances, the GPS signal may be configured to modulate the stimulator, described elsewhere herein, based on the GPS coordinates and/or GPS location of the subject. In some instances, modulating the stimulator may comprise adjusting a detection parameter (e.g., signal intensity threshold) of the classifier, described elsewhere herein. In some cases, the GPS signal of a location and/or GPS coordinates may indicate locations and/or regions traveled to the subject that may impose a higher risk of an incontinent event. In some cases, 3-D spatial direction may measure the posture of an individual. In some instances, changes in pressure may be measured by a pressure sensor. In some cases, the pressure sensor may comprise a differential pressure sensor, absolute pressure sensor, or any combination thereof. In some cases, changes in velocity, acceleration, or changes in 3-D spatial direction may be measured by an accelerometer, gyroscope, magnetometer, or any combination thereof. In some instances, the device may provide an electrical stimulation using the one or more implanted stimulator electrodes that, together with the individual's preventative response, may prevent the episode of incontinence.

The devices, systems, and methods described herein may be capable of preventing and/or reducing the severity of an incontinent event by detecting an individual's incontinence preventative parameter and adjusting an electrical stimulation by one or more stimulator electrodes based on the incontinence preventative parameter's characteristics. In some cases, the incontinence preventative parameter characteristics may comprise the changes in the amplitude, frequency, phase, or any combination thereof one or more EMG, ENG, accelerometer, gyroscope, magnetometer, pressure sensor signals, or any combination thereof. In some instances, an incontinence preventative parameter may comprise physical movement of the individual, one or more EMG signals, or any combination thereof. By providing adaptive electrical stimulation in combination to the individual's response, the devices, systems, and methods described herein may prevent incontinence episodes.

Described herein are devices, systems, and methods for preventing and/or reducing the severity of an episode of incontinence in an individual by providing adaptive electrical stimulation based on the individual's incontinence preventative parameter. The device may be implanted in the individual in proximity to the pudendal nerve, sacral nerve, or branches thereof. In some cases, the one or more stimulator electrodes of the device may be placed at or near the pudendal nerve or the sacral nerve. In some cases, the one or more stimulator electrodes or one or more sensor electrodes may be implanted in proximity to the pudendal nerve unilaterally or bilaterally. In some cases, the one or more stimulator electrodes may be implanted to stimulate motor nerve fibers (e.g., to the pelvic floor and sphincters). Alternatively, the one or more stimulator electrodes may be implanted within, proximate, or adjacent to the muscle (e.g., pelvic floor and sphincter muscles). The sensor electrode of the implanted device may sense a signal that indicates that an individual may exhibit an episode of incontinence or is trying to prevent an episode of incontinence. The device may analyze the signal and classify the signal as a real-time or prospective episode of incontinence. The device may generate an electrical stimulation that is modulated based on the classified episode of incontinence and may deliver the modulated electrical stimulation using one or more stimulator electrodes to the targeted nerve. In some instances, the modulation of the one or more stimulator electrodes electrical stimulation may comprise changing the frequency of electric stimulation, amplitude of electrical stimulation, pulse width of electric stimulation, stimulator electrode configuration, or any combination thereof. In some cases, the one or more electrodes may comprise one or more stimulation electrodes and one or more sensing electrodes. The one or more stimulation electrodes and one or more sensing electrodes may be configured to switch between stimulating and sensing operations on demand, programmatically, user controlled, medical personal control, or any combination thereof. The electrical stimulation may be modulated to improve the muscle and/or nerve response to prevent the episode of incontinence. The modulated electrical stimulation may result in improved muscle response, as measured by response time, muscle function, or other markers of incontinence prevention, to prevent the potential episode of incontinence. The electrical stimulation may be modulated to reduce a severity and/or duration of an episode of incontinence. For example, a subject who exhibits an urge incontinence event (e.g., a cough) may receive an electrical stimulation provided by the devices, systems, and methods provided herein, in response to the incontinence episode. In some cases, the electrical stimulation may reduce the volume of uncontrolled micturition and/or defecation. In some cases, the electrical stimulation may reduce the volume of uncontrolled micturition and/or defecation without preventing the episode of incontinence entirely. In some cases, the electrical stimulation may reduce the duration of the incontinent event that would occur without the electrical stimulation. In some cases, the electrical stimulation may be configured to inhibit reflex incontinence. In some cases, the electrical stimulation may inhibit a bladder detrusor muscle contraction experienced during reflex incontinence.

The electrical stimulation may comprise an electrical stimulation provided over a period of time. In some cases, the period of time may comprise the period of time a subject may provide an intent based or purposeful muscle contraction to trigger an EMG threshold detection.

In some cases, the period of time for the electrical stimulation may comprise about 1 second to about 30 seconds. In some cases, the period of time for the electrical stimulation may comprise about 1 second to about 5 seconds, about 1 second to about 10 seconds, about 1 second to about 15 seconds, about 1 second to about 20 seconds, about 1 second to about 25 seconds, about 1 second to about 30 seconds, about 5 seconds to about 10 seconds, about 5 seconds to about 15 seconds, about 5 seconds to about 20 seconds, about 5 seconds to about 25 seconds, about 5 seconds to about 30 seconds, about 10 seconds to about 15 seconds, about 10 seconds to about 20 seconds, about 10 seconds to about 25 seconds, about 10 seconds to about 30 seconds, about 15 seconds to about 20 seconds, about 15 seconds to about 25 seconds, about 15 seconds to about 30 seconds, about 20 seconds to about 25 seconds, about 20 seconds to about 30 seconds, or about 25 seconds to about 30 seconds. In some cases, the period of time may comprise about 1 second, about 5 seconds, about 10 seconds, about 15 seconds, about 20 seconds, about 25 seconds, or about 30 seconds. In some cases, the period of time for the electrical stimulation may comprise at least about 1 second, about 5 seconds, about 10 seconds, about 15 seconds, about 20 seconds, or about 25 seconds. In some cases, the period of time for the electrical stimulation may comprise at most about 5 seconds, about 10 seconds, about 15 seconds, about 20 seconds, about 25 seconds, or about 30 seconds.

Embodiments of a Device for Treating and Preventing Incontinence

The disclosure describes devices for preventing an episode of incontinence comprising one or more sensor electrodes, one or more stimulator electrodes, an electric stimulator, or any combination thereof. In some cases, the electric stimulator may comprise a processor, memory, a user interface, a power source, or any combination thereof for preventing an episode of incontinence. The devices may be implantable. The surgical procedure to implant the device may be completed under awake sedation, general anesthesia, local anesthesia, twilight anesthesia, or any combination thereof. The devices may be implanted wholly or partly in an individual's pelvic region. In some cases, the devices may be implanted by one or more surgical instruments. In some instances, surgical instruments may comprise introducers, sheaths, directable probes, wires, needles, or any combination thereof.

In some cases, the device may further comprise a transmitter electrically coupled to a processor capable of wirelessly transmitting and receiving data from a remote device, such as a mobile phone, a tablet, or a computer. In some cases, the device may be configured for open-loop configuration. In some cases, the device may be configured for a close-loop or feedback-controlled configuration. The devices described herein may be used to prevent an episode of urinary incontinence. In some instances, urinary incontinence may comprise urge incontinence, stress incontinence, overflow incontinence, mixed incontinence, or any combination thereof. In some embodiments, the episode of incontinence is urinary incontinence and is urge incontinence type. In some cases, the devices described herein may be used to prevent an episode of fecal incontinence.

Open Loop Configuration

FIG. 1 shows an open loop configuration of the device described herein configured to prevent an episode of incontinence for an individual 110. The device in an open loop configuration may comprise an implantable pulse generator 102 comprising one or more stimulator electrodes 106, and a power source. In some cases, the implantable pulse generator 102 may comprise a processor, and a wireless transmission module configured to execute software to administer an electrical stimulation pattern 104. In some cases, the power source may comprise a battery. In some instances, the battery may be a lithium polymer ion battery, lithium iodine, lithium manganese dioxide, lithium carbon monofluoride, or any combination thereof. In some cases, the battery may be wirelessly charged by an inductive charger. Alternatively, the battery power source may be a single use.

The implantable pulse generator 102 may deliver a predefined electrical stimulation pattern 104 that has been set by a healthcare provider on a remote device 100 (e.g., a mobile phone, a tablet, a computer, etc.) and transmitted wirelessly 105 to the implantable pulse generator 102. Alternatively, the implantable pulse generator 102 may deliver a predefined electrical stimulation pattern 104 that has been set by a healthcare provider on a remote computing device 100 (e.g., a mobile phone, a tablet, a computer, etc.) and transmitted via a wired communication 101 to the implantable pulse generator 102. In some instances, the healthcare provider may set the predefined electrical stimulation parameters through a graphical user interface on the remote device. In some cases, an individual 110 with an implantable pulse generator 102 may modify or set electrical stimulation parameters via an external input device 103 (e.g., a mobile phone, a tablet, a computer, etc.) via a wireless communication 105 of the implantable pulse generator 102. Alternatively, an individual 110 with an implantable pulse generator 102 may modify or set electrical stimulation parameters via an external input device 103 via a wired communication 107 of the implantable pulse generator 102. In some instances, an individual 110 with an implantable pulse generator 102 may adjust the electrical stimulation pattern 104 using a graphical user interface on the external input device 103. In some cases, the electrical stimulation pattern 104 parameters that may be adjusted comprise frequency, amplitude, pulse width, or any combination thereof.

Closed Loop Configuration

Figure 2:
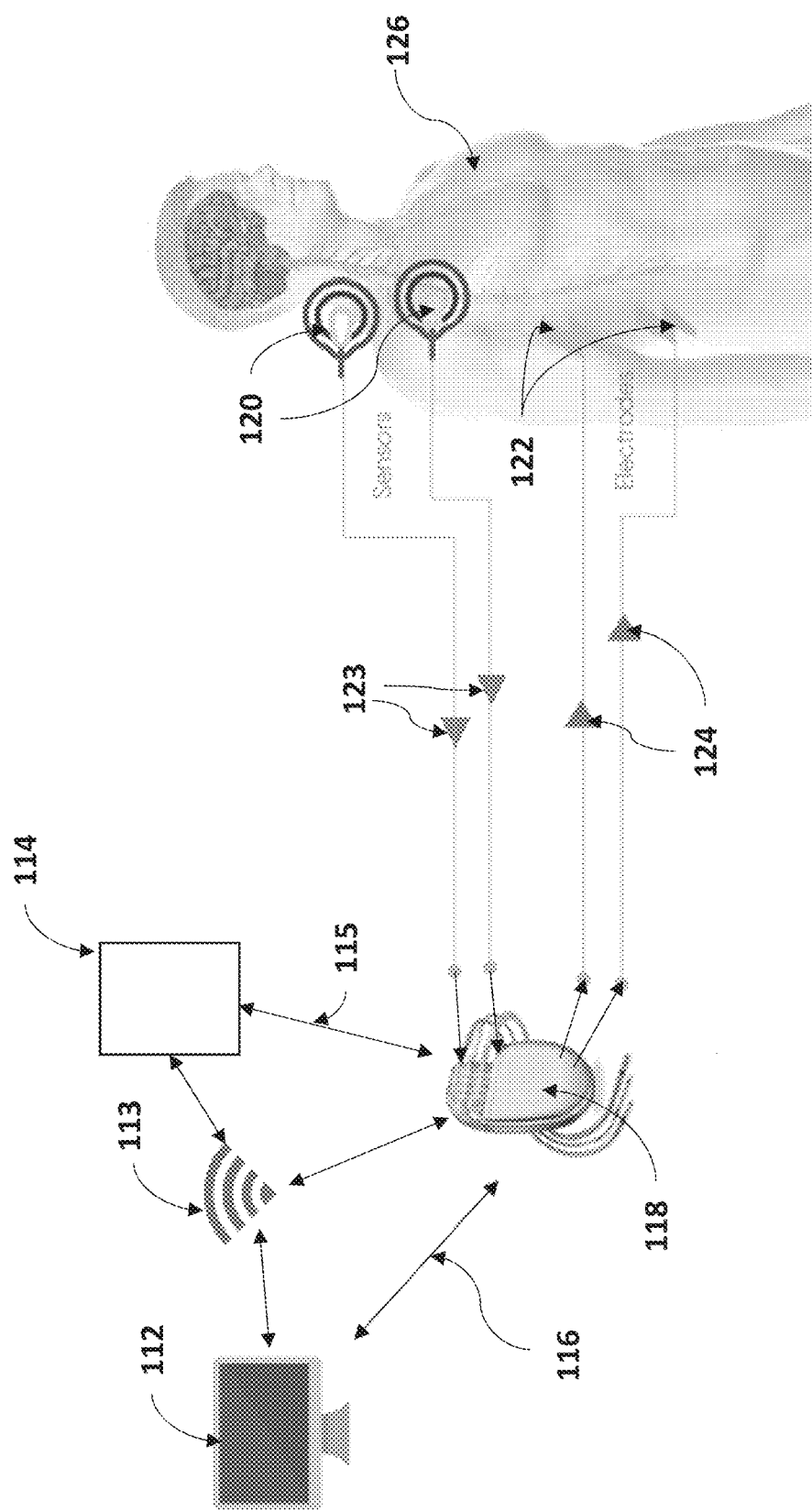
FIG. 2 shows an exemplary embodiment of a closed-loop bioelectronic system comprising a two-way neural interface comprising a sensor electrode that captures the neural response of the subject and a processing module that can interpret the neural response. The system is capable of delivering an adapted stimulation based on the neural response.

FIG. 2 shows a closed loop configuration of the device described herein configured to prevent an episode of incontinence for an individual 126. The device in a closed loop configuration may comprise an implantable pulse generator 118, one or more stimulator electrodes 122, one or more sensor electrodes 120, and a power source. In some cases, the implantable pulse generator 118 may comprise a processor, and a wireless transmission module configured to execute software to detect, analyze myoelectric electromyograph (EMG) signals via one or more sensor electrodes 120 and administer an electrical stimulation pattern 124. In some instances, the power source may comprise a battery. The battery may be rechargeable or single use. In some cases, the battery may be charged through inductive charging. In some instances, the device configured in a closed loop configuration may measure EMG signals via one or more sensor electrodes 120 to detect the onset of a stress incontinence event or a level of innate myoelectric electrical activity. In some instances the device configured in a closed loop configuration may measure inertial signals such as rapid acceleration, shock, posture-orientation, or any combination thereof via the one or more sensor electrodes 120 to detect the onset of a stress incontinence event or a level of innate myoelectric electrical activity. In some cases, the stress incontinence event may comprise actions such as coughing, sneezing, laughing, or exercise. Once detected the implantable pulse generator 118 may provide an electrical stimulation pattern 124 to prevent micturition or uncontrolled defecation. In some cases, the threshold level for detecting a stress incontinence event may be modified and adjusted by the individual 126 via graphical user interface on an external input device 114 either via wireless communication 113 or a wired connection 115.

Figure 9:
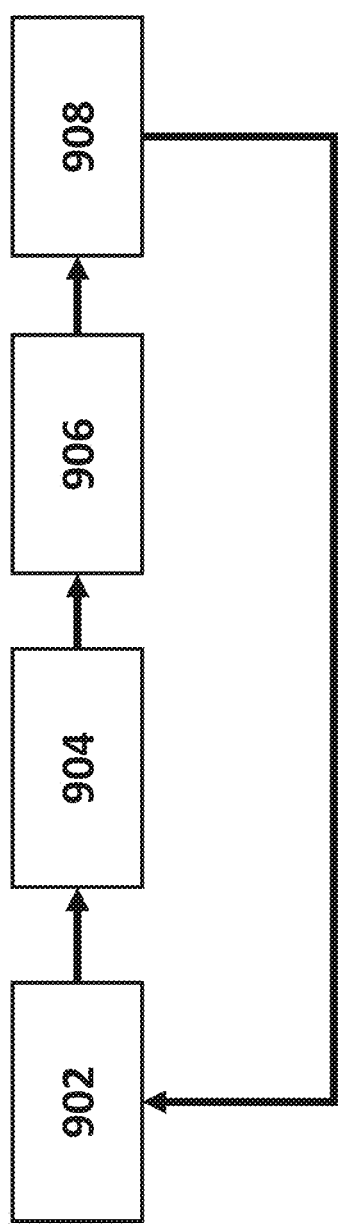
FIG. 9 shows a flow diagram for the closed loop system operation, as described in some embodiments herein.

In some embodiments, a closed-loop configuration of the systems and methods described herein, may comprise a fully synchronized system, as shown in FIG. 9. In some cases, an electrode 902, comprising a sensor and/or stimulator electrode may detect an EMG, ENG, and/or pressure signal through circuitry 904 (e.g., analog to digital circuitry) and then may pass the detected signal to a classifier algorithm 906. Once the classifier algorithm 906 has classified the detected EMG, ENG, and/or pressure signal as an incontinent event, the classifier may enable an electric stimulation 908 to be delivered to the patient. As shown in FIG. 9, the electrical stimulation may be provided by the same electrode 902 that sensed the EMG and/or ENG signal initially.

In some embodiments, a closed loop configuration of the device described herein may be configured to detect an individual's effort in trying to prevent an episode of incontinence. In some instances, the methods and systems described here may supplement the patient's effort with an electrical stimulation pattern via one or more stimulator electrodes 122 sufficient to prevent urinary or fecal defecation. In some cases, an individual's effort may comprise an EMG, ENG, pressure, acceleration, gyroscope, magnetometer, 3-D spatial, or any combination thereof signal at a threshold. In some instances, the threshold myoelectric signal may be detected by one or more sensor electrodes 120. In some cases, the supplemental excitation, may comprise an excitation signal provided by the stimulator electrodes, described elsewhere herein, with parameters e.g., frequency, pulse width, and/or amplitude such that in combination with the detected individual's effort may prevent an episode of incontinence (e.g., urinary, and/or fecal defecation). In some instances, the supplemental excitation may comprise an excitation signal provided by the stimulator electrodes with parameters e.g., frequency, pulse width, and/or amplitude to prevent an episode of incontinence in response to detecting a stress incontinence event. In some instances, the stress incontinence event may comprise actions such as coughing, sneezing, laughing, or exercise, detectable by e.g., a gyroscope, accelerometer, and/or magnetometer, described elsewhere herein. In some instances the one or more parameters of the supplemental excitation, may be determined on an individual subject basis and/or on a large-scale population of subjects with similar presentation of incontinence. For example, a given subject's supplemental excitation one or more parameters may be tuned and/or determined by whether such supplemental excitation signal prevented an episode of incontinence in real-time or after the incontinent event through a user interface of the device and systems, described elsewhere herein. In some instances, a given subject's supplemental excitation one or more parameters may be tuned to values and/or parameters found to prevent incontinence events in subjects with similar clinical presentation (e.g., age, type of incontinence, frequency of incontinence events, other subject clinical meta data, etc.).

Figure 8:
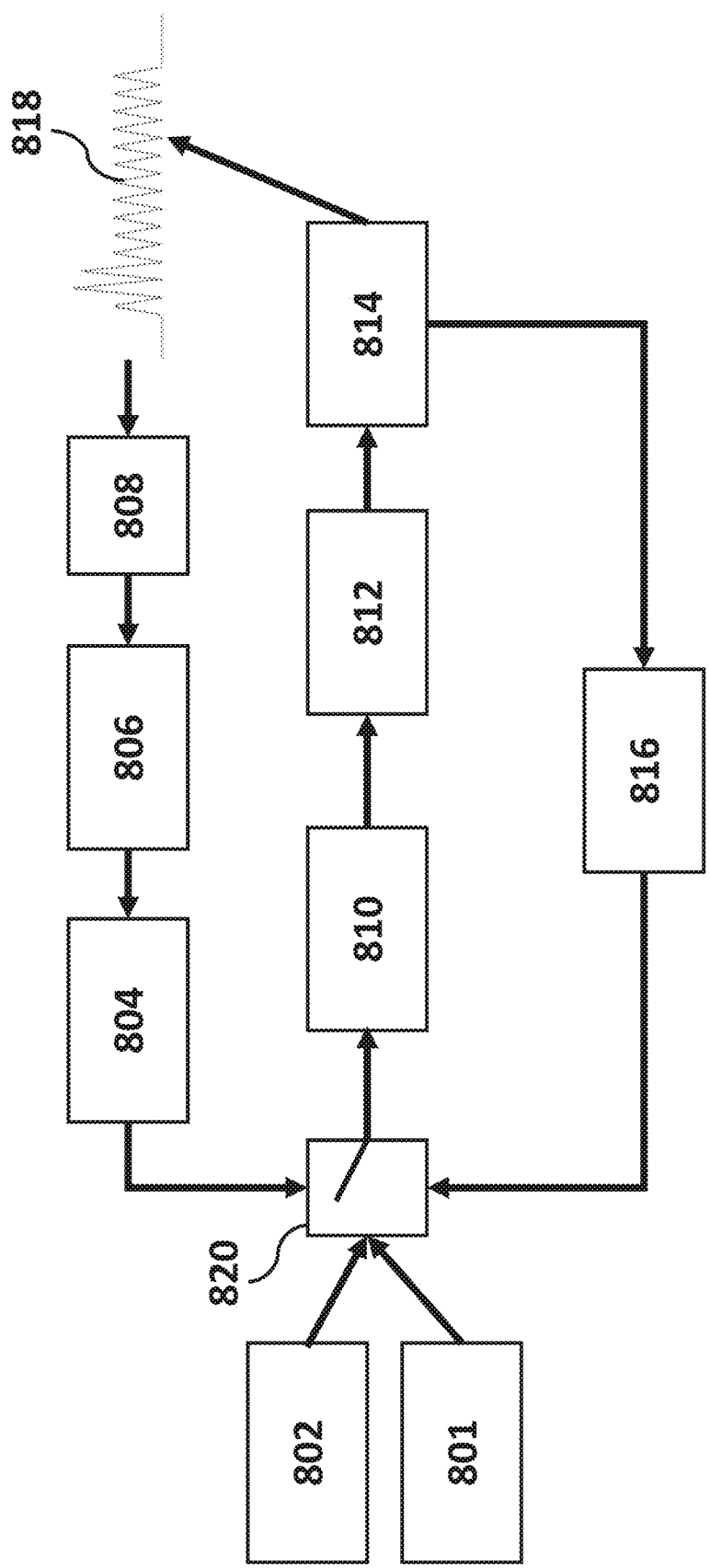
FIG. 8 shows a flow diagram for purposeful patient contraction and manual operation of the devices and systems, as described in some embodiments herein.

In some instances, the system and methods described herein may comprise system and methods configured to provide an electrical stimulation to prevent an incontinent event based on a subject and/or patient's purposeful muscle contraction and/or movement, as seen in FIG. 8. In some cases, the subject and/or patient 814 may, upon realizing that they may exhibit an incontinent event, induce movement and/or contraction of one or more muscles or muscle groups to trigger an EMG, ENG, pressure, acceleration, gyroscope, magnetometer, 3-D spatial, or any combination thereof signal 818. In some instances, the induced movement and/or contraction of one or more muscle groups may be amplified 808, classified (by a classifier) 806, passed through a control logic algorithm 804, and used as a trigger 820 to enable the flow of therapy and respective basal 802 and/or active 801, described elsewhere herein, stimulation pattern parameters through the stimulator 810 and neural interface 812 to prevent an incontinent event. In some cases, the classifier may comprise a machine learning classifier. In some instances, the classifier may comprise an intensity threshold classifier, described elsewhere herein. In some cases, the patient and/or subject 814 may manually 816 enable the delivery of electrical stimulation via a button on the patient controller module 156, described elsewhere herein.

In some cases, the detection threshold of the implantable pulse generator 118 (i.e., stimulator) may be modified and tuned via a graphical user interface on an external input device 114. The external input device 114 may be able to modify and tune the threshold of the implantable pulse generator 118 via a wireless communication 113 or a wired connection 115. In some cases, the implantable pulse generator threshold may be tuned via a healthcare provider on a remote computing device 112 (e.g., a mobile phone, a tablet, a computer, etc.) and transmitted via a wired communication 116 to the implantable pulse generator 118. Alternatively, the implantable pulse generator threshold may be tuned via a healthcare provider on a remote computing device 112 (e.g., a mobile phone, a tablet, a computer, etc.) and transmitted via wireless communication 113 to the implantable pulse generator 118. In some cases, the implantable pulse generator threshold may be tuned via the individual 110 on a remote computing device 112 (e.g., a mobile phone, a tablet, a computer, etc.) and transmitted via a wired communication 116 to the implantable pulse generator 118. Alternatively, the implantable pulse generator threshold may be tuned via the individual 110 on a remote computing device 112 (e.g., a mobile phone, a tablet, a computer, etc.) and transmitted via wireless communication 113 to the implantable pulse generator 118.

In some cases, the electrical stimulation pattern 124 provided via one or more stimulator electrodes 122 may be tuned and adjusted by the detected threshold level to supplement an individual's effort to prevent an episode of incontinence. In some instances, the adjusted electrical stimulation pattern 124 may be determined by mapping a detectable physiological signal representing effort and a provided electrical stimulation pattern 124 by, piecewise linear mapping, linear mapping, sigmoidal mapping, or any variations thereof. The electric stimulation pattern 124 may be tuned by modifying or changing the electrical stimulation pattern parameters comprising frequency, pulse-width, and amplitude. In some cases, the electrical stimulation pattern parameters of the implantable pulse generator 118 may be modified and tuned via a graphical user interface on an external input device 114. The external input device 114 may be able to modify and tune the electrical stimulation pattern parameters of implantable pulse generator 118 via a wireless communication 113 or a wired connection 115. In some cases, the electrical stimulation pattern parameters of implantable pulse generator 118 may be tuned via a healthcare provider on a remote computing device 112 (e.g., a mobile phone, a tablet, a computer, etc.) and transmitted via a wired communication 116 to the implantable pulse generator 118. In some cases, the electrical stimulation pattern parameters of implantable pulse generator 118 may be tuned via a healthcare provider on a remote computing device 112 (e.g., a mobile phone, a tablet, a computer, etc.) and transmitted via wireless communication 113 to the implantable pulse generator 118. In some cases, the electrical stimulation pattern parameters of implantable pulse generator 118 may be tuned by a machine learning model executed by the processor of the implantable pulse generator 118 based on input from the individual 126. In some cases, the machine learning model may be configured to determine a whether or not a subject is at risk of unwanted micturition and/or fecal defecation based on muscle EMG signals detected by the one or more sensor electrodes. In some cases, the machine learning model may be trained to determine the presence or lack thereof an individual's effort, described elsewhere herein. For example, the machine learning model may be trained with one or more EMG signals characteristic of a subject's muscle contractions in particular EMG signals that lead to unwanted micturition and/or fecal defecation.

In some embodiments, the electrical stimulation pattern parameters, as described elsewhere herein (e.g., frequency, amplitude, etc.), may be set or determined by a stimulation machine learning model. In some cases, the stimulation machine learning model may comprise a Bayesian optimization model. In some instances, the stimulation machine learning model may be trained with stimulation patterns that users of the devices and systems, described elsewhere herein, indicate as inhibiting incontinent events for particular types and/or subtypes of incontinence. In some cases, the stimulation machine learning model may be trained with the patient's type of incontinence. The stimulation machine learning algorithms may be trained in a cloud computing network and/or server in communication with the implantable and user-devices, described elsewhere herein, and re-distributed or downloaded to one or more users and/or patients. In effect users and/or patients may update and/or download new updates to the software of the devices and systems described herein. This aspect of the invention described herein provides an unexpected result of a patient specific and optimized electrical stimulation signal that would otherwise not be achievable with a traditional stimulator.

One or more machine learning algorithms may be used to construct the machine learning model, such as support vector machines that deploy stepwise backwards parameter selection and/or graphical models, both of which may have advantages of inferring interactions between parameters. For example, machine learning algorithms or other statistical algorithms may be used such as alternating decision trees (ADTree), decision stumps, functional trees (FT), logistic model trees (LMT), logistic regression, random forests (rf), receiver operational characteristic curves (ROC), linear regression, extreme gradient boosting (xgb), classification and regression trees, support vector machines (SVM), generalized additive model using splines (e.g., gamSpline), glmnet, multivariate adaptive regression splint (earth), neural network, k-means clustering, or any machine learning algorithm or statistical algorithm known in the art. One or more algorithms may be used together to generate an ensemble method, wherein the ensemble method may be optimized using a machine learning ensemble meta-algorithm such as boosting (e.g., AdaBoost, LPBoost, TotalBoost, BrownBoost, MadaBoost, LogitBoost, etc.) to reduce bias and/or variance.

In some embodiments, the machine learning algorithm may comprise a constrained machine learning algorithm configured to run on micro-processors. In some cases, the machine learning algorithm may comprise a machine learning algorithm operating on within a TinyML framework. In some instances, the machine learning algorithm, described elsewhere herein may be trained offline. The offline training may be completed on a server, cloud, or other dedicated computing clusters. In some cases, the offline trained machine learning algorithm could then be downloaded, deployed, and/or imported into the device to iteratively improve upon the device and system performance in preventing incontinent events.

One of ordinary skill would realize that such an off-line training structure is feasible and realized in related but different implementation. For example, such a machine learning architecture may be utilized in performing "wake up-word" text classification that are commonly seen in smartphone devices (e.g., "hey siri", "okay google", etc.). In some cases, the machine learning algorithms described herein may operate within a framework similar to the "wake up-words" speech machine learning classifier. In some cases, the machine learning algorithms described herein may operate on processing power and memory allocation determined to be sufficient for "wake up" speech machine learning classifiers.

In some cases, the software, described elsewhere herein, may be executed by a processor located on the implanted stimulator. In some cases, the software located on the implanted stimulator may utilize a TinyML constrained machine learning model to accommodate the processing and memory parameters of the implanted stimulator. In some instances, the software may be executed offline on a cloud based computing and/or dedicated computing cluster(s). In some cases, the offline processing workflow may include a high-speed (Bluetooth, Wi-Fi, medical implant communication systems, etc.) data transfer between the implanted stimulator and a local personal computing device (smartphone, tablet, laptop, etc.). The personal processing device may then communicate the implanted stimulator data to a one or more cloud and/or computer clusters that will then send back a resulting output, command, and/or notification to the device. In some cases, the command and/or notification may comprise a warning, alert, initiation of electrical stimulation, or any combination thereof. In some cases, the command may comprise the output of a machine learning classifier configured to determine a threshold intensity of EMG and/or ENG signals indicative of an incontinence event.

Figure 13:
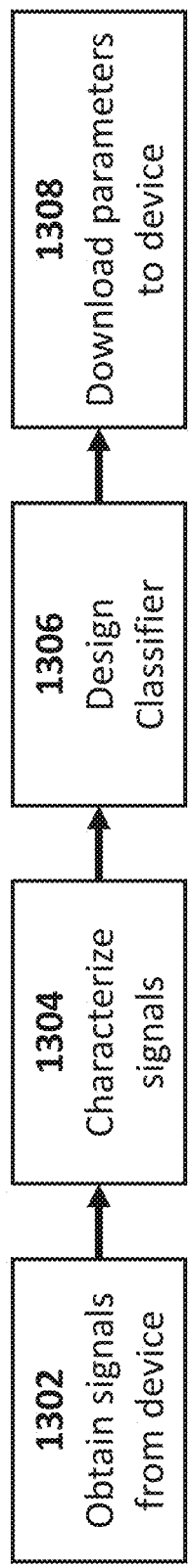
FIG. 13 shows a flow diagram for training on-board machine learning classifier of the devices and systems of the disclosure, as described in some embodiments herein.

The machine learning models may be trained on one or more datasets. In some instances, the one or more datasets may comprise data generated by a user and/or subject, or data generated by a population or segment thereof. In some cases, the data generated by subject and/or the data generated by a population may comprise effort signals, excitation signals, that indicated an incontinent event, and prevented an incontinent event, respectively. In some cases, the devices, systems, and corresponding methods described herein, may record user data and/or input of the user when interacting with the systems and devices described elsewhere herein. In some cases, the data may comprise user labeled EMG, ENG, accelerometer, gyroscope, or any combination thereof sensors, as described elsewhere herein, that lead to an incontinent event. In some cases, these signals may be obtained from the device 1302, and used in characterizing 1304 and training a machine learning classifier 1306, as seen in FIG. 13. In some instances, the trained machine learning classifiers trained on or more datasets may then be downloaded to each patient's device 1308 to further improve the machine learning classifier's accuracy. In some cases, the machine learning models may be configured to sense subject effort and/or providing sufficient excitation based on e.g., parameters of frequency, amplitude, and/or pulse-width as described elsewhere herein. In some instances, the datasets of one or more individuals may be pooled together as a training dataset where the subjects show characteristics of similarity between clinical presentation and parameters of excitatory/sensory input. In some cases, clinical presentation may comprise clinical incontinence type, subject clinical meta data, e.g., gender, age, past medical history, current medications taken, past surgical intervention, etc. In some cases, a pooled training datasets may be utilized for an individual during the initial period of training a device implanted into a subject.

In some cases, the one or more machine learning models, described elsewhere herein, may be trained on raw and/or processed signals measured by the devices, sensors, and systems, described elsewhere herein. In some cases, the processed signals may comprise original raw signals that have been filtered to optimize the signal-to-noise ratio of the raw signal. In some cases, the filter may comprise a high-pass, low-pass, band-pass, notch, or any combination thereof filters. In some instances, the one or more machine learning models may alternatively or in addition to, be trained on user feedback regarding prior excitation signal parameters and whether or not such excitation signal parameters prevented an incontinent event.

Figure 10:
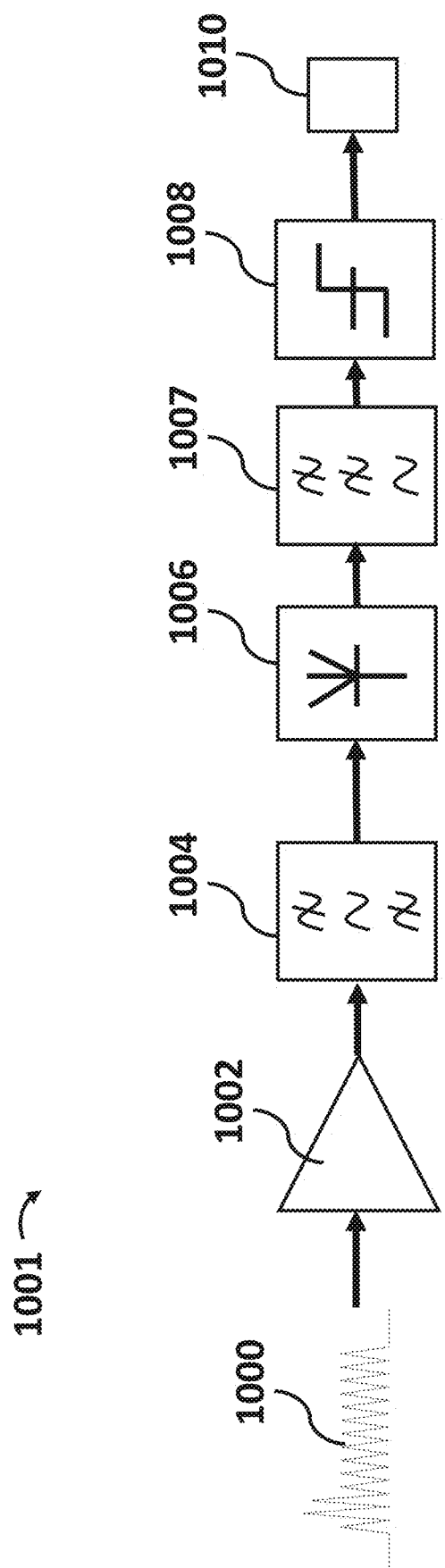
FIG. 10 shows a flow diagram for signal processing and threshold detection of incontinent events, as described in some embodiments herein.

In some aspects, the disclosure provides a method of processing detected signals 1001, described elsewhere herein to determine incontinent event precursor signal intensity thresholds, as seen in FIG. 10. In some cases, the EMG, ENG, accelerometer, gyroscope, magnetometer, pressure sensor signals, or any combination thereof signals 1000 may be detected through an amplifier circuit 1002. In some cases, the amplifier circuit may comprise an operational amplifier circuit.

In some instances, the amplifier circuit may be configured to amplify signals from about 10 microvolt ($\mu V$) to about 1,000 $\mu V$. In some instances, the amplifier circuit may be configured to amplify signals from about 10$\mu$ V to about 50$\mu$, about 10$\mu$ V to about 100$\mu$, about 10$\mu$ V to about 150$\mu$, about 10$\mu$ V to about 300$\mu$, about 10$\mu$ V to about 500$\mu$, about 10$\mu$ V to about 700 $\mu V$, about 10 $\mu V$ to about 900 $\mu V$, about 10 $\mu V$ to about 1,000 $\mu V$, about 50 $\mu V$ to about 100$\mu$, about 50$\mu$ V to about 150$\mu$, about 50$\mu$ V to about 300$\mu$, about 50$\mu$ V to about 500$\mu$ V, about 50$\mu$ V to about 700$\mu$, about 50$\mu$ V to about 900$\mu$, about 50$\mu$ V to about 1,000$\mu$, about 100$\mu$ V to about 150$\mu$, about 100$\mu$ V to about 300$\mu$, about 100$\mu$ V to about 500$\mu$, about 100$\mu$ V to about 700$\mu$, about 100$\mu$ V to about 900$\mu$, about 100$\mu$ V to about 1,000$\mu$, about 150$\mu$ V to about 300$\mu$, about 150$\mu$ V to about 500$\mu$, about 150$\mu$ V to about 700$\mu$, about 150$\mu$ V to about 900 $\mu V$, about 150 $\mu V$ to about 1,000 $\mu V$, about 300 $\mu V$ to about 500 $\mu V$, about 300 $\mu V$ to about 700$\mu$, about 300$\mu$ V to about 900$\mu$, about 300$\mu$ V to about 1,000$\mu$, about 500$\mu$ V to about 700$\mu$, about 500$\mu$ V to about 900$\mu$, about 500$\mu$ V to about 1,000$\mu$, about 700$\mu$ V to about 900$\mu$, about 700$\mu$ V to about 1,000$\mu$, or about 900$\mu$ V to about 1,000$\mu$. In some instances, the amplifier circuit may be configured to amplify signals from about 10 $\mu V$, about 50$\mu$, about 100$\mu$, about 150$\mu$, about 300$\mu$, about 500$\mu$, about 700$\mu$, about 900$\mu$, or about 1,000 $\mu V$. In some instances, the amplifier circuit may be configured to amplify signals from at least about 10 $\mu V$, about 50 $\mu V$, about 100 $\mu V$, about 150 $\mu V$, about 300 $\mu V$, about 500 $\mu V$, about 700 $\mu V$, or about 900 $\mu V$. In some instances, the amplifier circuit may be configured to amplify signals from at most about 50 $\mu V$, about 100 $\mu V$, about 150 $\mu V$, about 300 $\mu V$, about 500 $\mu V$, about 700 $\mu V$, about 900 $\mu V$, or about 1,000 $\mu V$.

In some cases, the amplifier circuit may be configured to amplify signals with a frequency of about 1 Hz to about 1,500 Hz. In some cases, the amplifier circuit may be configured to amplify signals with a frequency of about 1 Hz to about 20 Hz, about 1 Hz to about 40 Hz, about 1 Hz to about 80 Hz, about 1 Hz to about 100 Hz, about 1 Hz to about 150 Hz, about 1 Hz to about 200 Hz, about 1 Hz to about 250 Hz, about 1 Hz to about 500 Hz, about 1 Hz to about 750 Hz, about 1 Hz to about 1,000 Hz, about 1 Hz to about 1,500 Hz, about 20 Hz to about 40 Hz, about 20 Hz to about 80 Hz, about 20 Hz to about 100 Hz, about 20 Hz to about 150 Hz, about 20 Hz to about 200 Hz, about 20 Hz to about 250 Hz, about 20 Hz to about 500 Hz, about 20 Hz to about 750 Hz, about 20 Hz to about 1,000 Hz, about 20 Hz to about 1,500 Hz, about 40 Hz to about 80 Hz, about 40 Hz to about 100 Hz, about 40 Hz to about 150 Hz, about 40 Hz to about 200 Hz, about 40 Hz to about 250 Hz, about 40 Hz to about 500 Hz, about 40 Hz to about 750 Hz, about 40 Hz to about 1,000 Hz, about 40 Hz to about 1,500 Hz, about 80 Hz to about 100 Hz, about 80 Hz to about 150 Hz, about 80 Hz to about 200 Hz, about 80 Hz to about 250 Hz, about 80 Hz to about 500 Hz, about 80 Hz to about 750 Hz, about 80 Hz to about 1,000 Hz, about 80 Hz to about 1,500 Hz, about 100 Hz to about 150 Hz, about 100 Hz to about 200 Hz, about 100 Hz to about 250 Hz, about 100 Hz to about 500 Hz, about 100 Hz to about 750 Hz, about 100 Hz to about 1,000 Hz, about 100 Hz to about 1,500 Hz, about 150 Hz to about 200 Hz, about 150 Hz to about 250 Hz, about 150 Hz to about 500 Hz, about 150 Hz to about 750 Hz, about 150 Hz to about 1,000 Hz, about 150 Hz to about 1,500 Hz, about 200 Hz to about 250 Hz, about 200 Hz to about 500 Hz, about 200 Hz to about 750 Hz, about 200 Hz to about 1,000 Hz, about 200 Hz to about 1,500 Hz, about 250 Hz to about 500 Hz, about 250 Hz to about 750 Hz, about 250 Hz to about 1,000 Hz, about 250 Hz to about 1,500 Hz, about 500 Hz to about 750 Hz, about 500 Hz to about 1,000 Hz, about 500 Hz to about 1,500 Hz, about 750 Hz to about 1,000 Hz, about 750 Hz to about 1,500 Hz, or about 1,000 Hz to about 1,500 Hz. In some cases, the amplifier circuit may be configured to amplify signals with a frequency of about 1 Hz, about 20 Hz, about 40 Hz, about 80 Hz, about 100 Hz, about 150 Hz, about 200 Hz, about 250 Hz, about 500 Hz, about 750 Hz, about 1,000 Hz, or about 1,500 Hz. In some cases, the amplifier circuit may be configured to amplify signals with a frequency of at least about 1 Hz, about 20 Hz, about 40 Hz, about 80 Hz, about 100 Hz, about 150 Hz, about 200 Hz, about 250 Hz, about 500 Hz, about 750 Hz, or about 1,000 Hz. In some cases, the amplifier circuit may be configured to amplify signals with a frequency of at most about 20 Hz, about 40 Hz, about 80 Hz, about 100 Hz, about 150 Hz, about 200 Hz, about 250 Hz, about 500 Hz, about 750 Hz, about 1,000 Hz, or about 1,500 Hz.

In some cases, the amplified signal may then be passed to a filter 1004. In some cases, the filter may comprise a low-pass, high-pass, band-pass, notch, or any combination thereof filter.

In some cases, the filter may be configured to filter the frequency band of about 1 Hz to about 70 Hz. In some cases, the filter may be configured to filter the frequency band of about 1 Hz to about 5 Hz, about 1 Hz to about 10 Hz, about 1 Hz to about 15 Hz, about 1 Hz to about 20 Hz, about 1 Hz to about 25 Hz, about 1 Hz to about 40 Hz, about 1 Hz to about 50 Hz, about 1 Hz to about 60 Hz, about 1 Hz to about 70 Hz, about 5 Hz to about 10 Hz, about 5 Hz to about 15 Hz, about 5 Hz to about 20 Hz, about 5 Hz to about 25 Hz, about 5 Hz to about 40 Hz, about 5 Hz to about 50 Hz, about 5 Hz to about 60 Hz, about 5 Hz to about 70 Hz, about 10 Hz to about 15 Hz, about 10 Hz to about 20 Hz, about 10 Hz to about 25 Hz, about 10 Hz to about 40 Hz, about 10 Hz to about 50 Hz, about 10 Hz to about 60 Hz, about 10 Hz to about 70 Hz, about 15 Hz to about 20 Hz, about 15 Hz to about 25 Hz, about 15 Hz to about 40 Hz, about 15 Hz to about 50 Hz, about 15 Hz to about 60 Hz, about 15 Hz to about 70 Hz, about 20 Hz to about 25 Hz, about 20 Hz to about 40 Hz, about 20 Hz to about 50 Hz, about 20 Hz to about 60 Hz, about 20 Hz to about 70 Hz, about 25 Hz to about 40 Hz, about 25 Hz to about 50 Hz, about 25 Hz to about 60 Hz, about 25 Hz to about 70 Hz, about 40 Hz to about 50 Hz, about 40 Hz to about 60 Hz, about 40 Hz to about 70 Hz, about 50 Hz to about 60 Hz, about 50 Hz to about 70 Hz, or about 60 Hz to about 70 Hz. In some cases, the filter may be configured to filter the frequency band of about 1 Hz, about 5 Hz, about 10 Hz, about 15 Hz, about 20 Hz, about 25 Hz, about 40 Hz, about 50 Hz, about 60 Hz, or about 70 Hz. In some cases, the filter may be configured to filter the frequency band of at least about 1 Hz, about 5 Hz, about 10 Hz, about 15 Hz, about 20 Hz, about 25 Hz, about 40 Hz, about 50 Hz, or about 60 Hz. In some cases, the filter may be configured to filter the frequency band of at most about 5 Hz, about 10 Hz, about 15 Hz, about 20 Hz, about 25 Hz, about 40 Hz, about 50 Hz, about 60 Hz, or about 70 Hz.

After passing the signal through the filter, the systems and methods described herein, may rectify 1006 the filtered signal. In the process of rectifying the signal, as understood by one of ordinary skill in the art, the signal will convert the alternating current detected signal to a direct current signal. The rectified signal may be additionally filtered with a low pass filter 1007 that may smooth the rectified signal. The signal may be subjected to a threshold detector 1008, where the threshold detector determines the onset of an incontinent event from a threshold intensity value of the rectified and smooth processed signals 1000 of EMG, ENG, accelerometer, gyroscope, magnetometer, pressure sensor signals, or any combination thereof. If an incontinent event is determined by the threshold detector 1008, the system may enable the delivery of electrical stimulation 1010, as described elsewhere herein.

In some cases, training may be supervised training. Alternatively, training may be unsupervised training. In some instances, the data set may be a retrospective data set. Alternatively, the data set may be prospectively developed dataset, and the machine learning model may be iteratively improved over time.

In some aspects, the disclosure provided herein may comprise a method to train a machine learning model with a data set that comprises sensed signal profiles and excitation signals that have and have not prevented incontinent events. The method may comprise the steps of: preprocessing, training, and predicting.

The method may extract training data from a database, or intake new data, described elsewhere herein. The preprocessing step may apply one or more transformations to standardize the training data or new data for the training step or the prediction step. The preprocessed training data may be passed to the training step, which may construct a machine learning model based on training data. The training step may further comprise a validation step, configured to validate the trained machine learning model using any appropriate validation algorithm (e.g., Stratified K-fold cross-validation). In some cases, the k-fold cross-validation may comprise at least 1-fold, 2, folds, 3 folds, 4 folds, 5 folds, 6 folds, 7 folds, 8 folds, 9 folds, or 10 folds. In some cases, the k-fold cross-validation may comprise up to 1-fold, 2 folds, 3 folds, 4 folds, 5 folds, 6 folds, 7 folds, 8 folds, 9 folds, or 10 folds.

The preprocessing step may apply one or more transformations to the training data to clean and normalize the data. The preprocessing step may be configured to discard parameters which contain spurious data or contain very few observations. The preprocessing module can be further configured to standardize the encoding of parameter values. The preprocessing step may recognize the encoding variation for the same value and standardize the dataset to have a uniform encoding for a given parameter value. The processing step may thus reduce irregularities in the input data for the training and prediction steps, thereby improving the robustness of the training and prediction steps.

The training step may utilize a machine learning algorithm or other algorithm to construct and train a machine learning model to be used in the association of an excitation stimulation, sensed signal profile, and the presence or lack thereof an incontinent event. A machine learning model may be constructed to capture, based on the training data, the statistical relationship, if any, between excitation stimulation parameters, sensed signal profiles, and the presence or lack thereof an incontinent event.

The machine learning algorithm may have an accuracy greater than about 60%, 70%, 80%, 85%, 90%, 95%, or 99%. The machine learning algorithm may have a positive predictive value greater than about 60%, 70%, 75%, 80%, 85%, 90%, 95%, or 99%. The machine learning algorithm may have a negative predictive value greater than about 60%, 70%, 80%, 90%, 95%, or 99%.

Machine learning data analysis, machine learning model training, or any combination thereof may be performed using one or more of many programming languages and platforms known in the art, such as R, Weka, Python, and/or MATLAB, for example.

The use of such closed-loop bioelectronic systems may potentially provide improved electrical stimulation devices to prevent or reduce stress incontinence. In some cases, the use of such closed-loop bioelectronic systems may provide a more precise approach to prevent or reduce or treat urge incontinence and mixed incontinence (combination of urge and stress incontinence). In some instances, individuals having the implanted device may provide feedback to the parameters provided positive outcomes, negative outcomes, or neutral outcomes. In some cases, positive outcomes may comprise preventing an incontinence event. In some instances, negative outcomes may comprise not preventing an incontinence event, producing pain, or any combination thereof. In some cases, neutral outcomes may comprise not preventing an incontinence event, not producing pain, or any combination thereof. In some cases, the positive outcomes, negative outcomes, neutral outcomes, sensor data, or any combination thereof from a plurality of individuals having the implanted device may be used in tuning algorithms to suggest changes to sensor electrode thresholds and electrical stimulation patterns 124.

Electrical Simulation Pattern

In some cases, the electric stimulation pattern provided by an implantable pulse generator and one or more stimulator electrodes may be modified or changed to suit the needs of the individual in need thereof preventing an episode of incontinence. In some cases, the one or more stimulator electrodes 122 may output an electric stimulation pattern 124 in response to what is detected by the one or more sensor electrodes 120. In some cases, the electric stimulation pattern 124 may comprise one or more electrical signals. For example, the electric stimulation pattern 124 may comprise a continuous wave signal (e.g., an electric stimulation signal with a constant frequency in time) and a burst or beating signal superimposed onto the continuous wave signal. In some cases, the burst or beating signal may only be enabled for a short duration of time compared to the continual temporal aspect of the continuous wave signal. In some instances, the combination of the continuous wave signal and/or a burst or beating signal may increase a pain threshold of a subject allowing the stimulator to provide higher amplitude electric stimulation burst pattern to prevent incontinent events. In some instances, the frequency of the electric stimulation pattern may be modified or changed. The frequency pattern may comprise a constant profile, swept profile, beating profile, burst profile, chirped profile, monophasic profile, biphasic profile, or any combination thereof. In some instances, the constant profile is comprised of excitation values at a constant amplitude with a frequency value of 0 Hz. In some cases, a swept profile may comprise a signal with time varying frequency of excitation. In some instances, a beating profile may comprise a combination of one or more excitation signals of varying frequency. In some cases, the burst profile may comprise a signal with a constant frequency that is enveloped by a square, delta, sine, or any combination thereof envelope functions. In some instances, a monophasic profile may comprise an excitation signal with only positive or negative amplitude (e.g., signal with values from 0 to −5V or 0 to 5V only) with a constant frequency. In some cases, the beating or burst profile may comprise an electric simulation pattern that is provided to a patient and/or subject for during an on-state for a first period of time and is not provided to a patient and/or subject during an off-state for a second period of time. In some cases, beating or bust profiles may provide an excitation signal that may provide for a lengthier period of muscle excitation without suffering muscle fatigue. In some cases, the on-state and/or off-state may comprise about 0.1 second(s) to about 6.5 s. In some cases, the on-state and/or off-state may comprise about 0.1 s to about 0.5 s, about 0.1 s to about 1 s, about 0.1 s to about 1.2 s, about 0.1 s to about 1.5 s, about 0.1 s to about 2 s, about 0.1 s to about 2.5 s, about 0.1 s to about 3 s, about 0.1 s to about 3.5 s, about 0.1 s to about 4 s, about 0.1 s to about 5 s, about 0.1 s to about 6.5 s, about 0.5 s to about 1 s, about 0.5 s to about 1.2 s, about 0.5 s to about 1.5 s, about 0.5 s to about 2 s, about 0.5 s to about 2.5 s, about 0.5 s to about 3 s, about 0.5 s to about 3.5 s, about 0.5 s to about 4 s, about 0.5 s to about 5 s, about 0.5 s to about 6.5 s, about 1 s to about 1.2 s, about 1 s to about 1.5 s, about 1 s to about 2 s, about 1 s to about 2.5 s, about 1 s to about 3 s, about 1 s to about 3.5 s, about 1 s to about 4 s, about 1 s to about 5 s, about 1 s to about 6.5 s, about 1.2 s to about 1.5 s, about 1.2 s to about 2 s, about 1.2 s to about 2.5 s, about 1.2 s to about 3 s, about 1.2 s to about 3.5 s, about 1.2 s to about 4 s, about 1.2 s to about 5 s, about 1.2 s to about 6.5 s, about 1.5 s to about 2 s, about 1.5 s to about 2.5 s, about 1.5 s to about 3 s, about 1.5 s to about 3.5 s, about 1.5 s to about 4 s, about 1.5 s to about 5 s, about 1.5 s to about 6.5 s, about 2 s to about 2.5 s, about 2 s to about 3 s, about 2 s to about 3.5 s, about 2 s to about 4 s, about 2 s to about 5 s, about 2 s to about 6.5 s, about 2.5 s to about 3 s, about 2.5 s to about 3.5 s, about 2.5 s to about 4 s, about 2.5 s to about 5 s, about 2.5 s to about 6.5 s, about 3 s to about 3.5 s, about 3 s to about 4 s, about 3 s to about 5 s, about 3 s to about 6.5 s, about 3.5 s to about 4 s, about 3.5 s to about 5 s, about 3.5 s to about 6.5 s, about 4 s to about 5 s, about 4 s to about 6.5 s, or about 5 s to about 6.5 s. In some cases, the on-state and/or off-state may comprise about 0.1 s, about 0.5 s, about 1 s, about 1.2 s, about 1.5 s, about 2 s, about 2.5 s, about 3 s, about 3.5 s, about 4 s, about 5 s, or about 6.5 s. In some cases, the on-state and/or off-state may comprise at least about 0.1 s, about 0.5 s, about 1 s, about 1.2 s, about 1.5 s, about 2 s, about 2.5 s, about 3 s, about 3.5 s, about 4 s, or about 5 s. In some cases, the on-state and/or off-state may comprise at most about 0.5 s, about 1 s, about 1.2 s, about 1.5 s, about 2 s, about 2.5 s, about 3 s, about 3.5 s, about 4 s, about 5 s, or about 6.5 s.

In some instances, an electrical stimulation pattern provided during an on-state may comprise an oscillating electric stimulation pattern. In some cases, the oscillating electric stimulation pattern may comprise one or more frequencies. In some cases, the frequency of the oscillating electrical stimulation may be chosen based upon prior knowledge of how similar subjects respond with a particular frequency or range of frequencies of the oscillating electrical stimulation pattern. In some cases, a low frequency (e.g., 2-15 Hz) may induces reductions in bladder contractility and thus prevent voiding or a potential incontinent event. In some instances, a higher frequency (e.g., 20-50 Hz) may lead to potentiation of bladder contractions and voiding. In some instances, the frequency of the electrical stimulation pattern may be about 1 Hz to about 60 Hz. In some instances, the frequency of the electrical stimulation pattern may be about 1 Hz to about 5 Hz, about 1 Hz to about 10 Hz, about 1 Hz to about 15 Hz, about 1 Hz to about 25 Hz, about 1 Hz to about 30 Hz, about 1 Hz to about 35 Hz, about 1 Hz to about 40 Hz, about 1 Hz to about 45 Hz, about 1 Hz to about 50 Hz, about 1 Hz to about 55 Hz, about 1 Hz to about 60 Hz, about 5 Hz to about 10 Hz, about 5 Hz to about 15 Hz, about 5 Hz to about 25 Hz, about 5 Hz to about 30 Hz, about 5 Hz to about 35 Hz, about 5 Hz to about 40 Hz, about 5 Hz to about 45 Hz, about 5 Hz to about 50 Hz, about 5 Hz to about 55 Hz, about 5 Hz to about 60 Hz, about 10 Hz to about 15 Hz, about 10 Hz to about 25 Hz, about 10 Hz to about 30 Hz, about 10 Hz to about 35 Hz, about 10 Hz to about 40 Hz, about 10 Hz to about 45 Hz, about 10 Hz to about 50 Hz, about 10 Hz to about 55 Hz, about 10 Hz to about 60 Hz, about 15 Hz to about 25 Hz, about 15 Hz to about 30 Hz, about 15 Hz to about 35 Hz, about 15 Hz to about 40 Hz, about 15 Hz to about 45 Hz, about 15 Hz to about 50 Hz, about 15 Hz to about 55 Hz, about 15 Hz to about 60 Hz, about 25 Hz to about 30 Hz, about 25 Hz to about 35 Hz, about 25 Hz to about 40 Hz, about 25 Hz to about 45 Hz, about 25 Hz to about 50 Hz, about 25 Hz to about 55 Hz, about 25 Hz to about 60 Hz, about 30 Hz to about 35 Hz, about 30 Hz to about 40 Hz, about 30 Hz to about 45 Hz, about 30 Hz to about 50 Hz, about 30 Hz to about 55 Hz, about 30 Hz to about 60 Hz, about 35 Hz to about 40 Hz, about 35 Hz to about 45 Hz, about 35 Hz to about 50 Hz, about 35 Hz to about 55 Hz, about 35 Hz to about 60 Hz, about 40 Hz to about 45 Hz, about 40 Hz to about 50 Hz, about 40 Hz to about 55 Hz, about 40 Hz to about 60 Hz, about 45 Hz to about 50 Hz, about 45 Hz to about 55 Hz, about 45 Hz to about 60 Hz, about 50 Hz to about 55 Hz, about 50 Hz to about 60 Hz, or about 55 Hz to about 60 Hz. In some instances, the frequency of the electrical stimulation pattern may be about 1 Hz, about 5 Hz, about 10 Hz, about 15 Hz, about 25 Hz, about 30 Hz, about 35 Hz, about 40 Hz, about 45 Hz, about 50 Hz, about 55 Hz, or about 60 Hz. In some instances, the frequency of the electrical stimulation pattern may be at least about 1 Hz, about 5 Hz, about 10 Hz, about 15 Hz, about 25 Hz, about 30 Hz, about 35 Hz, about 40 Hz, about 45 Hz, about 50 Hz, or about 55 Hz. In some instances, the frequency of the electrical stimulation pattern may be at most about 5 Hz, about 10 Hz, about 15 Hz, about 25 Hz, about 30 Hz, about 35 Hz, about 40 Hz, about 45 Hz, about 50 Hz, about 55 Hz, or about 60 Hz. In some embodiments, the frequency refers to mean frequency of the electrical stimulation pattern. In some embodiments, the frequency refers to the median frequency. In some embodiments, the frequency refers to the maximum frequency.

In some cases, a burst signal with an on-state and/or an off-state, described elsewhere herein may be provided to the subject to prevent fatigue on the one or more muscles innervated by the subject's pudendal nerve. In some cases, the burst electrical stimulation pattern may comprise one or more frequencies described elsewhere herein.

In some instances, the amplitude of the electric stimulation pattern may be modified or changed. In some instances, the amplitude of the electrical stimulation pattern may be about 1 volt (V) to about 15 V. In some instances, the amplitude of the electrical stimulation pattern may be about 1 V to about 2 V, about 1 V to about 3 V, about 1 V to about 4 V, about 1 V to about 5 V, about 1 V to about 6 V, about 1 V to about 7 V, about 1 V to about 8 V, about 1 V to about 9 V, about 1 V to about 10 V, about 1 V to about 12 V, about 1 V to about 15 V, about 2 V to about 3 V, about 2 V to about 4 V, about 2 V to about 5 V, about 2 V to about 6 V, about 2 V to about 7 V, about 2 V to about 8 V, about 2 V to about 9 V, about 2 V to about 10 V, about 2 V to about 12 V, about 2 V to about 15 V, about 3 V to about 4 V, about 3 V to about 5 V, about 3 V to about 6 V, about 3 V to about 7 V, about 3 V to about 8 V, about 3 V to about 9 V, about 3 V to about 10 V, about 3 V to about 12 V, about 3 V to about 15 V, about 4 V to about 5 V, about 4 V to about 6 V, about 4 V to about 7 V, about 4 V to about 8 V, about 4 V to about 9 V, about 4 V to about 10 V, about 4 V to about 12 V, about 4 V to about 15 V, about 5 V to about 6 V, about 5 V to about 7 V, about 5 V to about 8 V, about 5 V to about 9 V, about 5 V to about 10 V, about 5 V to about 12 V, about 5 V to about 15 V, about 6 V to about 7 V, about 6 V to about 8 V, about 6 V to about 9 V, about 6 V to about 10 V, about 6 V to about 12 V, about 6 V to about 15 V, about 7 V to about 8 V, about 7 V to about 9 V, about 7 V to about 10 V, about 7 V to about 12 V, about 7 V to about 15 V, about 8 V to about 9 V, about 8 V to about 10 V, about 8 V to about 12 V, about 8 V to about 15 V, about 9 V to about 10 V, about 9 V to about 12 V, about 9 V to about 15 V, about 10 V to about 12 V, about 10 V to about 15 V, or about 12 V to about 15 V. In some instances, the amplitude of the electrical stimulation pattern may be about 1 V, about 2 V, about 3 V, about 4 V, about 5 V, about 6 V, about 7 V, about 8 V, about 9 V, about 10 V, about 12 V, or about 15 V. In some instances, the amplitude of the electrical stimulation pattern may be at least about 1 V, about 2 V, about 3 V, about 4 V, about 5 V, about 6 V, about 7 V, about 8 V, about 9 V, about 10 V, or about 12 V. In some instances, the amplitude of the electrical stimulation pattern may be at most about 2 V, about 3 V, about 4 V, about 5 V, about 6 V, about 7 V, about 8 V, about 9 V, about 10 V, about 12 V, or about 15 V. In some embodiments, the amplitude refers to the mean amplitude. In some embodiments, the amplitude refers to the median amplitude. In some embodiments, the amplitude refers to the maximum amplitude. In some embodiments, the amplitude refers to peak to peak amplitude.

In some instances, the amplitude of the electrical stimulation pattern may be about 0.05 milliampere (mA) to about 10 mA. In some instances, the amplitude of the electrical stimulation pattern may be about 0.05 mA to about 1 mA, about 0.05 mA to about 2 mA, about 0.05 mA to about 3 mA, about 0.05 mA to about 4 mA, about 0.05 mA to about 5 mA, about 0.05 mA to about 6 mA, about 0.05 mA to about 7 mA, about 0.05 mA to about 8 mA, about 0.05 mA to about 9 mA, about 0.05 mA to about 10 mA, about 1 mA to about 2 mA, about 1 mA to about 3 mA, about 1 mA to about 4 mA, about 1 mA to about 5 mA, about 1 mA to about 6 mA, about 1 mA to about 7 mA, about 1 mA to about 8 mA, about 1 mA to about 9 mA, about 1 mA to about 10 mA, about 2 mA to about 3 mA, about 2 mA to about 4 mA, about 2 mA to about 5 mA, about 2 mA to about 6 mA, about 2 mA to about 7 mA, about 2 mA to about 8 mA, about 2 mA to about 9 mA, about 2 mA to about 10 mA, about 3 mA to about 4 mA, about 3 mA to about 5 mA, about 3 mA to about 6 mA, about 3 mA to about 7 mA, about 3 mA to about 8 mA, about 3 mA to about 9 mA, about 3 mA to about 10 mA, about 4 mA to about 5 mA, about 4 mA to about 6 mA, about 4 mA to about 7 mA, about 4 mA to about 8 mA, about 4 mA to about 9 mA, about 4 mA to about 10 mA, about 5 mA to about 6 mA, about 5 mA to about 7 mA, about 5 mA to about 8 mA, about 5 mA to about 9 mA, about 5 mA to about 10 mA, about 6 mA to about 7 mA, about 6 mA to about 8 mA, about 6 mA to about 9 mA, about 6 mA to about 10 mA, about 7 mA to about 8 mA, about 7 mA to about 9 mA, about 7 mA to about 10 mA, about 8 mA to about 9 mA, about 8 mA to about 10 mA, or about 9 mA to about 10 mA. In some instances, the amplitude of the electrical stimulation pattern may be about 0.05 mA, about 1 mA, about 2 mA, about 3 mA, about 4 mA, about 5 mA, about 6 mA, about 7 mA, about 8 mA, about 9 mA, or about 10 mA. In some instances, the amplitude of the electrical stimulation pattern may be at least about 0.05 mA, about 1 mA, about 2 mA, about 3 mA, about 4 mA, about 5 mA, about 6 mA, about 7 mA, about 8 mA, or about 9 mA. In some instances, the amplitude of the electrical stimulation pattern may be at most about 1 mA, about 2 mA, about 3 mA, about 4 mA, about 5 mA, about 6 mA, about 7 mA, about 8 mA, about 9 mA, or about 10 mA. In some embodiments, the amplitude refers to the mean amplitude. In some embodiments, the amplitude refers to the median amplitude. In some embodiments, the amplitude refers to the maximum amplitude.

In some instances, the pulse width of the electric stimulation pattern may be modified or changed. In some instances, the pulse width of the electrical stimulation pattern may be about 60 µs to about 390 µs. In some instances, the pulse width of the electrical stimulation pattern may be about 60 µs to about 90 µs, about 60 µs to about 120 µs, about 60 µs to about 150 µs, about 60 µs to about 180 µs, about 60 µs to about 210 µs, about 60 µs to about 240 µs, about 60 µs to about 270 µs, about 60 µs to about 300 µs, about 60 µs to about 330 µs, about 60 µs to about 360 µs, about 60 µs to about 390 µs, about 90 µs to about 120 µs, about 90 µs to about 150 µs, about 90 µs to about 180 µs, about 90 µs to about 210 µs, about 90 µs to about 240 µs, about 90 µs to about 270 µs, about 90 µs to about 300 µs, about 90 µs to about 330 µs, about 90 µs to about 360 µs, about 90 µs to about 390 µs, about 120 µs to about 150 µs, about 120 µs to about 180 µs, about 120 µs to about 210 µs, about 120 µs to about 240 µs, about 120 µs to about 270 µs, about 120 µs to about 300 µs, about 120 µs to about 330 µs, about 120 µs to about 360 µs, about 120 µs to about 390 µs, about 150 µs to about 180 µs, about 150 µs to about 210 µs, about 150 µs to about 240 µs, about 150 µs to about 270 µs, about 150 µs to about 300 µs, about 150 µs to about 330 µs, about 150 µs to about 360 µs, about 150 µs to about 390 µs, about 180 µs to about 210 µs, about 180 µs to about 240 µs, about 180 µs to about 270 µs, about 180 µs to about 300 µs, about 180 µs to about 330 µs, about 180 µs to about 360 µs, about 180 µs to about 390 µs, about 210 µs to about 240 µs, about 210 µs to about 270 µs, about 210 µs to about 300 µs, about 210 µs to about 330 µs, about 210 µs to about 360 µs, about 210 µs to about 390 µs, about 240 µs to about 270 µs, about 240 µs to about 300 µs, about 240 µs to about 330 µs, about 240 µs to about 360 µs, about 240 µs to about 390 µs, about 270 µs to about 300 µs, about 270 µs to about 330 µs, about 270 µs to about 360 µs, about 270 µs to about 390 µs, about 300 µs to about 330 µs, about 300 µs to about 360 µs, about 300 µs to about 390 µs, about 330 µs to about 360 µs, about 330 µs to about 390 µs, or about 360 µs to about 390 µs. In some instances, the pulse width of the electrical stimulation pattern may be about 60 µs, about 90 µs, about 120 µs, about 150 µs, about 180 µs, about 210 µs, about 240 µs, about 270 µs, about 300 µs, about 330 µs, about 360 µs, or about 390 µs. In some instances, the pulse width of the electrical stimulation pattern may be at least about 60 µs, about 90 µs, about 120 µs, about 150 µs, about 180 µs, about 210 µs, about 240 µs, about 270 µs, about 300 µs, about 330 µs, or about 360 µs. In some instances, the pulse width of the electrical stimulation pattern may be at most about 90 µs, about 120 µs, about 150 µs, about 180 µs, about 210 µs, about 240 µs, about 270 µs, about 300 µs, about 330 µs, about 360 µs, or about 390 µs. In some embodiments, the pulse width refers to the mean pulse width. In some embodiments, the pulse width refers to the median pulse width. In some embodiments, the pulse width refers to the maximum pulse width.

Sensors for Use with Embodiments of the Device Described Herein

In some instances, a sensor electrode for use with embodiments of the device described herein may be configured to senses a parameter associated with a response of an individual intending to prevent an episode of incontinence or that indicates the individual may have an episode of incontinence. In some cases, the sensor electrode may be configured to sense a contraction of a muscle of the individual that results in a partial contraction of a sphincter that controls bladder or bowel voiding. In some cases, a sensor electrode may be configured to sense bulk motion or anatomical stress of an individual. In some instances, the sensor electrode may comprise a sensor configured to detect electromyography (EMG) signals. In some cases, the sensor electrode may be configured to sense myoelectric activity. In some instances, an EMG signal threshold may determine that a contraction of at least one pelvic muscle has occurred. In some cases, the strength of the EMG signal may be proportional to the strength of the contraction of at least one pelvic muscle. In some instances, the sensor electrode detects an action potential signal. In some cases, the device comprises an amplifier to amplify the signal obtained by the sensor electrode, to facilitate analysis and classification of the signal by the processor.

In some cases, the sensor electrode may be implanted within the pelvis of the individual. In some instances, the sensor electrode may be implanted at or adjacent to the pudendal nerve. In some cases, the sensor electrode may be implanted at or adjacent to the sacral nerve. In some cases, the sensor electrode may be implanted within or adjacent to one or more of the pelvic muscles. In some instances, the sensor electrode may be implanted at or adjacent to the pelvic floor. In some cases, the sensor electrode may be implanted at or adjacent to the urethral sphincter. In some instances, the sensor electrode may be implanted at or adjacent to one or more of the urethra, ureter, and bladder. In some cases, the sensor electrode may be implanted at or adjacent to the anal sphincter. In some instances, the sensor electrode may be implanted at or adjacent to one or more of the anus, rectum, and bowel. In some instances, the devices described herein may comprise a plurality of sensor electrodes. In some cases, the devices described herein may comprise one or more sensor electrodes. In some instances, the devices described herein may comprise a different sensor electrode, or a second sensor electrode. In some cases, the sensor electrode may detect the signal from a muscle area innervated by a first pudendal nerve and the different or second sensor electrode may detect signal from a muscle area innervated by a second pudendal nerve. In some instances, the sensor electrode may detect a signal from a muscle area innervated by a first sacral nerve and the different or second sensor electrode detects a signal from a muscle area innervated by a second sacral nerve.

In some instances, the sensor electrode may comprise a casing and a lead. In some instances, the casing may be made of titanium, titanium alloy, tantalum, or any combination thereof. In some cases, the lead may be made of a metal alloy. In some embodiments, a sensor electrode and a stimulator electrode may be positioned on a single lead. In some instances, the lead may be electrically coupled to one or more sensor electrodes or one or more stimulator electrodes. In some embodiments, a sensor electrode and a stimulator electrode are positioned on separate leads. In some cases, the one or more sensor electrodes may comprise bioelectrical sensor electrodes.

Electrodes for Use with Embodiments of the Device Described Herein

In some cases, the sensor electrode and the stimulator electrode may be located on a single lead. In some instances, one or more sensor electrodes and one or more stimulator electrodes may be located on a single lead. In some cases, one sensor electrode and one stimulator electrode may be located on a single lead. In some instances, the sensor electrode and the stimulator electrode may be located on separate leads. In some cases, the sensor electrode and the stimulator electrode may each be located on its own lead. In some cases, the one or more sensor electrodes and one or more stimulator electrodes may be in a linear geometry, triangular geometry, square geometry, hexagonal geometry, or a general polygonal geometry. In some cases, the electrodes located on a single lead may be spaced by a distance. In some cases, the spacing provides the capability to stimulate multiple locations along the length of the nerve. In some cases, the electrodes may be separated by a distance of at least about 1 mm, about 1.5 mm, about 2 mm, about 2.5 mm, about 5 mm, about 10 mm, about 20 mm, about 30 mm, about 40 mm, about 50 mm, or about 60 mm. In some cases, the electrodes may be separated by a distance of at most about 1.5 mm, about 2 mm, about 2.5 mm, about 5 mm, about 10 mm, about 20 mm, about 30 mm, about 40 mm, about 50 mm, about 60 mm, or about 80 mm.

In some instances, the device may comprise one or more leads. In some cases, the device may comprise at least two leads. In some instances, the device may comprise at least 1, 2, 3, 4, 5, 6, 7, 8, 9, or 10 leads. In some cases, the device may comprise at most 1, 2, 3, 4, 5, 6, 7, 8, 9, or 10 leads. In some instances, the device may comprise 1, 2, 3, 4, 5, 6, 7, 8, 9, or 10 leads. In some cases, each lead may comprise one or more electrodes. In some cases, the one or more electrodes may comprise one or more sensor and/or stimulation electrodes. In some cases, the one or more electrodes on a lead may comprise about 1 electrode to about 10 electrodes. In some cases, the one or more electrodes on a lead may comprise about 1 electrode to about 2 electrodes, about 1 electrode to about 3 electrodes, about 1 electrode to about 4 electrodes, about 1 electrode to about 5 electrodes, about 1 electrode to about 6 electrodes, about 1 electrode to about 7 electrodes, about 1 electrode to about 8 electrodes, about 1 electrode to about 9 electrodes, about 1 electrode to about 10 electrodes, about 2 electrodes to about 3 electrodes, about 2 electrodes to about 4 electrodes, about 2 electrodes to about 5 electrodes, about 2 electrodes to about 6 electrodes, about 2 electrodes to about 7 electrodes, about 2 electrodes to about 8 electrodes, about 2 electrodes to about 9 electrodes, about 2 electrodes to about 10 electrodes, about 3 electrodes to about 4 electrodes, about 3 electrodes to about 5 electrodes, about 3 electrodes to about 6 electrodes, about 3 electrodes to about 7 electrodes, about 3 electrodes to about 8 electrodes, about 3 electrodes to about 9 electrodes, about 3 electrodes to about 10 electrodes, about 4 electrodes to about 5 electrodes, about 4 electrodes to about 6 electrodes, about 4 electrodes to about 7 electrodes, about 4 electrodes to about 8 electrodes, about 4 electrodes to about 9 electrodes, about 4 electrodes to about 10 electrodes, about 5 electrodes to about 6 electrodes, about 5 electrodes to about 7 electrodes, about 5 electrodes to about 8 electrodes, about 5 electrodes to about 9 electrodes, about 5 electrodes to about 10 electrodes, about 6 electrodes to about 7 electrodes, about 6 electrodes to about 8 electrodes, about 6 electrodes to about 9 electrodes, about 6 electrodes to about 10 electrodes, about 7 electrodes to about 8 electrodes, about 7 electrodes to about 9 electrodes, about 7 electrodes to about 10 electrodes, about 8 electrodes to about 9 electrodes, about 8 electrodes to about 10 electrodes, or about 9 electrodes to about 10 electrodes. In some cases, the one or more electrodes on a lead may comprise about 1 electrode, about 2 electrodes, about 3 electrodes, about 4 electrodes, about 5 electrodes, about 6 electrodes, about 7 electrodes, about 8 electrodes, about 9 electrodes, or about 10 electrodes. In some cases, the one or more electrodes on a lead may comprise at least about 1 electrode, about 2 electrodes, about 3 electrodes, about 4 electrodes, about 5 electrodes, about 6 electrodes, about 7 electrodes, about 8 electrodes, or about 9 electrodes. In some cases, the one or more electrodes on a lead may comprise at most about 2 electrodes, about 3 electrodes, about 4 electrodes, about 5 electrodes, about 6 electrodes, about 7 electrodes, about 8 electrodes, about 9 electrodes, or about 10 electrodes.

In some cases, each electrode may comprise a length, whereby the length may provide localized excitation of one or more nerves of the sacral or pudendal nerve. In some cases, each electrode may comprise a length of about 0.1 millimeter (mm) to about 2 mm. In some cases, each electrode may comprise a length of about 0.1 mm to about 0.3 mm, about 0.1 mm to about 0.5 mm, about 0.1 mm to about 0.7 mm, about 0.1 mm to about 0.8 mm, about 0.1 mm to about 1 mm, about 0.1 mm to about 1.2 mm, about 0.1 mm to about 1.4 mm, about 0.1 mm to about 1.5 mm, about 0.1 mm to about 2 mm, about 0.3 mm to about 0.5 mm, about 0.3 mm to about 0.7 mm, about 0.3 mm to about 0.8 mm, about 0.3 mm to about 1 mm, about 0.3 mm to about 1.2 mm, about 0.3 mm to about 1.4 mm, about 0.3 mm to about 1.5 mm, about 0.3 mm to about 2 mm, about 0.5 mm to about 0.7 mm, about 0.5 mm to about 0.8 mm, about 0.5 mm to about 1 mm, about 0.5 mm to about 1.2 mm, about 0.5 mm to about 1.4 mm, about 0.5 mm to about 1.5 mm, about 0.5 mm to about 2 mm, about 0.7 mm to about 0.8 mm, about 0.7 mm to about 1 mm, about 0.7 mm to about 1.2 mm, about 0.7 mm to about 1.4 mm, about 0.7 mm to about 1.5 mm, about 0.7 mm to about 2 mm, about 0.8 mm to about 1 mm, about 0.8 mm to about 1.2 mm, about 0.8 mm to about 1.4 mm, about 0.8 mm to about 1.5 mm, about 0.8 mm to about 2 mm, about 1 mm to about 1.2 mm, about 1 mm to about 1.4 mm, about 1 mm to about 1.5 mm, about 1 mm to about 2 mm, about 1.2 mm to about 1.4 mm, about 1.2 mm to about 1.5 mm, about 1.2 mm to about 2 mm, about 1.4 mm to about 1.5 mm, about 1.4 mm to about 2 mm, or about 1.5 mm to about 2 mm. In some cases, each electrode may comprise a length of about 0.1 mm, about 0.3 mm, about 0.5 mm, about 0.7 mm, about 0.8 mm, about 1 mm, about 1.2 mm, about 1.4 mm, about 1.5 mm, or about 2 mm. In some cases, each electrode may comprise a length of at least about 0.1 mm, about 0.3 mm, about 0.5 mm, about 0.7 mm, about 0.8 mm, about 1 mm, about 1.2 mm, about 1.4 mm, or about 1.5 mm. In some cases, each electrode may comprise a length of at most about 0.3 mm, about 0.5 mm, about 0.7 mm, about 0.8 mm, about 1 mm, about 1.2 mm, about 1.4 mm, about 1.5 mm, or about 2 mm.

In some cases, the one or more leads may comprise a length between the proximal tip of the lead to the distal end electrically coupled to the stimulator. In some cases, the length of the lead may vary based upon the anatomy of the individual or subject receiving the implanted device and leads. In some cases, the lead length may comprise a length, whereby the lead electrodes may be placed near and/or adjacent to the sacral and/or pudendal nerve yet reach the placement of the stimulator in buttock fat pockets of the subject. In some instances, the one or more leads may comprise a length of about 20 centimeters (cm) to about 50 cm. In some instances, the one or more leads may comprise a length of about 20 cm to about 25 cm, about 20 cm to about 30 cm, about 20 cm to about 35 cm, about 20 cm to about 40 cm, about 20 cm to about 45 cm, about 20 cm to about 50 cm, about 25 cm to about 30 cm, about 25 cm to about 35 cm, about 25 cm to about 40 cm, about 25 cm to about 45 cm, about 25 cm to about 50 cm, about 30 cm to about 35 cm, about 30 cm to about 40 cm, about 30 cm to about 45 cm, about 30 cm to about 50 cm, about 35 cm to about 40 cm, about 35 cm to about 45 cm, about 35 cm to about 50 cm, about 40 cm to about 45 cm, about 40 cm to about 50 cm, or about 45 cm to about 50 cm. In some instances, the one or more leads may comprise a length of about 20 cm, about 25 cm, about 30 cm, about 35 cm, about 40 cm, about 45 cm, or about 50 cm. In some instances, the one or more leads may comprise a length of at least about 20 cm, about 25 cm, about 30 cm, about 35 cm, about 40 cm, or about 45 cm. In some instances, the one or more leads may comprise a length of at most about 25 cm, about 30 cm, about 35 cm, about 40 cm, about 45 cm, or about 50 cm.

In some cases, the one or more leads may comprise a diameter. In some cases, the diameter of the lead may vary based upon the anatomy of the individual or subject receiving the implanted device and leads. In some cases, the lead diameter may comprise a diameter, whereby the diameter provides a form factor for minimally invasive placement of the lead in the subject. In some cases, the diameter of the lead may comprise a diameter at which the lead will resist breakage. In some cases, the one or more leads may have an outer diameter of about 0.1 mm to about 2 mm. In some cases, the one or more leads may have an outer diameter of about 0.1 mm to about 0.2 mm, about 0.1 mm to about 0.3 mm, about 0.1 mm to about 0.5 mm, about 0.1 mm to about 0.8 mm, about 0.1 mm to about 1 mm, about 0.1 mm to about 1.2 mm, about 0.1 mm to about 1.4 mm, about 0.1 mm to about 1.5 mm, about 0.1 mm to about 2 mm, about 0.2 mm to about 0.3 mm, about 0.2 mm to about 0.5 mm, about 0.2 mm to about 0.8 mm, about 0.2 mm to about 1 mm, about 0.2 mm to about 1.2 mm, about 0.2 mm to about 1.4 mm, about 0.2 mm to about 1.5 mm, about 0.2 mm to about 2 mm, about 0.3 mm to about 0.5 mm, about 0.3 mm to about 0.8 mm, about 0.3 mm to about 1 mm, about 0.3 mm to about 1.2 mm, about 0.3 mm to about 1.4 mm, about 0.3 mm to about 1.5 mm, about 0.3 mm to about 2 mm, about 0.5 mm to about 0.8 mm, about 0.5 mm to about 1 mm, about 0.5 mm to about 1.2 mm, about 0.5 mm to about 1.4 mm, about 0.5 mm to about 1.5 mm, about 0.5 mm to about 2 mm, about 0.8 mm to about 1 mm, about 0.8 mm to about 1.2 mm, about 0.8 mm to about 1.4 mm, about 0.8 mm to about 1.5 mm, about 0.8 mm to about 2 mm, about 1 mm to about 1.2 mm, about 1 mm to about 1.4 mm, about 1 mm to about 1.5 mm, about 1 mm to about 2 mm, about 1.2 mm to about 1.4 mm, about 1.2 mm to about 1.5 mm, about 1.2 mm to about 2 mm, about 1.4 mm to about 1.5 mm, about 1.4 mm to about 2 mm, or about 1.5 mm to about 2 mm. In some cases, the one or more leads may have an outer diameter of about 0.1 mm, about 0.2 mm, about 0.3 mm, about 0.5 mm, about 0.8 mm, about 1 mm, about 1.2 mm, about 1.4 mm, about 1.5 mm, or about 2 mm. In some cases, the one or more leads may have an outer diameter of at least about 0.1 mm, about 0.2 mm, about 0.3 mm, about 0.5 mm, about 0.8 mm, about 1 mm, about 1.2 mm, about 1.4 mm, or about 1.5 mm. In some cases, the one or more leads may have an outer diameter of at most about 0.2 mm, about 0.3 mm, about 0.5 mm, about 0.8 mm, about 1 mm, about 1.2 mm, about 1.4 mm, about 1.5 mm, or about 2 mm.

In some cases, the one or more leads described elsewhere herein may comprise an internal stylet and/or mandrel configured to provide rigidity to the lead for implantation and/or insertion to a subject. In some cases, the internal stylet may be removed from the lead once the lead has been inserted and implanted. In some instances, the one or more leads described elsewhere herein may be sterilizable with conventional methods of sterilization used in the medical field, e.g., gas sterilization, steam sterilization, UV sterilization, etc.

In some instances, the one or more leads, described elsewhere herein, may be electrically coupled to the electric stimulator, described elsewhere herein. In some instances, the one or more leads may be coupled to the stimulator and may at a later point in time be uncoupled from the stimulator. In some instances, the one or more leads may couple to the electric stimulator with a quick release electrical coupling. In some cases, the one or more leads may be coupled to the electric stimulator by a set screw fastener, whereby a lead is inserted into a hollow cylindrical geometry in electrical communication with the electric stimulator internal circuitry. The lead may then be fastened i.e., held in tension against the inner wall of the hollow cylindrical geometry, to the conductive hollow cylindrical geometry with a non-conductive machine set screw. The one or more leads may be placed into the electric stimulator prior to or during the surgical implantation procedure.

In some instances, the sensor electrode and the stimulator electrode may be operatively coupled to a processor and a non-transitory computer readable medium that includes software. In some cases, the sensor electrode may be calibrated by the individual using an external input device that interfaces with the software. In some instances, the software may be configured to record a signal from the sensor electrode. In some cases, the software may be configured to adjust the sensor electrode in response to the signal.

In some instances, the stimulator electrode may provide an electrical stimulation to the pudendal nerve. In some cases, the stimulator electrode may provide an electrical stimulation to the sacral nerve. In some instances, the stimulator electrode may provide an electrical stimulation to one or more of the nerves innervating the pelvic muscles. In some cases, the electrode may comprise one or more electrodes or leads e.g., a first and second electrode. In some instances, the electrode may comprise one or more stimulator electrodes. In some cases, an electrode may comprise a first stimulator electrode configured to stimulate one pudendal nerve, and a second stimulator electrode configured to stimulate another spatially independent region of the same pudendal nerve. In some cases, the first stimulator electrode may stimulate the main trunk of the pudendal nerve and the second stimulator electrode may stimulate the distal nerve of the pudendal nerve. In some instances, the distal nerve of the pudendal nerve comprises branches thereof the distal pudendal nerve. In some cases, the first stimulator electrode may stimulate the trunk of the pudendal nerve and the second stimulator electrode may stimulate a main branch of the pudendal nerve e.g., dorsal genital nerve. In some cases, the stimulator electrode may provide an electrical stimulation to one or more of the nerves innervating the urethral sphincter. In some instances, the stimulator electrode may provide an electrical stimulation to one or more of the nerves innervating the urethra. In some cases, the stimulator electrode may provide an electrical stimulation to one or more of the nerves innervating the bladder. In some instances, the stimulator electrode may provide an electrical stimulation to one or more of the nerves innervating the ureter. In some cases, the stimulator electrode may provide an electrical stimulation to one or more of the nerves innervating the anal sphincter. In some cases, the stimulator electrode may provide an electrical stimulation to one or more of the nerves innervating the anus. In some instances, the stimulator electrode may provide an electrical stimulation to one or more of the nerves innervating the rectum. In some cases, the stimulator electrode may provide an electrical stimulation to one or more of the nerves innervating the bowel. In some instances, the devices described herein may comprise a plurality of stimulator electrodes. In some instances, the devices described herein may comprise one or more stimulator electrodes. In some instances, the devices described herein may comprise a different stimulator electrode, or a second stimulator electrode. In some cases, the stimulator electrode may stimulate a first pudendal nerve and the different or second stimulator electrode stimulates a second pudendal nerve. In some cases, the stimulator electrode may stimulate a first sacral nerve and the different or second stimulator electrode stimulates a second sacral nerve.

In some instances, the stimulator electrode of the device may provide a constant electrical stimulation. In some cases, the stimulator electrode of the device may provide a constant electrical stimulation at a lower intensity level than the electrical stimulation provided to prevent an episode of incontinence. In some cases, constant electrical stimulation may comprise constant frequency, amplitude, current, or any combination thereof. In some instances, the intensity or duration of the electrical stimulation provided may prevent an episode of incontinence varies according to the individual's response to a possible episode of incontinence that is sensed by the sensor electrode. In some cases, the individual's response to prevent a possible episode of incontinence that is sensed by the sensor electrode may be insufficient on its own to prevent the episode of incontinence and the electrical stimulation delivered by the stimulator electrode of the device provides sufficient stimulation, together with the response, to prevent the episode of incontinence. In some cases, the individual's response to prevent a possible episode of incontinence that may be sensed by the sensor electrode combined with the electrical stimulation delivered by the stimulator electrode of the device provides sufficient stimulation to trigger the action potential of the muscles responsible for the incontinence, resulting in contraction of the muscle. In some cases, the combined stimulation from the individual and the device may result in contraction of a muscle. In some instances, the muscle may comprise a urethral sphincter. In some cases, the muscle may comprise an anal sphincter. In some cases, the muscle may comprise one or more of the pelvic floor muscles.

In some instances, the sensor electrode may comprise casing and a lead. In some instances, the casing may be made of titanium or a titanium alloy. In some cases, the lead may be made of a metal alloy.

Device Anchors

In some cases, the devices may be anchored when implanted by one the one or more surgical device. In some instances, anchoring of the devices may be achieved by sliding the device over the lead, described elsewhere herein, and then compressing it onto the lead using ligatures such that it is immobile. These ligatures may be used to fix the anchoring device to native adjacent tissue such as ligament or periosteum. In some instances, the device may comprise groves for the purpose of aligning compression ligatures. In some instances, the anchoring device may comprise a torque system to compress the device onto the lead such that it is immobile. In some instances, the device may be compressed at a single point onto the lead. In some instances, the device is compressed at two or more points onto the lead. The electric stimulator may comprise radio-opaque markers that may permit visualization of the electric stimulator under x-ray e.g., fluoroscopy during and/or after implantation. In some instances, fluoroscopy may be used alone or in combination with EMG sensor electrode readings of pelvic floor muscles to verify placement or to adjustment placement of sensor electrode leads, stimulator electrode leads, and/or the stimulator.

Electrical Signal

Figure 4:
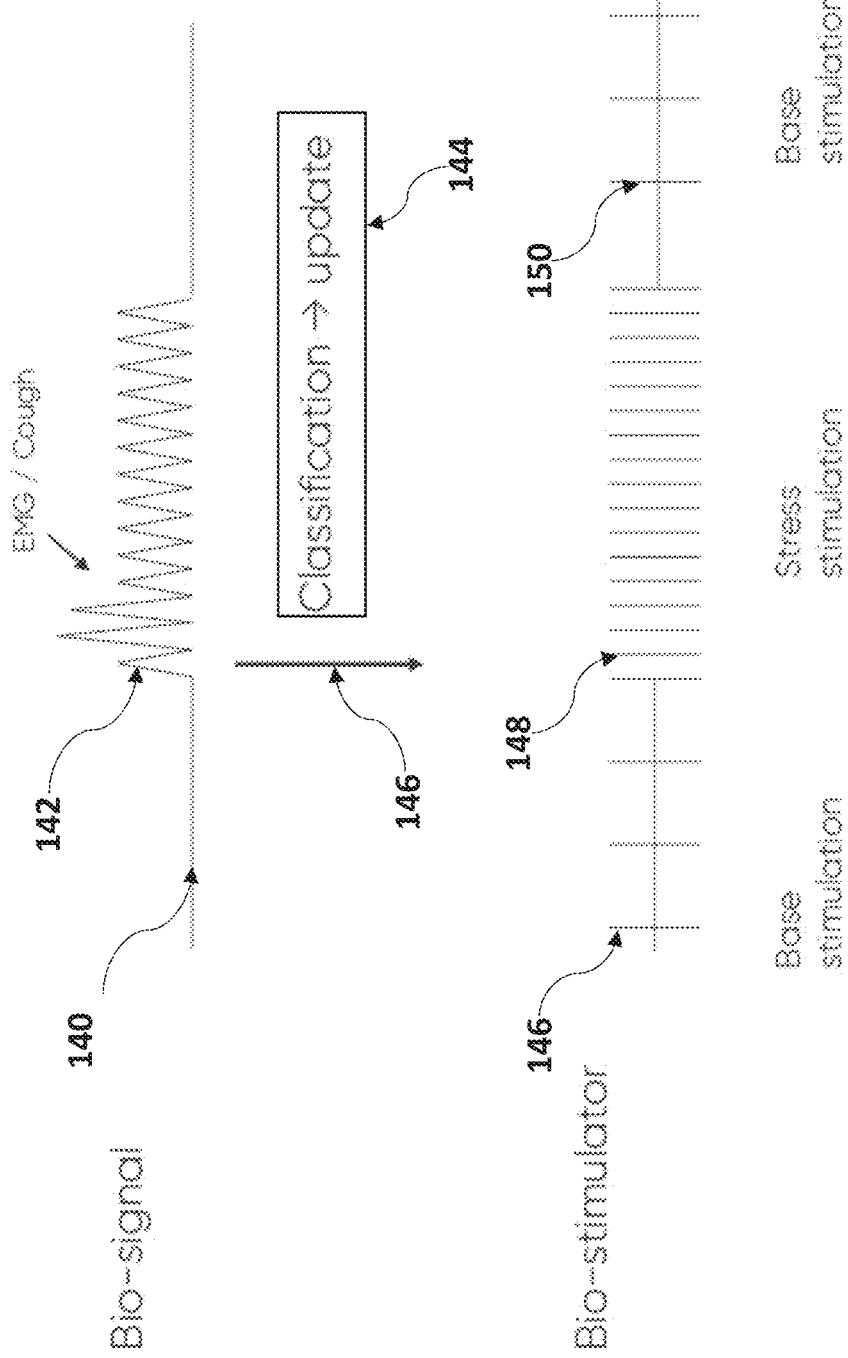
FIG. 4 shows exemplary embodiments of depicting a bio-signal and a bio-stimulator electrical stimulation. The bio-signal captured by the sensor electrode is analyzed and classified to identify any stress events, such as a cough or a sudden movement, from an electromyography (EMG) signal. The stimulator electrodes deliver the bio-simulator, an electrical stimulation that is adapted from the base stimulation to account for the stress event.

FIG. 4 depicts the sensed myoelectric EMG signal and a corresponding electrical stimulation ("Bio-stimulator") provided by the devices disclosed herein. In some cases, the myoelectric EMG signal ("Bio-signal") 140 may comprise electrical fluctuations 142 corresponding to contractile activity of the muscle near the sensor electrode. In some cases, the electrical fluctuations 142 may represent a cough, sudden movement, change in inertia, or any combination thereof from an electromyography (EMG) reading. In some instances, the bio-signal captured by the sensor electrode may be analyzed and classified 144 to identify any stress events, such as a cough or a sudden movement, from an EMG reading. In some cases, the identified stress event may initiate a process 146 by which the implantable electric stimulator may deliver an electric stimulation pattern 148 to via one or more stimulator electrodes to a one or more pudendal nerve to prevent an episode of incontinence. In some cases, the stimulator electrode may deliver an electrical stimulation by the one or more stimulator electrodes 122 that is configured to supplement the innate reflex detected by the one or more sensor electrodes 120 to account for the stress event otherwise leading to an incontinence event.

In some cases, the electric stimulator may comprise a width and length to be readily implantable in a patient. In some cases, the electric stimulator may comprise a width and length to accommodate circuitry and/or other system level components, described elsewhere herein.

In some instances, the electric stimulator may comprise a width and length to provide sufficient space for a battery, where the battery may comprise a lifetime after which the battery may be replaced. In some cases, the battery lifetime may comprise about 5 years to about 15 years. In some cases, the battery lifetime may comprise about 5 years to about 6 years, about 5 years to about 7 years, about 5 years to about 8 years, about 5 years to about 9 years, about 5 years to about 10 years, about 5 years to about 11 years, about 5 years to about 12 years, about 5 years to about 13 years, about 5 years to about 14 years, about 5 years to about 15 years, about 6 years to about 7 years, about 6 years to about 8 years, about 6 years to about 9 years, about 6 years to about 10 years, about 6 years to about 11 years, about 6 years to about 12 years, about 6 years to about 13 years, about 6 years to about 14 years, about 6 years to about 15 years, about 7 years to about 8 years, about 7 years to about 9 years, about 7 years to about 10 years, about 7 years to about 11 years, about 7 years to about 12 years, about 7 years to about 13 years, about 7 years to about 14 years, about 7 years to about 15 years, about 8 years to about 9 years, about 8 years to about 10 years, about 8 years to about 11 years, about 8 years to about 12 years, about 8 years to about 13 years, about 8 years to about 14 years, about 8 years to about 15 years, about 9 years to about 10 years, about 9 years to about 11 years, about 9 years to about 12 years, about 9 years to about 13 years, about 9 years to about 14 years, about 9 years to about 15 years, about 10 years to about 11 years, about 10 years to about 12 years, about 10 years to about 13 years, about 10 years to about 14 years, about 10 years to about 15 years, about 11 years to about 12 years, about 11 years to about 13 years, about 11 years to about 14 years, about 11 years to about 15 years, about 12 years to about 13 years, about 12 years to about 14 years, about 12 years to about 15 years, about 13 years to about 14 years, about 13 years to about 15 years, or about 14 years to about 15 years. In some cases, the battery lifetime may comprise about 5 years, about 6 years, about 7 years, about 8 years, about 9 years, about 10 years, about 11 years, about 12 years, about 13 years, about 14 years, or about 15 years. In some cases, the battery lifetime may comprise at least about 5 years, about 6 years, about 7 years, about 8 years, about 9 years, about 10 years, about 11 years, about 12 years, about 13 years, or about 14 years. In some cases, the battery lifetime may comprise at most about 6 years, about 7 years, about 8 years, about 9 years, about 10 years, about 11 years, about 12 years, about 13 years, about 14 years, or about 15 years.

In some cases, the electric stimulator battery may require charging once in about 1 day to about 12 days. In some cases, the electric stimulator battery may require charging once in about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 2 days to about 3 days, about 2 days to about 4 days, about 2 days to about 5 days, about 2 days to about 6 days, about 2 days to about 7 days, about 2 days to about 8 days, about 2 days to about 9 days, about 2 days to about 10 days, about 2 days to about 11 days, about 2 days to about 12 days, about 3 days to about 4 days, about 3 days to about 5 days, about 3 days to about 6 days, about 3 days to about 7 days, about 3 days to about 8 days, about 3 days to about 9 days, about 3 days to about 10 days, about 3 days to about 11 days, about 3 days to about 12 days, about 4 days to about 5 days, about 4 days to about 6 days, about 4 days to about 7 days, about 4 days to about 8 days, about 4 days to about 9 days, about 4 days to about 10 days, about 4 days to about 11 days, about 4 days to about 12 days, about 5 days to about 6 days, about 5 days to about 7 days, about 5 days to about 8 days, about 5 days to about 9 days, about 5 days to about 10 days, about 5 days to about 11 days, about 5 days to about 12 days, about 6 days to about 7 days, about 6 days to about 8 days, about 6 days to about 9 days, about 6 days to about 10 days, about 6 days to about 11 days, about 6 days to about 12 days, about 7 days to about 8 days, about 7 days to about 9 days, about 7 days to about 10 days, about 7 days to about 11 days, about 7 days to about 12 days, about 8 days to about 9 days, about 8 days to about 10 days, about 8 days to about 11 days, about 8 days to about 12 days, about 9 days to about 10 days, about 9 days to about 11 days, about 9 days to about 12 days, about 10 days to about 11 days, about 10 days to about 12 days, or about 11 days to about 12 days. In some cases, the electric stimulator battery may require charging once in about 1 day, about 2 days, about 3 days, about 4 days, about 5 days, about 6 days, about 7 days, about 8 days, about 9 days, about 10 days, about 11 days, or about 12 days. In some cases, the electric stimulator battery may require charging once in at least about 1 day, about 2 days, about 3 days, about 4 days, about 5 days, about 6 days, about 7 days, about 8 days, about 9 days, about 10 days, or about 11 days. In some cases, the electric stimulator battery may require charging once in at most about 2 days, about 3 days, about 4 days, about 5 days, about 6 days, about 7 days, about 8 days, about 9 days, about 10 days, about 11 days, or about 12 days.

In some instances, the electric stimulator may comprise a width of about 1 mm to about 50 mm. In some instances, the electric stimulator may comprise a width of about 1 mm to about 5 mm, about 1 mm to about 10 mm, about 1 mm to about 15 mm, about 1 mm to about 20 mm, about 1 mm to about 25 mm, about 1 mm to about 30 mm, about 1 mm to about 35 mm, about 1 mm to about 40 mm, about 1 mm to about 45 mm, about 1 mm to about 50 mm, about 5 mm to about 10 mm, about 5 mm to about 15 mm, about 5 mm to about 20 mm, about 5 mm to about 25 mm, about 5 mm to about 30 mm, about 5 mm to about 35 mm, about 5 mm to about 40 mm, about 5 mm to about 45 mm, about 5 mm to about 50 mm, about 10 mm to about 15 mm, about 10 mm to about 20 mm, about 10 mm to about 25 mm, about 10 mm to about 30 mm, about 10 mm to about 35 mm, about 10 mm to about 40 mm, about 10 mm to about 45 mm, about 10 mm to about 50 mm, about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 25 mm to about 30 mm, about 25 mm to about 35 mm, about 25 mm to about 40 mm, about 25 mm to about 45 mm, about 25 mm to about 50 mm, about 30 mm to about 35 mm, about 30 mm to about 40 mm, about 30 mm to about 45 mm, about 30 mm to about 50 mm, about 35 mm to about 40 mm, about 35 mm to about 45 mm, about 35 mm to about 50 mm, about 40 mm to about 45 mm, about 40 mm to about 50 mm, or about 45 mm to about 50 mm. In some instances, the electric stimulator may comprise a width of about 1 mm, about 5 mm, about 10 mm, about 15 mm, about 20 mm, about 25 mm, about 30 mm, about 35 mm, about 40 mm, about 45 mm, or about 50 mm. In some instances, the electric stimulator may comprise a width of at least about 1 mm, about 5 mm, about 10 mm, about 15 mm, about 20 mm, about 25 mm, about 30 mm, about 35 mm, about 40 mm, or about 45 mm. In some instances, the electric stimulator may comprise a width of at most about 5 mm, about 10 mm, about 15 mm, about 20 mm, about 25 mm, about 30 mm, about 35 mm, about 40 mm, about 45 mm, or about 50 mm.

In some instances, the electric stimulator may comprise a length of about 1 mm to about 50 mm. In some instances, the electric stimulator may comprise a length of about 1 mm to about 5 mm, about 1 mm to about 10 mm, about 1 mm to about 15 mm, about 1 mm to about 20 mm, about 1 mm to about 25 mm, about 1 mm to about 30 mm, about 1 mm to about 35 mm, about 1 mm to about 40 mm, about 1 mm to about 45 mm, about 1 mm to about 50 mm, about 5 mm to about 10 mm, about 5 mm to about 15 mm, about 5 mm to about 20 mm, about 5 mm to about 25 mm, about 5 mm to about 30 mm, about 5 mm to about 35 mm, about 5 mm to about 40 mm, about 5 mm to about 45 mm, about 5 mm to about 50 mm, about 10 mm to about 15 mm, about 10 mm to about 20 mm, about 10 mm to about 25 mm, about 10 mm to about 30 mm, about 10 mm to about 35 mm, about 10 mm to about 40 mm, about 10 mm to about 45 mm, about 10 mm to about 50 mm, about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 25 mm to about 30 mm, about 25 mm to about 35 mm, about 25 mm to about 40 mm, about 25 mm to about 45 mm, about 25 mm to about 50 mm, about 30 mm to about 35 mm, about 30 mm to about 40 mm, about 30 mm to about 45 mm, about 30 mm to about 50 mm, about 35 mm to about 40 mm, about 35 mm to about 45 mm, about 35 mm to about 50 mm, about 40 mm to about 45 mm, about 40 mm to about 50 mm, or about 45 mm to about 50 mm. In some instances, the electric stimulator may comprise a length of about 1 mm, about 5 mm, about 10 mm, about 15 mm, about 20 mm, about 25 mm, about 30 mm, about 35 mm, about 40 mm, about 45 mm, or about 50 mm. In some instances, the electric stimulator may comprise a length of at least about 1 mm, about 5 mm, about 10 mm, about 15 mm, about 20 mm, about 25 mm, about 30 mm, about 35 mm, about 40 mm, or about 45 mm. In some instances, the electric stimulator may comprise a length of at most about 5 mm, about 10 mm, about 15 mm, about 20 mm, about 25 mm, about 30 mm, about 35 mm, about 40 mm, about 45 mm, or about 50 mm.

In some instances, the electric stimulator may comprise a height of about 0.5 mm to about 5.5 mm. In some instances, the electric stimulator may comprise a height of about 0.5 mm to about 1 mm, about 0.5 mm to about 1.5 mm, about 0.5 mm to about 2 mm, about 0.5 mm to about 2.5 mm, about 0.5 mm to about 3 mm, about 0.5 mm to about 3.5 mm, about 0.5 mm to about 4 mm, about 0.5 mm to about 4.5 mm, about 0.5 mm to about 5 mm, about 0.5 mm to about 5.5 mm, about 1 mm to about 1.5 mm, about 1 mm to about 2 mm, about 1 mm to about 2.5 mm, about 1 mm to about 3 mm, about 1 mm to about 3.5 mm, about 1 mm to about 4 mm, about 1 mm to about 4.5 mm, about 1 mm to about 5 mm, about 1 mm to about 5.5 mm, about 1.5 mm to about 2 mm, about 1.5 mm to about 2.5 mm, about 1.5 mm to about 3 mm, about 1.5 mm to about 3.5 mm, about 1.5 mm to about 4 mm, about 1.5 mm to about 4.5 mm, about 1.5 mm to about 5 mm, about 1.5 mm to about 5.5 mm, about 2 mm to about 2.5 mm, about 2 mm to about 3 mm, about 2 mm to about 3.5 mm, about 2 mm to about 4 mm, about 2 mm to about 4.5 mm, about 2 mm to about 5 mm, about 2 mm to about 5.5 mm, about 2.5 mm to about 3 mm, about 2.5 mm to about 3.5 mm, about 2.5 mm to about 4 mm, about 2.5 mm to about 4.5 mm, about 2.5 mm to about 5 mm, about 2.5 mm to about 5.5 mm, about 3 mm to about 3.5 mm, about 3 mm to about 4 mm, about 3 mm to about 4.5 mm, about 3 mm to about 5 mm, about 3 mm to about 5.5 mm, about 3.5 mm to about 4 mm, about 3.5 mm to about 4.5 mm, about 3.5 mm to about 5 mm, about 3.5 mm to about 5.5 mm, about 4 mm to about 4.5 mm, about 4 mm to about 5 mm, about 4 mm to about 5.5 mm, about 4.5 mm to about 5 mm, about 4.5 mm to about 5.5 mm, or about 5 mm to about 5.5 mm. In some instances, the electric stimulator may comprise a height of about 0.5 mm, about 1 mm, about 1.5 mm, about 2 mm, about 2.5 mm, about 3 mm, about 3.5 mm, about 4 mm, about 4.5 mm, about 5 mm, or about 5.5 mm. In some instances, the electric stimulator may comprise a height of at least about 0.5 mm, about 1 mm, about 1.5 mm, about 2 mm, about 2.5 mm, about 3 mm, about 3.5 mm, about 4 mm, about 4.5 mm, or about 5 mm. In some instances, the electric stimulator may comprise a height of at most about 1 mm, about 1.5 mm, about 2 mm, about 2.5 mm, about 3 mm, about 3.5 mm, about 4 mm, about 4.5 mm, about 5 mm, or about 5.5 mm.

In some instances, the electric stimulator may comprise a mass of about 1 g to about 18 g. In some instances, the electric stimulator may comprise a mass of about 1 g to about 3 g, about 1 g to about 6 g, about 1 g to about 8 g, about 1 g to about 10 g, about 1 g to about 12 g, about 1 g to about 14 g, about 1 g to about 16 g, about 1 g to about 17 g, about 1 g to about 18 g, about 3 g to about 6 g, about 3 g to about 8 g, about 3 g to about 10 g, about 3 g to about 12 g, about 3 g to about 14 g, about 3 g to about 16 g, about 3 g to about 17 g, about 3 g to about 18 g, about 6 g to about 8 g, about 6 g to about 10 g, about 6 g to about 12 g, about 6 g to about 14 g, about 6 g to about 16 g, about 6 g to about 17 g, about 6 g to about 18 g, about 8 g to about 10 g, about 8 g to about 12 g, about 8 g to about 14 g, about 8 g to about 16 g, about 8 g to about 17 g, about 8 g to about 18 g, about 10 g to about 12 g, about 10 g to about 14 g, about 10 g to about 16 g, about 10 g to about 17 g, about 10 g to about 18 g, about 12 g to about 14 g, about 12 g to about 16 g, about 12 g to about 17 g, about 12 g to about 18 g, about 14 g to about 16 g, about 14 g to about 17 g, about 14 g to about 18 g, about 16 g to about 17 g, about 16 g to about 18 g, or about 17 g to about 18 g. In some instances, the electric stimulator may comprise a mass of about 1 g, about 3 g, about 6 g, about 8 g, about 10 g, about 12 g, about 14 g, about 16 g, about 17 g, or about 18 g. In some instances, the electric stimulator may comprise a mass of at least about 1 g, about 3 g, about 6 g, about 8 g, about 10 g, about 12 g, about 14 g, about 16 g, or about 17 g. In some instances, the electric stimulator may comprise a mass of at most about 3 g, about 6 g, about 8 g, about 10 g, about 12 g, about 14 g, about 16 g, about 17 g, or about 18 g.

In some instances, the electric stimulator may be sterilizable with conventional methods of sterilization used in the medical field, e.g., gas sterilization, steam sterilization, UV sterilization, etc.

In some cases, the one or more stimulator electrodes may provide a constant electrical stimulation, or base stimulation 146 and 150 for an individual experiencing urge incontinence. In some cases, constant electrical stimulation may comprise constant frequency, amplitude, current, or any combination thereof. In some instances, the stimulator electrode may provide a temporary electrical stimulation lasting the duration of a stress incontinence 148 episode for an individual experiencing stress incontinence. In some cases, the stimulator electrode may provide a constant electrical stimulation (i.e., basal stimulation pattern) with a temporary activated stimulation (i.e., activation stimulation pattern) lasting the duration of a stress incontinence episode for an individual experiencing mixed incontinence.

In some instances, the device disclosed herein may comprise a non-transitory computer readable medium that includes software. In some cases, the software may be configured to record a signal from the one or more sensor electrodes. In some cases, the software may be configured to process the recorded signal from the one or more sensor electrodes to determine whether an electrical stimulation pattern may need to be delivered to the one or more stimulator electrodes innervating the one or more pudendal nerves. In some instances, the software may be configured to adjust parameters of the sensor electrode in response to the observed signal. In some cases, the recorded signal of the sensor electrode by the software may observe a signal that saturates the sensor electrode's dynamic range. In some cases, the gain of the sensor electrode may be adjusted by the software to allow for sufficient monitoring and thresholding of the myoelectric EMG signals of the individual.

Nerve Stimulation Using the Device

Figure 3:
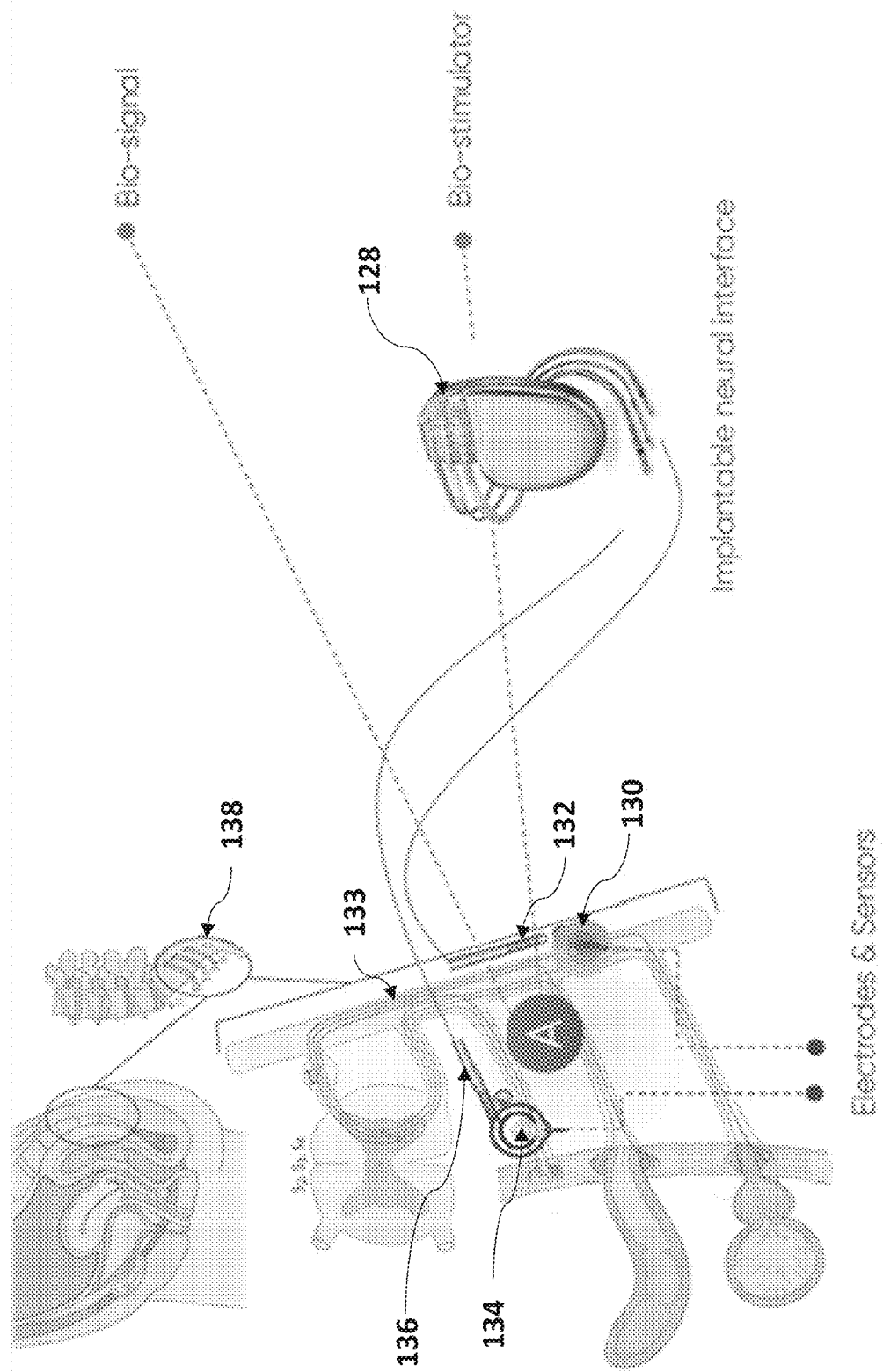
FIG. 3 shows an exemplary embodiment of the devices and methods described herein targeting the pudendal nerve by placing the sensor and stimulator electrodes near the pudendal nerve. The sensor electrode captures the bio-signal to classify any stress events, and the stimulator electrodes deliver the stress electrical stimulation ("bio-simulator"), which is adapted from the base stimulation to account for the stress event, to act on the target sphincter muscle.

FIG. 3 shows an exemplary embodiment of the devices and methods described herein implanted in an individual. In some cases, the implanted device may target the pudendal nerve 133 by placing the sensor electrodes 134 and 136 and stimulation electrodes near pudendal nerve 130 and 132. The sensor electrode 134 and 136 may capture the bio-signal to classify any stress events, and the stimulator electrodes 130 and 132 may deliver the stress electrical stimulation ("biosimulator"), which is adapted from the base stimulation to account for the stress event, to act on the target sphincter muscle.

In some cases, providing electrical stimulation to the pudendal nerve instead of the sacral nerve may provide a greater precision as the pudendal nerve or branches thereof is lower than the sacral nerve and closer to the organs and tissues involved in incontinence than the sacral nerves. The sensor electrodes of the device capture the bio-signal to classify any stress events, and the stimulator electrodes of the device deliver the stress electrical stimulation ("biosimulator"), which is adapted from the base stimulation to account for the stress event, to act on the target sphincter muscle.

System for Nerve Stimulation for Managing Incontinence

Figure 5:
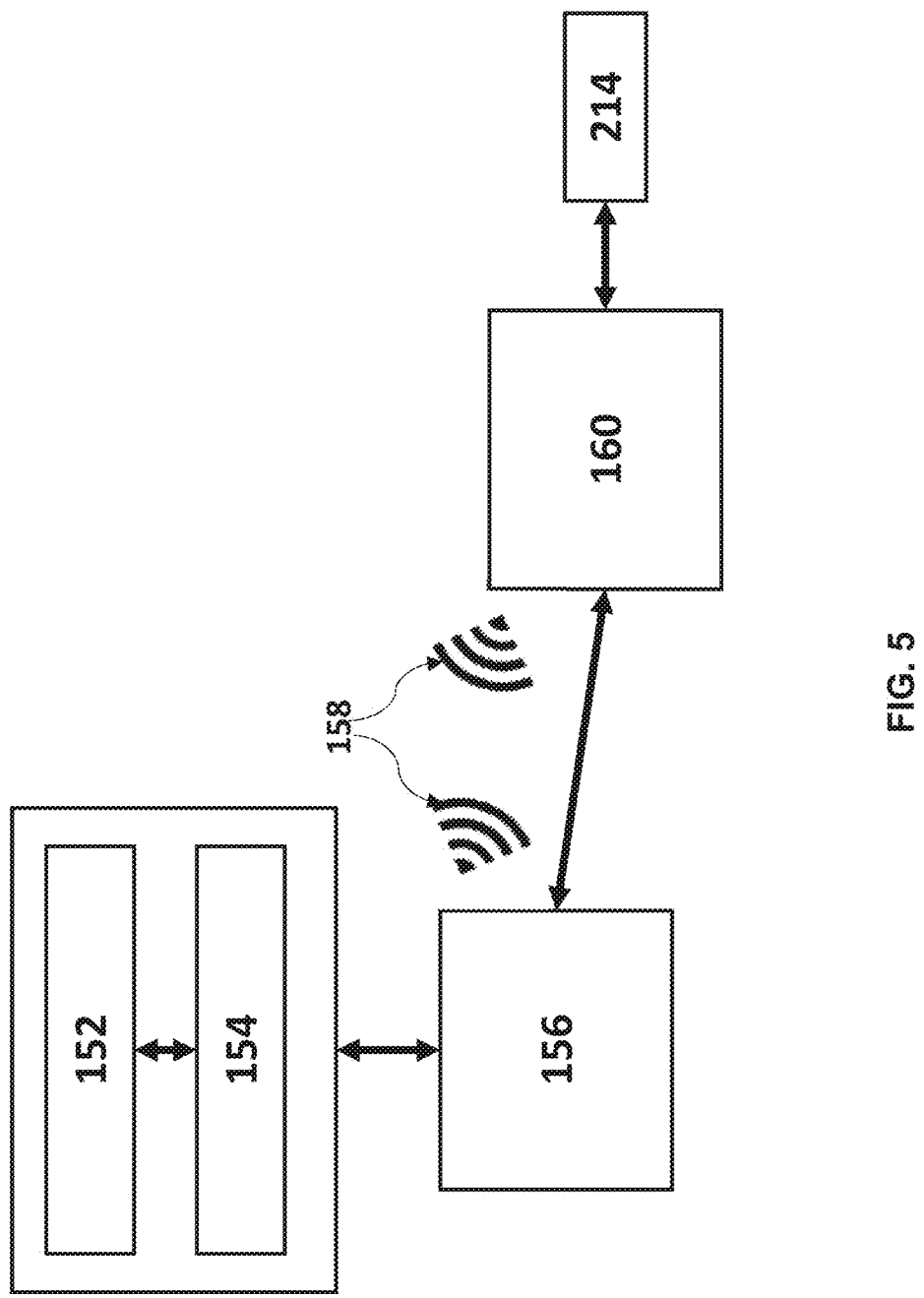
FIG. 5 shows an exemplary embodiment of a system block diagram for the devices and methods described herein configured to implement slow- and fast-adapting algorithms. API is an application programming interface; MICS is the Medical Information and Communication band.

FIG. 5 shows an exemplary embodiment of a system block diagram for the devices and methods described herein with the slow- and fast-adapting algorithms. In some cases, the systems disclosed herein may comprise a plurality of sub-modules. In some instances, the sub-modules may comprise: an offline analysis module 152, a clinician control module 154, a patient controller module 156, an implantable module 160, or any combination thereof.

In some cases, the offline analysis module 152 may comprise a data repository, an analysis software a visualization software, or any combination thereof. In some instances, the offline analysis module may be used to retrospectively analyze and graphically visualize an individual's implant performance to prevent episodes of incontinence. The off-line analysis module 152 may be programmatically coupled to the clinician control module through an application programming interface (API). In some instances, the clinician control module may comprise software that may tune or change the electrical stimulation patterns of the individual's electrical stimulation implant.

In some cases, the clinical control module 154 may comprise stimulation management and device monitor software, stimulation programming map, classification configuration dashboard, streaming data collection dashboard, or any combination thereof. In some cases, a health care personnel may assist an individual with an electrical implant by updating or modifying their electrical implant parameters through the clinical control module 154. In some cases, the clinical control module may be utilized to initialize an individual's electrical implant after implantation through an USB interface to the patient controller module 156.

In some cases, the patient controller module 156 may comprise a direct interface to control aspects of their electrical stimulator as described herein. In some instances, the patient controller module 156 may comprise: medical information and communication band (MICS) communication platform, manual electrical stimulator control, enable or disable algorithm functionality, algorithm patient alerts, an inductive or wired charger for the implantable pulse generator rechargeable battery, or any combination thereof.

In some cases, the patient controller module 156 may be configured to wirelessly and/or inductively charge the implantable pulse generator rechargeable battery with a recharger of the patient controller module 156. In some cases, the patient controller module 156 may magnetically couple to the implantable pulse generator 160 from outside the subject's skin. In some cases, the magnetic coupling of the controller module 156 to the implantable pulse generator 160 may be made such that the coupling is ergonomic for the subject such that the subject may conduct him/herself as if the controller module 156 is not magnetically coupled to the implantable pulse generator 160. In some cases, the patient controller module 156 may comprise a battery that may be recharged through wireless inductive charging via the recharger and/or wired charging. In some cases, the patient controller module 156 may comprise a rechargeable lithium-ion battery. In some instances, the recharger may comprise one or more inductive coils used when charging the patient controller module 156 and/or when using the patient controller module 156 to charge the implantable pulse generator 160. In some cases, the patient controller module, shown as shown in FIG. 7B may be configured 722 to accept additional memory storage 723. In some cases, the additional memory storage may be used to transport patient data and/or information between patient/subject and provider.

In some cases, the patient controller module 156 may directly or automatically control the implantable pulse generator 160. In some cases, the implantable pulse generator 160 may comprise a corresponding MICS-telemetry communication platform to that of the MICS communication platform of the patient controller module, enabling the communication between the two devices over an ad hoc Wi-Fi network 158. In some instances, the implantable pulse generator 160 may further comprise a three-axis accelerometer biopotential amplifier that may be electrically coupled to one or more electrodes leads 214. In some cases the one or more electrode leads may comprise one or more stimulator and/or sensor electrodes. In some cases, a biopotential amplifier may be electrically coupled to a computation sub module comprising a classifier, control policy, real-time clock scheduler, microprocessor, or any combination thereof. In some instances, the biopotential amplifier, classifier, control policy, real-time clock scheduler, and microprocessor, or any combination thereof, may process and interpret detected myoelectric EMG signals in the patient to determine the necessary electrical stimulation pattern provided by the actuator to the one or more stimulator electrodes to prevent an episode of incontinence in an individual.

Figure 7A:
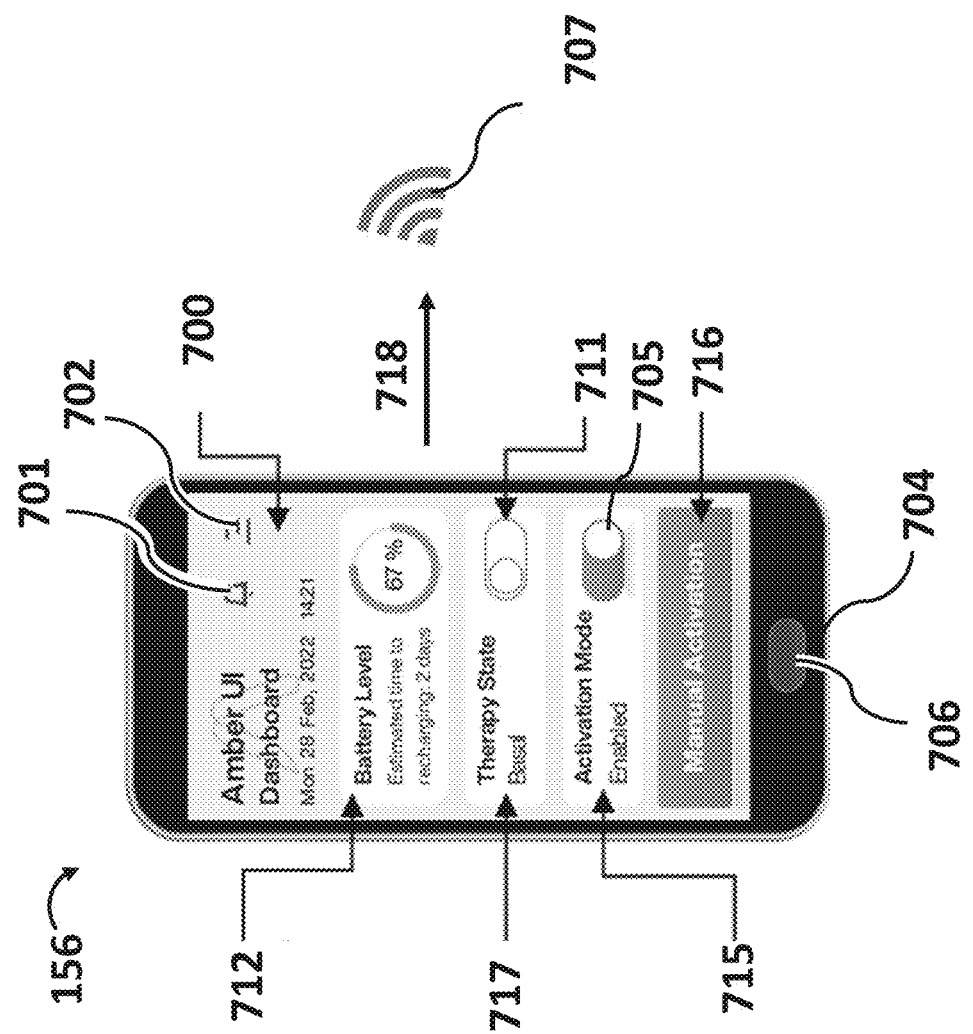
FIGS. 7A-7B show an example embodiment of the patient controller module, as described in some embodiments herein.
Figure 7B:
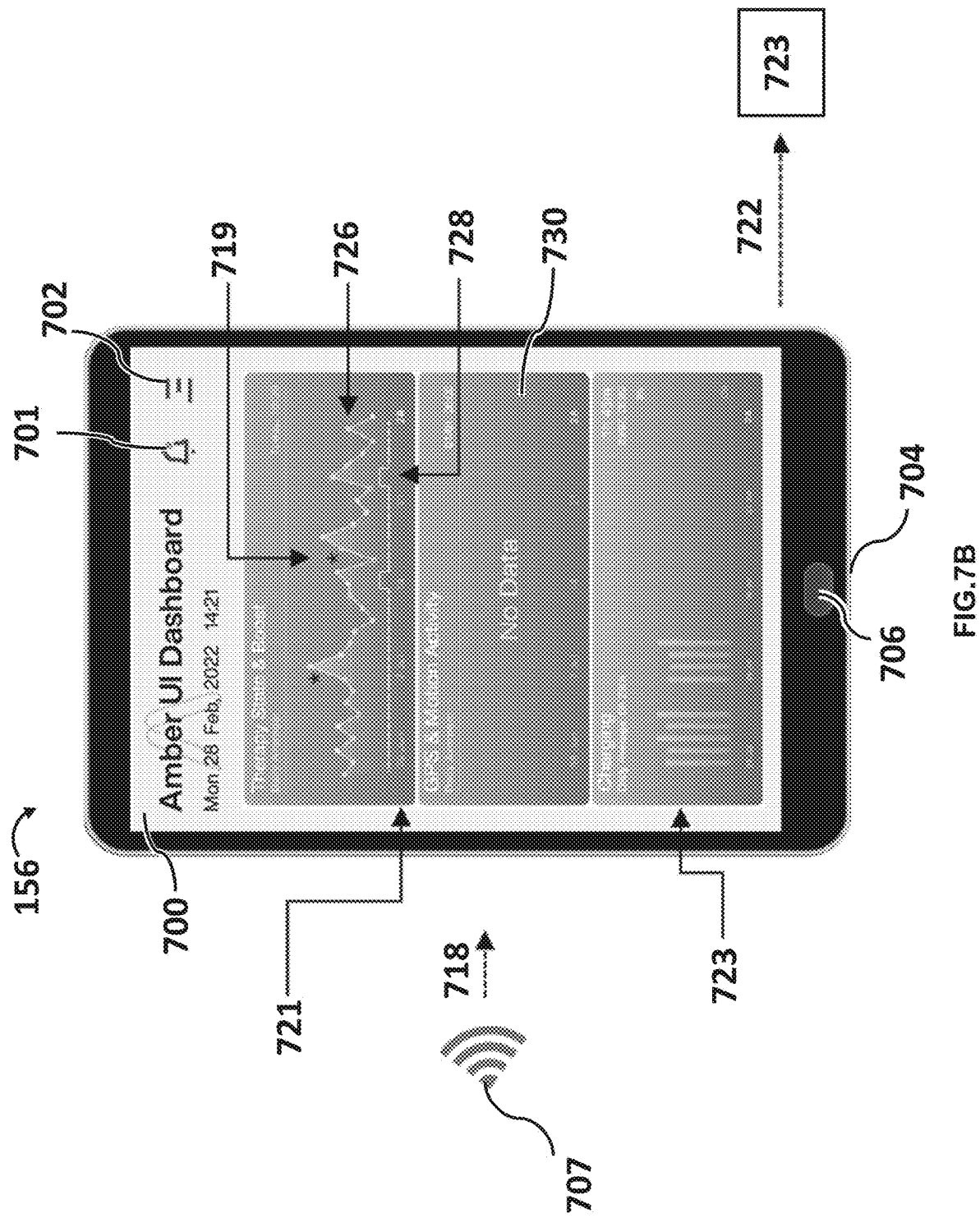

In some instances, the patient controller module 156 may comprise a user interface, ports, indicators, or any combination thereof as seen in FIGS. 7A-7B. The user interface and/or ports of the patient controller module may comprise an input charging socket 704, keypad navigation button 706, stimulation indicator, communication indicator, output charging adapter port, battery level indicator in both percentage and number of days 712, manual excitation override button 716, or any combination thereof. In some cases, the input charging socket may be configured to accept a USB A, B, and/or C, Firewire, any micro versions thereof, or any combinations thereof. connections. In some instances, the patient controller module 156 may be connected to a power converter to through a corresponding cable adapted to the input charging socket to charge the patient controller module 156.

User Interface

The patient controller module 156 may comprise a user interface 700 where the user interface may comprise one or more user interface objects (701, 702, 705, 711, 712, 715, 716, 717, 721, 730, 723), and/or views as seen in FIG. 7A-7B. In some cases, the user interface 700 may comprise a touch screen display configured to receive touch or pressing input from a user, patient, and/or medical care personnel. In some cases, a user, patient, and/or medical care personnel may press and/or interact with button 716 based mixed graphic and text indicators, and/or switch mixed graphic and text indicators (705, 711). In some cases, the user, patient, and/or medical care personnel may double tap a user interface object to enable an emergency state. In some instances, the emergency state may enable the implanted stimulator to provide electrical stimulation immediately in response to the double tap command. In some cases, a parameter or setting value of the user interface objects may be modified and/or changed by tilting the patient controller module. In some cases, tilting the patient controller module in a first direction may increase the parameter and/or setting value of the user interface object whereas tilting the patient controller module in a second direction opposite the first direction may decrease the parameter and/or setting value.

In some cases, the user interface between devices such as smart phones and tablets or other personal computing device may comprise a scaled version of the user interface. In some cases, the different user interface views e.g., the view shown in FIG. 7A and FIG. 7B may display varying user interface objects. In some cases, the user interface objects may comprise one or more buttons 716, switches (711,716), and/or graphical or image based representation of data (721,730, 723).

In some cases, users may customize the user interface object with a selection of one or more user interface objects (e.g., buttons, switch button to enable various device operation modes, graphical displays of device data, etc.). In some cases, the user views may be a predetermine set of views with set user interface object. In some instances, the user may customize and/or create one or more views accessible by the a menu icon 702. In some cases, the menu icon 702 may be configured to display one or more submenu options. In some instances, the one or more submenu options may comprise personal identification, account information, device registration, customer support, or any combination thereof submenus. In some cases, one submenu may comprise information of how to connect the device platform to pre-existing health care providers. In some cases, the user interface may comprise a notification object 701. The notification object may display a unique or highlighted state if a particular notification of device performance, detection of an incontinence event, or any combination thereof is to be provided to the user of the device. A user may interact with a press the notification object to view, in the form of a pop-up dialogue, the particular notification.

In some cases, the one or more user interface objects may comprise text and/or mixed text and vector objects representations of the various API function calls and/or sub-user interface views, as seen in FIGS. 7A-7B. In some cases, the user interface may comprise mixed text and vector objects that permit the subject or user to activate 705 or de-activate 711 electrical stimulation of the device 716, adjust device parameters 715, indicate therapy state 717, view device measured EMG signals 721, view stimulator electrode electrical signal characteristics (e.g., frequency, amplitude, pulse width, etc.) delivered, view a medical portal to submit user data to a health care provider, log resulting incontinent events 719 overlaid on top of measured ENG/EMG signals, or any combination thereof. In some cases, the user interface may further comprise a battery 712 and wireless communication connectivity indicator for the users and/or subjects to visualize patient controller module 156 operating properties.

In some cases, the keypad navigation button 706 may be configured to navigate between various user interface views e.g., the user interface views provided in FIG. 7A and FIG. 7B In some instances, the patient controller module 156 may comprise visual indicators (715, 717, 712), configured to indicate whether the implanted electrical stimulator is outputting electrical stimulation and/or the presence or lack thereof connectivity with a second or third device. In some cases, the patient controller module may comprise a device adjustment parameter, where the device adjustment parameter may comprise a stimulation indicator, or an activation of a stimulation mode 715. In some cases, the stimulation indicator may be in electrical communication with a processor, described elsewhere herein, configured to display a visual indicator when the stimulator is providing an electrical stimulation to a subject. In some instances, the patient controller module may comprise a connectivity indicator. In some cases, the connectivity indicator may be in electrical communication with a processor, described elsewhere herein, and configured to provide a visual indicator when the patient controller module is connected to one or more discrete devices, data servers, local WIFI or ad-hoc WIFI networks, Bluetooth, medical implant communication system (MICS), or any combination thereof. In some cases, the connectivity indicator may indicate the wireless connection with the implanted electrical stimulator. In some cases, the connectivity indicator may comprise one or more states. In some instances, a first state my comprise a solid image indicator, where such a solid image indicator may notify a user, subject, individual, and/or health care personnel, a successfully established communication pairing between the patient controller module and a third device, server, etc. A second state may comprise a flashing image indicator, where such a flashing image indicator indicates a paired communication state between the patient controller module and a third device, server, etc. In some cases, the image indicator may comprise the universal symbol for Bluetooth that may be observed on smart devices and/or devices with Bluetooth connectivity. In some cases, the image indicator may comprise a graphic of the universal symbol indicator for Wi-Fi (e.g., a quarter circle of concentric rings) seen commonly on smart devices and/or devices with Wi-Fi connectivity.

In some cases, device data (e.g., EMG/ENG, accelerometer, gyroscopic, magnetometer, 3-D spatial movement, global positioning system (GPS) data, or any combination thereof) may be transmitted 718 over Wi-Fi, Bluetooth, MICS, or other ad-hoc networks between one or more devices, as described elsewhere herein.

FIG. 7B shows a different user interface view than that of the FIG. 7A. In some cases, the user interface of FIG. 7B may comprise one or more user interface objects (721, 730, 723), where each user interface object displays device data received 718 through wireless transmission 707 as described above. In some cases, one of the user interface objects may comprise a graphical therapy object 721. The graphical therapy object may display detected EMG/ENG signals 726 and corresponding stimulation profiles 728. In some cases, the graphical therapy object may display leak events 719 of where the user indicated an incontinent event but where the device did not provide stimulation. Another user interface object may comprise a GPS and motion activity object 730. In some instances, the motion activity object 730 may display GPS and motion data of the subject over time. The GPS and motion data may be useful considerations when improving the classifier described elsewhere herein. Another user interface object may comprise a charging indicator object 723. In some cases, the charging indicator object may display charge capacitance of the implanted stimulator over a period of time. In some cases, the charging indicator object may be used to monitor the health of the battery of the implanted stimulator. A user interacting with the display view shown in FIG. 7B may pinch, swipe, or otherwise interact with the data of each user interface object (721, 730, 723) to view other temporal regions of data or to zoom in on a particular scale of a measurement. In some cases, through the menu object 702 a user and/or subject may export their medical data to one or more provides.

Method of Preventing an Incontinence Episode

Figure 6A:
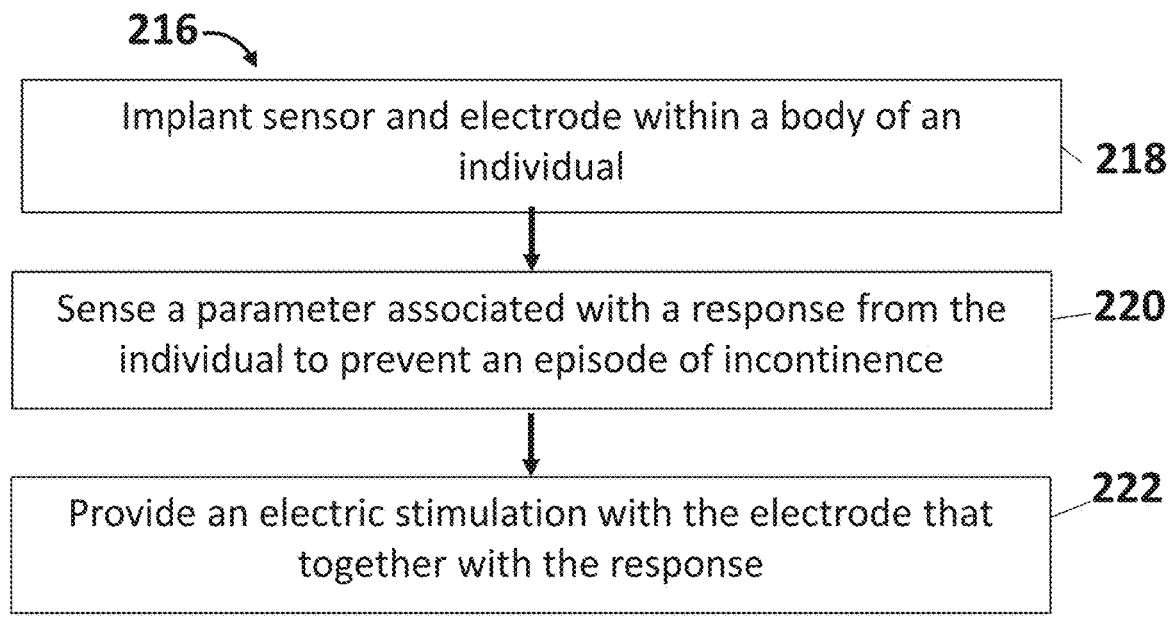
FIGS. 6A-6B show a flowchart of a method of closed-loop operation of the device of the disclosure.
Figure 6B:
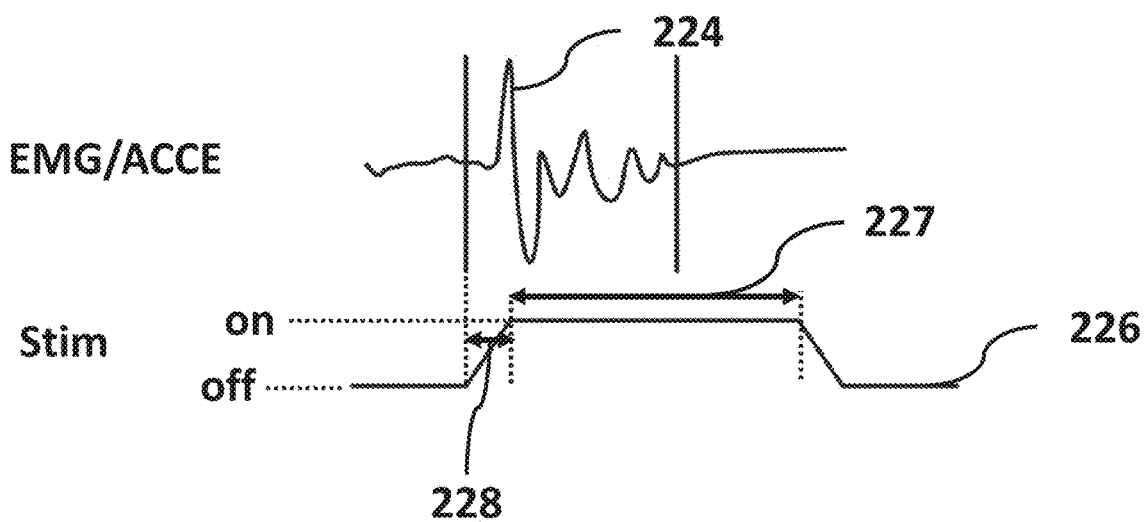

FIG. 6A illustrates a workflow of a method 216 for preventing an episode of incontinence in an individual sufferer. The method may comprise the steps of (a) implanting a sensor electrode and stimulator electrode within a body of an individual 218; (b) sensing with the sensor electrode, a parameter that is associated with a response from the individual to prevent an episode of incontinence 220; and (c) providing an electrical stimulation, with the stimulator electrode, that, together with the response, prevents the episode of incontinence 222. Often, the methods described herein prevent the episode of urinary incontinence. In some cases, the urinary incontinence may comprise at least one of urge incontinence, stress incontinence, overflow incontinence, or mixed incontinence. In some instances, the methods described herein may prevent the episode of fecal incontinence. In some cases, the method may comprise a step of providing a constant electrical stimulation at a lower intensity level than the electrical stimulation provided in step (c). The constant electrical stimulation provided at a lower intensity may assist individual's suffering from urge incontinence. In some instances, the intensity or duration of the electrical stimulation provided in step (c) may vary according to the response that is sensed in step (b). The response may vary in step (c) due to stress events such as coughing, laughing, or exercising that may require an increase in electrical stimulation to prevent an episode of incontinence. In some cases, the time period between sensing a parameter 224 and providing an electrical stimulation 226 may be described as a response time 228, as shown in FIG. 6B. In some cases, the stimulation may be provided for a duration of stimulation 227.

In some cases, the duration of stimulation 227 may comprise about 1 second to about 30 seconds. In some cases, the duration of stimulation 227 may comprise about 1 second to about 2 seconds, about 1 second to about 3 seconds, about 1 second to about 4 seconds, about 1 second to about 5 seconds, about 1 second to about 10 seconds, about 1 second to about 12 seconds, about 1 second to about 14 seconds, about 1 second to about 16 seconds, about 1 second to about 20 seconds, about 1 second to about 25 seconds, about 1 second to about 30 seconds, about 2 seconds to about 3 seconds, about 2 seconds to about 4 seconds, about 2 seconds to about 5 seconds, about 2 seconds to about 10 seconds, about 2 seconds to about 12 seconds, about 2 seconds to about 14 seconds, about 2 seconds to about 16 seconds, about 2 seconds to about 20 seconds, about 2 seconds to about 25 seconds, about 2 seconds to about 30 seconds, about 3 seconds to about 4 seconds, about 3 seconds to about 5 seconds, about 3 seconds to about 10 seconds, about 3 seconds to about 12 seconds, about 3 seconds to about 14 seconds, about 3 seconds to about 16 seconds, about 3 seconds to about 20 seconds, about 3 seconds to about 25 seconds, about 3 seconds to about 30 seconds, about 4 seconds to about 5 seconds, about 4 seconds to about 10 seconds, about 4 seconds to about 12 seconds, about 4 seconds to about 14 seconds, about 4 seconds to about 16 seconds, about 4 seconds to about 20 seconds, about 4 seconds to about 25 seconds, about 4 seconds to about 30 seconds, about 5 seconds to about 10 seconds, about 5 seconds to about 12 seconds, about 5 seconds to about 14 seconds, about 5 seconds to about 16 seconds, about 5 seconds to about 20 seconds, about 5 seconds to about 25 seconds, about 5 seconds to about 30 seconds, about 10 seconds to about 12 seconds, about 10 seconds to about 14 seconds, about 10 seconds to about 16 seconds, about 10 seconds to about 20 seconds, about 10 seconds to about 25 seconds, about 10 seconds to about 30 seconds, about 12 seconds to about 14 seconds, about 12 seconds to about 16 seconds, about 12 seconds to about 20 seconds, about 12 seconds to about 25 seconds, about 12 seconds to about 30 seconds, about 14 seconds to about 16 seconds, about 14 seconds to about 20 seconds, about 14 seconds to about 25 seconds, about 14 seconds to about 30 seconds, about 16 seconds to about 20 seconds, about 16 seconds to about 25 seconds, about 16 seconds to about 30 seconds, about 20 seconds to about 25 seconds, about 20 seconds to about 30 seconds, or about 25 seconds to about 30 seconds. In some cases, the duration of stimulation 227 may comprise about 1 second, about 2 seconds, about 3 seconds, about 4 seconds, about 5 seconds, about 10 seconds, about 12 seconds, about 14 seconds, about 16 seconds, about 20 seconds, about 25 seconds, or about 30 seconds. In some cases, the duration of stimulation 227 may comprise at least about 1 second, about 2 seconds, about 3 seconds, about 4 seconds, about 5 seconds, about 10 seconds, about 12 seconds, about 14 seconds, about 16 seconds, about 20 seconds, or about 25 seconds. In some cases, the duration of stimulation 227 may comprise at most about 2 seconds, about 3 seconds, about 4 seconds, about 5 seconds, about 10 seconds, about 12 seconds, about 14 seconds, about 16 seconds, about 20 seconds, about 25 seconds, or about 30 seconds.

In some cases the response time 228 may comprise about 60 µs to about 100 µs. In some cases the response time 228 may comprise about 60 µs to about 65 µs, about 60 µs to about 70 µs, about 60 µs to about 75 µs, about 60 µs to about 80 µs, about 60 µs to about 85 µs, about 60 µs to about 90 µs, about 60 µs to about 95 µs, about 60 µs to about 100 µs, about 65 µs to about 70 µs, about 65 µs to about 75 µs, about 65 µs to about 80 µs, about 65 µs to about 85 µs, about 65 µs to about 90 µs, about 65 µs to about 95 µs, about 65 µs to about 100 µs, about 70 µs to about 75 µs, about 70 µs to about 80 µs, about 70 µs to about 85 µs, about 70 µs to about 90 µs, about 70 µs to about 95 µs, about 70 µs to about 100 µs, about 75 µs to about 80 µs, about 75 µs to about 85 µs, about 75 µs to about 90 µs, about 75 µs to about 95 µs, about 75 µs to about 100 µs, about 80 µs to about 85 µs, about 80 µs to about 90 µs, about 80 µs to about 95 µs, about 80 µs to about 100 µs, about 85 µs to about 90 µs, about 85 µs to about 95 µs, about 85 µs to about 100 µs, about 90 µs to about 95 µs, about 90 µs to about 100 µs, or about 95 µs to about 100 µs. In some cases the response time 228 may comprise about 60 µs, about 65 µs, about 70 µs, about 75 µs, about 80 µs, about 85 µs, about 90 µs, about 95 µs, or about 100 µs. In some cases the response time 228 may comprise at least about 60 µs, about 65 µs, about 70 µs, about 75 µs, about 80 µs, about 85 µs, about 90 µs, or about 95 µs. In some cases the response time 228 may comprise at most about 65 µs, about 70 µs, about 75 µs, about 80 µs, about 85 µs, about 90 µs, about 95 µs, or about 100 µs. Through the development of iteratively trained machine learning classifiers the response time may be minimized, and improved incontinence prevention may be realized.

Figure 12A:
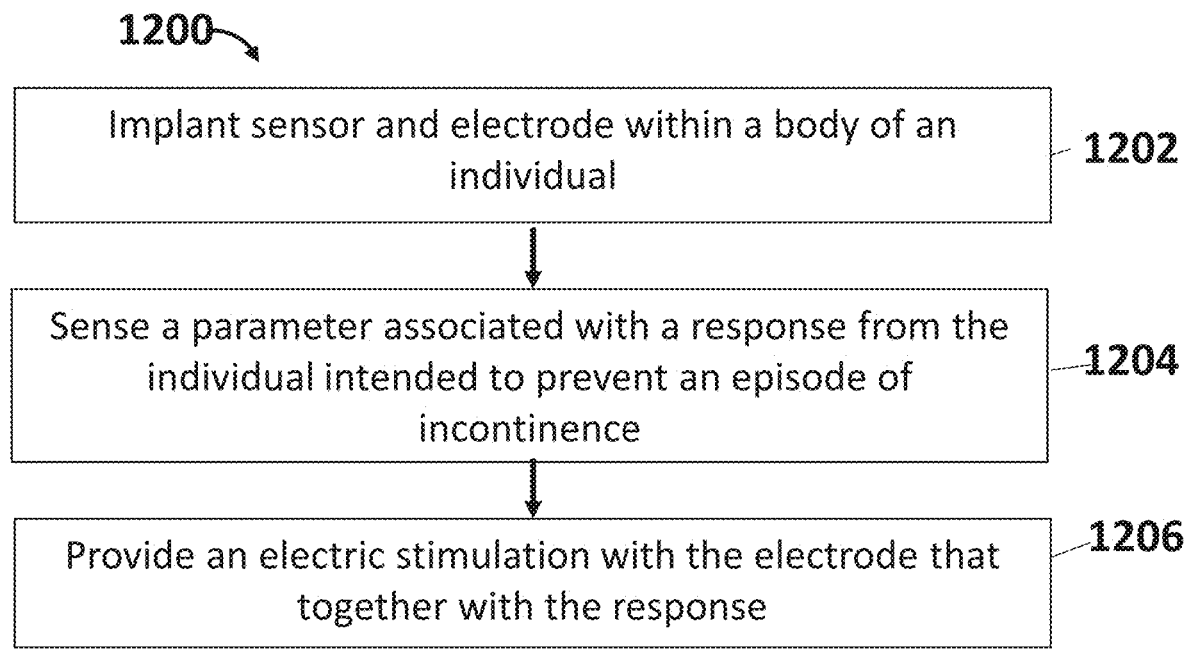
FIGS. 12A-12B show flow diagrams for detecting a purposeful or intent based contraction by the patient and providing electrical stimulation to prevent an incontinent event, as described in some embodiments herein.
Figure 12B:
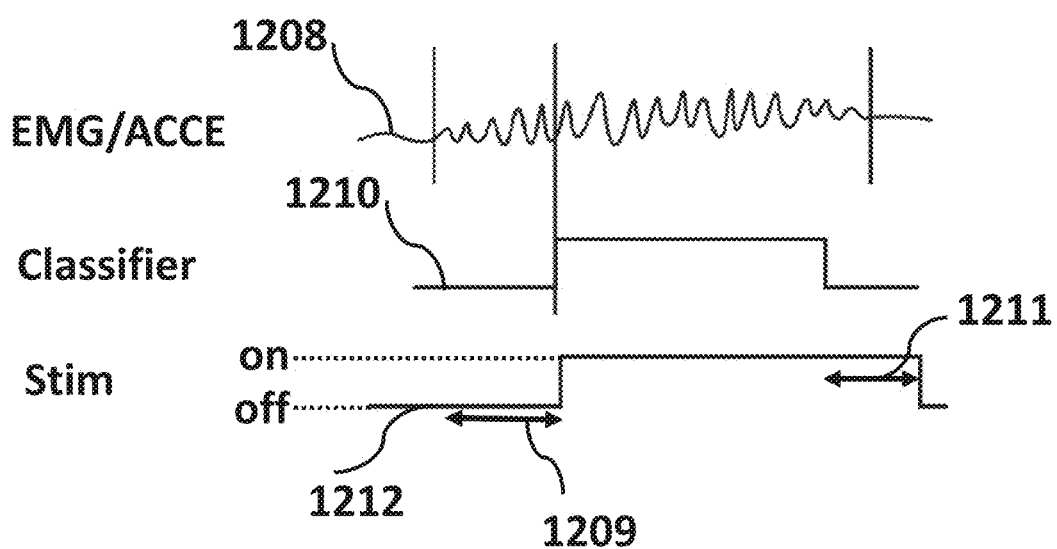

FIGS. 12A-12B illustrate a workflow of a method 1200 for preventing an episode of incontinence in an individual sufferer. The method may comprise the steps of (a) implanting a sensor electrode and stimulator electrode within a body of an individual 1202; (b) sensing a parameter associated with a response from the individual, where the response is user induced stimulus 1204; and (c) providing an electric stimulation with the stimulator electrode to prevent the incontinence event 1206. In some cases, the user induced stimulus may be intended to prevent an episode of incontinence. As shown graphically in FIG. 12B, a detected EMG signal 1208 may be analyzed by a classifier 1210, described elsewhere herein, to determine when the EMG, ENG, accelerometer, gyroscope, magnetometer, pressure sensor signals or any combination thereof signals have crossed a predetermined threshold, described elsewhere herein. Once the classifier 1210 has determined that the signal 1208 does represent an incontinent event, the processor, described elsewhere herein, may enable stimulation 1212 to prevent the incontinent event from occurring. In some cases, stimulation 1212 may comprise an extension of stimulation 1211 that may extend beyond the time the classifier 1210 determines there to be an incontinent event. In some cases the extension of stimulation 1211 may comprise a duration of time equal to the duration the subject continues to purposefully or with intent produce a muscle contraction.

In some cases the extension of stimulation 1211 may comprise about 1 s to about 30 s. In some cases the extension of stimulation 1211 may comprise about 1 s to about 3 s, about 1 s to about 5 s, about 1 s to about 8 s, about 1 s to about 10 s, about 1 s to about 12 s, about 1 s to about 15 s, about 1 s to about 18 s, about 1 s to about 20 s, about 1 s to about 22 s, about 1 s to about 24 s, about 1 s to about 30 s, about 3 s to about 5 s, about 3 s to about 8 s, about 3 s to about 10 s, about 3 s to about 12 s, about 3 s to about 15 s, about 3 s to about 18 s, about 3 s to about 20 s, about 3 s to about 22 s, about 3 s to about 24 s, about 3 s to about 30 s, about 5 s to about 8 s, about 5 s to about 10 s, about 5 s to about 12 s, about 5 s to about 15 s, about 5 s to about 18 s, about 5 s to about 20 s, about 5 s to about 22 s, about 5 s to about 24 s, about 5 s to about 30 s, about 8 s to about 10 s, about 8 s to about 12 s, about 8 s to about 15 s, about 8 s to about 18 s, about 8 s to about 20 s, about 8 s to about 22 s, about 8 s to about 24 s, about 8 s to about 30 s, about 10 s to about 12 s, about 10 s to about 15 s, about 10 s to about 18 s, about 10 s to about 20 s, about 10 s to about 22 s, about 10 s to about 24 s, about 10 s to about 30 s, about 12 s to about 15 s, about 12 s to about 18 s, about 12 s to about 20 s, about 12 s to about 22 s, about 12 s to about 24 s, about 12 s to about 30 s, about 15 s to about 18 s, about 15 s to about 20 s, about 15 s to about 22 s, about 15 s to about 24 s, about 15 s to about 30 s, about 18 s to about 20 s, about 18 s to about 22 s, about 18 s to about 24 s, about 18 s to about 30 s, about 20 s to about 22 s, about 20 s to about 24 s, about 20 s to about 30 s, about 22 s to about 24 s, about 22 s to about 30 s, or about 24 s to about 30 s. In some cases the extension of stimulation 1211 may comprise about 1 s, about 3 s, about 5 s, about 8 s, about 10 s, about 12 s, about 15 s, about 18 s, about 20 s, about 22 s, about 24 s, or about 30 s. In some cases the extension of stimulation 1211 may comprise at least about 1 s, about 3 s, about 5 s, about 8 s, about 10 s, about 12 s, about 15 s, about 18 s, about 20 s, about 22 s, or about 24 s. In some cases the extension of stimulation 1211 may comprise at most about 3 s, about 5 s, about 8 s, about 10 s, about 12 s, about 15 s, about 18 s, about 20 s, about 22 s, about 24 s, or about 30 s.

In some instances, there may be a delay 1209 between the onset of the incontinent event in the raw EMG, ENG, accelerometer, gyroscope, magnetometer, pressure sensor, or any combination thereof signal data, and the onset of the electrical stimulation. Upon training the classifier 1210 on sufficiently large and varied datasets, such delay may be minimized further improving the device performance in prevent incontinent events. In some cases, sensing may comprise determining a global positioning system (GPS) location of the individual that in combination with the parameter associated with the response from the individual is used to prevent the episode of incontinence.

Aspects of the disclosure provided herein may comprise a method of data processing. In some cases, the method of data processing may comprise: (i) receiving a measurement of a parameter previously measured by a sensor electrode, which parameter is predictive of an episode of incontinence in an individual; (ii) analyzing the parameter; and (iii) synthesizing an electrical stimulation signal for the individual, such that when the electrical stimulation signal is provided by a stimulator electrode to the individual, the electrical stimulation signal, together with an effort from the individual that is intended to prevent an episode of incontinence, prevents the episode of incontinence. In some cases, the parameter may be associated with a response from the individual intended to prevent an episode of incontinence. In some instances, the parameter may be associated with the individual's effort in trying to prevent an episode of incontinence, and where the electrical stimulation signal is synthesized so as to supplement the individual's effort with an electrical stimulation pattern that will, together with the effort from the individual, be sufficient to prevent an episode of incontinence. In some cases, the response from the individual may be insufficient on its own to prevent the episode of incontinence and the electrical stimulation signal is such that, when applied, it adds enough, together with the response, to prevent the episode of incontinence.

In some instances, the episode of incontinence may comprise urinary incontinence. In some cases, the episode of incontinence may comprise fecal incontinence. In some cases, the episode of incontinence may comprise urinary stress incontinence. In some instances, the episode of incontinence is urinary incontinence and is urge incontinence type.

In some instances, the parameter may comprise a signal from a sensor electrode that is configured to sense a contraction of a muscle of the individual related to a partial contraction of a sphincter that controls bladder or bowel voiding. In some cases, the electrical stimulation signal may comprise an electrical stimulation of the pudendal nerve. In some instances, the electrical stimulation signal may be synthesized to include a constant electrical stimulation component and a measurement parameter specific component. In some cases, an intensity or duration of the electrical stimulation that will be provided by the electrical stimulation signal may vary according to the value of the parameter that is received. In some instances, the parameter may comprise an EMG signal. In some cases, the EMG signal may determine that a contraction of at least one pelvic muscle has occurred. In some cases, a strength of the EMG signal may be proportional to the strength of the contraction of at least one pelvic muscle. In some instances, the electrical stimulation signal may comprise a first and second signals for the stimulation of a first pudendal nerve and a second pudendal nerve respectively. In some cases, the method may further comprise recording the signal previously measured by the sensor electrode. In some cases, the method may further comprise synthesizing an adjustment signal to adjust the sensor electrode in response to the recorded signal.

Assessment of Treatment of Incontinence

Ambulatory Assessments after Procedure

In some embodiments, various ambulatory assessments may be taken to determine the effectiveness of the implantation procedure. In some embodiments, the implanted IPG permits telemetric downloading of data (inputs, outputs, and event classification). In some embodiments, the participant may be in an awake ambulatory setting and a series of resting and provoked electrophysiological data may be recorded. In some embodiments, at treatment initiation (24-48 hours post-implant) sensory and motor responses may be determined from the different sensor electrodes on the implanted leads. In some embodiments, based upon the responses, the electrodes with the most adequate response may be selected to initiate treatment.

In some embodiments, the patients may be subjected to different physiological events to program the IPG. In some embodiments, these events may comprise coughing, Valsalva maneuvers, picking up a 5 kg weight, or any combination thereof. In some embodiments, pelvic floor EMG may be measured with a transvaginal and/or anal probe. In some embodiments urethral pressures may be measured. In some embodiments, 1 hour continuous 'resting' recording of inputs and outputs (downloaded by telemetry) may be taken. In some embodiments, recording during controlled participant provoked events, such as coughing, Valsalva, lifting 5 Kg weight, may be obtained. In some embodiments, recording during pelvic floor surface EMG (from transvaginal probe: women only) to correlate inputs from lead vs. surface EMG may be obtained. In some embodiments, patient tolerances of basal stimulation ramping, and actuation parameters may be obtained. In some embodiments, standard urodynamic tests are performed at 48 hours. In some embodiments, UDCs (with or without reporting of urge) may be recorded during bladder filling to assess the acute effect of patient-actuation of device. In some embodiments, a standard 1 hour pad test may be performed.

Clinical Outcomes

In some embodiments, clinical outcomes may be assessed using a 5-day voiding diary recording number of voids, number of urgency episodes, number of leaks with severity of leaks to derive: stress and urge UI (summative) episodes per unit time; stress UI episodes per unit time; urge UI episodes per unit time; urgency to void episodes per unit time; total voiding frequency per unit time; responder rate: based on >50% decrease in UI episodes per unit time; functional cure rate defined as either >90% decrease in mean total UI episodes from baseline OR mean <1 UIE per week; ICIQ-SF-UI questionnaire; or any combination thereof.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining", "measuring", "evaluating", "assessing," "assaying," and "analyzing" are often used interchangeably herein to refer to forms of measurement and include determining if an element is present or not (for example, detection). These terms can include quantitative, qualitative, or quantitative and qualitative determinations. Assessing is alternatively relative or absolute. "Detecting the presence of" includes determining the amount of something present, as well as determining whether it is present or absent.

The terms "subject," "individual," or "patient" are often used interchangeably herein. A "subject" can be a biological entity containing expressed genetic materials. The biological entity can be an animal. The subject can be a mammal. The mammal can be a human. The subject may be diagnosed or suspected of being at high risk for a disease or a condition. The disease can be incontinence. In some cases, the disease can be urinary incontinence. In some cases, the disease is bowel incontinence. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An "ex vivo" assay is not performed on a subject. Rather, it is performed upon a sample separate from a subject. An example of an "ex vivo" assay performed on a sample is an "in vitro" assay.

As used herein, the term 'about' a number refers to that number plus or minus 10% of that number. The term 'about' a range refers to that range minus 10% of its lowest value and plus 10% of its greatest value.

As used herein, the terms "treatment" or "treating" are used in reference to an intervention regimen for obtaining beneficial or desired results in the recipient. Beneficial or desired results include but are not limited to a therapeutic benefit and/or a prophylactic benefit. A therapeutic benefit may refer to prevention or amelioration of symptoms or of an underlying disorder being treated. Also, a therapeutic benefit can be achieved with prevention or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or a condition, delaying or eliminating the onset of symptoms of a disease or a condition, slowing, halting, or reversing the progression of a disease or a condition, or any combination thereof. For prophylactic benefit, a subject at risk of developing a particular disease or a condition, or to a subject reporting one or more of the physiological symptoms of a disease or a condition may undergo treatment.

The section headings used herein are for organizational purposes only and are not to be construed as limiting the subject matter described.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

NUMERATED EMBODIMENTS

Numbered embodiment 1 comprises a method for preventing an episode of incontinence in an individual in need thereof, the method comprising: (a) implanting a sensor and stimulator electrode within a body of the individual; (b) sensing, with the sensor electrode, a parameter that is associated with a response from the individual that is intended to prevent an episode of incontinence; and (c) providing an electrical stimulation, with the stimulator electrode, that, together with the response, prevents the episode of incontinence. Numbered embodiment 2 comprises the method of embodiment 1, wherein the episode of incontinence comprises urinary incontinence. Numbered embodiment 3 comprises the method of embodiment 1, wherein the episode of incontinence comprises fecal incontinence. Numbered embodiment 4 comprises the method of embodiment 1, wherein the episode of incontinence comprises urinary stress incontinence. Numbered embodiment 5 comprises the method of embodiment 1, wherein the sensor electrode is configured to sense a contraction of a muscle of the individual that results in a partial contraction of a sphincter that controls bladder or bowel voiding. Numbered embodiment 6 comprises the method of embodiment 5, wherein the sensor electrode is positioned within the pelvis of the individual. Numbered embodiment 7 comprises the method of embodiment 1, wherein the stimulator electrode provides an electrical stimulation to the pudendal nerve. Numbered embodiment 8 comprises the method of embodiment 7, wherein the sensor and the stimulator electrode are located on a single lead. Numbered embodiment 9 comprises the method of embodiment 1, comprising a step of providing a constant electrical stimulation at a lower intensity level than the electrical stimulation provided in step (c). Numbered embodiment 10 comprises the method of embodiment 9, wherein the episode of incontinence is urinary incontinence and is urge incontinence type. Numbered embodiment 11 comprises the method of embodiment 1, wherein the intensity or duration of the electrical stimulation provided in step (c) varies according to the response that is sensed in step (b). Numbered embodiment 12 comprises the method of embodiment 11, wherein the response that is sensed in step (b) is insufficient on its own to prevent the episode of incontinence and the electrical stimulation provided in step (b) adds just enough, together with the response, to prevent the episode of incontinence. Numbered embodiment 13 comprises the method of embodiment 11, wherein the response that is sensed in step (b) is insufficient on its own to prevent the episode of incontinence, and wherein the electrical stimulation provided in step (b) together with the response, prevents the episode of incontinence. Numbered embodiment 14 comprises the method of embodiment 1, wherein the sensor electrode is configured to sense an EMG signal. Numbered embodiment 15 comprises the method of embodiment 14, wherein the EMG signal determines that a contraction of at least one pelvic muscle has occurred. Numbered embodiment 16 comprises the method of embodiment 15, wherein a strength of the EMG signal is proportional to a strength of the contraction of at least one pelvic muscle. Numbered embodiment 17 comprises the method of embodiment 1, comprising a step of implanting a first stimulator electrode and second stimulator electrode, wherein the first stimulator electrode stimulates one region on a pudendal nerve and the second stimulator electrode stimulates a different region on the pudendal nerve. Numbered embodiment 18 comprises the method of embodiment 1, wherein the individual suffers from urinary incontinence of a mixed type. Numbered embodiment 19 comprises the method of embodiment 1, wherein the sensor and the stimulator electrode are operatively coupled to a processor and a non-transitory computer readable medium that includes software. Numbered embodiment 20 comprises the method of embodiment 19, wherein the sensor electrode is calibrated by the individual using an external input device that interfaces with the software. Numbered embodiment 21 comprises the method of embodiment 19, wherein the software is configured to record a signal from the sensor electrode. Numbered embodiment 22 comprises the method of embodiment 21, wherein the software is configured to adjust the sensor electrode's response to the signal. Numbered embodiment 23 comprises the method of embodiment 19, wherein the software comprises a machine learning model, and wherein the machine learning model is configured to classify signals detected by the sensor electrode and generate signals with the stimulator electrode. Numbered embodiment 24 comprises the method of embodiment 23, wherein the machine learning model is trained on prior data acquired from the individual or a set of individuals and the corresponding incontinence prevention or lack thereof information. Numbered embodiment 25 comprises the method of embodiment 24, wherein the prior data comprises the signals detected by the sensor electrode, the generated signals generated by the stimulator electrode, or any combination thereof. Numbered embodiment 26 comprises the method of embodiment 1, wherein sensing further comprises determining a global positioning system (GPS) location of the individual that in combination with the parameter associated with the response from the individual prevents the episode of incontinence.

Numbered embodiment 27 comprises a system for preventing an episode of incontinence in an individual in need thereof, the apparatus comprising: (a) a sensor electrode configured to sense a parameter that is associated with a response from the individual that is intended to prevent the episode of incontinence; (b) a stimulator electrode configured to provide electrical stimulation; (c) a processor operably coupled to the sensor and stimulator electrode; and (d)

a non-transitory computer readable storage medium including software configured to cause the processor to: (i) receive the parameter that is associated with the response from the individual that is intended to prevent the episode of incontinence; (ii) analyze the parameter that is associated with the response from the individual that is intended to prevent the episode of incontinence; and (iii) cause the stimulator electrode to provide the electrical stimulation to the individual such that the electrical stimulation together with the response from the individual that is intended to prevent the episode of incontinence prevents the episode of incontinence. Numbered embodiment 28 comprises the system of embodiment 27, wherein the episode of incontinence comprises urinary incontinence. Numbered embodiment 29 comprises the system of embodiment 27, wherein the episode of incontinence comprises fecal incontinence. Numbered embodiment 30 comprises the system of embodiment 27, wherein the episode of incontinence comprises urinary stress incontinence. Numbered embodiment 31 comprises the system of embodiment 27, wherein the sensor electrode is configured to sense a contraction of a muscle of the individual that results in a partial contraction of a sphincter that controls bladder or bowel voiding. Numbered embodiment 32 comprises the system of embodiment 27, wherein the sensor electrode is positioned within the pelvis of the individual. Numbered embodiment 33 comprises the system of embodiment 27, wherein the stimulator electrode provides the electrical stimulation to the pudendal nerve of the individual. Numbered embodiment 34 comprises the system of embodiment 27, wherein the sensor and stimulator electrodes are located on a single lead. Numbered embodiment 35 comprises the system of embodiment 27, wherein the stimulator electrode is configured to provide a constant electrical stimulation at a lower intensity level than the electrical stimulation. Numbered embodiment 36 comprises the system of embodiment 27, wherein the episode of incontinence is urinary incontinence and is urge incontinence type. Numbered embodiment 37 comprises the system of embodiment 27, wherein an intensity or duration of the electrical stimulation varies according to the response that is sensed. Numbered embodiment 38 comprises the system of embodiment 27, wherein the response that is sensed by the sensor electrode is insufficient on its own to prevent the episode of incontinence and the electrical stimulation provided adds just enough, together with the response, to prevent the episode of incontinence. Numbered embodiment 39 comprises the system of embodiment 27, wherein the response that is sensed by the sensor electrode is insufficient on its own to prevent the episode of incontinence, and wherein the electrical stimulation provided in step (b), together with the response, prevents the episode of incontinence. Numbered embodiment 40, the system of embodiment 27, wherein the sensor electrode is configured to sense an EMG signal. Numbered embodiment 41 comprises the system of embodiment 40 wherein the EMG signal determines that a contraction of at least one pelvic muscle has occurred. Numbered embodiment 42 comprises the system of embodiment 41, wherein a strength of the EMG signal is proportional to a strength of the contraction of at least one pelvic muscle. Numbered embodiment 43 comprises the system of embodiment 27, wherein the stimulator electrode comprises a first stimulator electrode and a second stimulator electrode, wherein the first stimulator electrode stimulates a first pudendal nerve and the second stimulator electrode stimulates a second pudendal nerve. Numbered embodiment 44 comprises the system of embodiment 27, wherein the individual suffers from urinary incontinence of a mixed type. Numbered embodiment 45 comprises the system of embodiment 27, wherein the sensor electrode is calibrated by the individual using an external input device that interfaces with the software. Numbered embodiment 46 comprises the system of embodiment 27, wherein the software is configured to further cause the processor to record a signal from the sensor electrode. Numbered embodiment 47 comprises the system of embodiment 46, wherein the software is configured to adjust the sensor electrode's response to the signal. Numbered embodiment 48 comprises the system of embodiment 27, wherein the software comprises a machine learning model, and wherein the machine learning model is configured to classify signals detected by the sensor electrode and generate signals with the stimulator electrode. Numbered embodiment 49 comprises the system of embodiment 48, wherein the machine learning model is trained on prior data acquired from the individual or a set of individuals and the corresponding incontinence prevention or lack thereof information. Numbered embodiment 50 comprises the system of embodiment 49, wherein the prior data comprises the signals detected by the sensor electrode, the generated signals generated by the stimulator electrode, or any combination thereof. Numbered embodiment 51 comprises the system of embodiment 27, wherein the software comprises analyzing a global positioning system (GPS) location of the individual that in combination with the parameter associated with the response from the individual prevents the episode of incontinence.

Numbered embodiment 52 comprises a non-transitory computer readable storage medium including software for preventing an episode of incontinence in an individual in need thereof, configured to cause a processor to: (i) receive a parameter by a sensor electrode that is associated with a response from the individual intended to prevent the episode of incontinence; (ii) analyze the parameter that is associated with the response from the individual that is intended to prevent the episode of incontinence; and (iii) cause a stimulator electrode to provide an electrical stimulation to the individual so that the electrical stimulation together with the response from the individual that is intended to prevent the episode of incontinence prevents the episode of incontinence. Numbered embodiment 53 comprises the non-transitory computer readable storage medium including software of embodiment 52, wherein the episode of incontinence comprises urinary incontinence. Numbered embodiment 54 comprises the non-transitory computer readable storage medium including software of embodiment 52, wherein the episode of incontinence comprises fecal incontinence. Numbered embodiment 55 comprises the non-transitory computer readable storage medium including software of embodiment 52, wherein the episode of incontinence comprises urinary stress incontinence. Numbered embodiment 56 comprises the non-transitory computer readable storage medium including software of embodiment 52, wherein the sensor electrode is configured to sense a contraction of a muscle of the individual that results in a partial contraction of a sphincter that controls bladder or bowel voiding. Numbered embodiment 57 comprises the non-transitory computer readable storage medium including software of embodiment 52, wherein the sensor electrode is positioned within the pelvis of the individual. Numbered embodiment 58 comprises the non-transitory computer readable storage medium including software of embodiment 52, wherein the stimulator electrode provides the electrical stimulation to the individual's pudendal nerve. Numbered embodiment 59 comprises the non-transitory computer readable storage medium including software of embodiment 52, wherein the sensor and stimulator electrodes are located on a single lead. Numbered embodiment 60 comprises the non-transitory computer readable storage medium including software of embodiment 52, wherein the stimulator electrode is configured to provide a constant electrical stimulation at a lower intensity level than the electrical stimulation. Numbered embodiment 61 comprises the non-transitory computer readable storage medium including software of embodiment 52, wherein the episode of incontinence is urinary incontinence and is urge incontinence type. Numbered embodiment 62 comprises the non-transitory computer readable storage medium including software of embodiment 52, wherein an intensity or duration of the electrical stimulation varies according to the response that is sensed. Numbered embodiment 63 comprises the non-transitory computer readable storage medium including software of embodiment 62, wherein the response that is sensed by the sensor electrode is insufficient on its own to prevent the episode of incontinence and the electrical stimulation provided adds just enough, together with the response, to prevent the episode of incontinence. Numbered embodiment 64 comprises the non-transitory computer readable storage medium including software of embodiment 62, wherein the response that is sensed by the sensor is insufficient on its own to prevent the episode of incontinence and the electrical stimulation provided together with the response, prevents the episode of incontinence. Numbered embodiment 65 comprises the non-transitory computer readable storage medium including software of embodiment 52, wherein the sensor electrode is configured to sense an EMG signal. Numbered embodiment 66 comprises the non-transitory computer readable storage medium including software of embodiment 65, wherein the EMG signal determines that a contraction of at least one pelvic muscle has occurred. Numbered embodiment 67 comprises the non-transitory computer readable storage medium including software of embodiment 66, wherein a strength of the EMG signal is proportional to a strength of the contraction of at least one pelvic muscle. Numbered embodiment 68 comprises the non-transitory computer readable storage medium including software of embodiment 52, wherein the stimulator electrode comprises a first stimulator electrode and a second stimulator electrode, wherein the first stimulator electrode stimulates a first pudendal nerve and the second stimulator electrode stimulates a second pudendal nerve. Numbered embodiment 69 comprises the non-transitory computer readable storage medium including software of embodiment 52, wherein the individual suffers from urinary incontinence of a mixed type. Numbered embodiment 70 comprises the non-transitory computer readable storage medium including software of embodiment 52, wherein the sensor electrode is calibrated by the individual using an external input device that interfaces with the software. Numbered embodiment 71 comprises the non-transitory computer readable storage medium including software of embodiment 52, wherein the software is configured to further cause the processor to record a signal from the sensor electrode. Numbered embodiment 72 comprises the non-transitory computer readable storage medium including software of embodiment 71, wherein the software is configured to adjust the sensor electrode's response to the signal. Numbered embodiment 73 comprises the non-transitory computer readable storage medium of embodiment 52, wherein the software comprises a machine learning model, and wherein the machine learning model is configured to classify signals detected by the sensor electrode and generate signals with the stimulator electrode. Numbered embodiment 74 comprises the non-transitory computer readable storage medium of embodiment 73, wherein the machine learning model is trained on prior data acquired from the individual or a set of individuals and the corresponding incontinence prevention or lack thereof information. Numbered embodiment 75 comprises the non-transitory computer readable storage medium of embodiment 74, wherein the prior data comprise the signals detected by the sensor electrode, the generated signals, or any combination thereof. Numbered embodiment 76 comprises the non-transitory computer readable medium of embodiment 52, wherein the software comprises analyzing a global positioning system (GPS) location of the individual that in combination with the parameter associated with the response from the individual prevents the episode of incontinence.

Numbered embodiment 77 comprises a method of data processing, said method comprising: (i) receiving a measurement of a parameter previously measured by a sensor electrode, which parameter is predictive of an episode of incontinence in an individual; (ii) analyzing the parameter; and (iii) synthesizing an electrical stimulation signal for the individual, so that when the electrical stimulation signal is provided by a stimulator electrode to the individual, the electrical stimulation signal, together with an effort from the individual that is intended to prevent an episode of incontinence, prevents the episode of incontinence. Numbered embodiment 78 comprises the method of embodiment 77, wherein the parameter is associated with a response from the individual intended to prevent an episode of incontinence. Numbered embodiment 79 comprises the method of embodiment 78, wherein the parameter is associated with the individual's effort in trying to prevent an episode of incontinence, and wherein the electrical stimulation signal is synthesized so as to supplement the individual's effort with an electrical stimulation pattern that will, together with the effort from the individual, be sufficient to prevent an episode of incontinence. Numbered embodiment 80 comprises the method of embodiment 79, wherein the response from the individual is insufficient on its own to prevent the episode of incontinence and the electrical stimulation signal is such that, when applied, it adds enough, together with the response, to prevent the episode of incontinence. Numbered embodiment 81 comprises the method of any one of embodiments 77 to 80, wherein the episode of incontinence comprises urinary incontinence. Numbered embodiment 82 comprises the method of embodiments 77 or 80, wherein the episode of incontinence comprises fecal incontinence. Numbered embodiment 83 comprises the method of any one of embodiments 77 to 80, wherein the episode of incontinence comprises urinary stress incontinence. Numbered embodiment 84 comprises the method of any one of embodiments 77 to 83, wherein the parameter is a signal from a sensor electrode that is configured to sense a contraction of a muscle of the individual related to a partial contraction of a sphincter that controls bladder or bowel voiding. Numbered embodiment 85 comprises the method of any one of embodiments 77 to 84, wherein the electrical stimulation signal is for the electrical stimulation of the pudendal nerve. Numbered embodiment 86 comprises the method of any one of embodiments 77 to 85, wherein the electrical stimulation signal is synthesized to include a constant electrical stimulation component and a measurement parameter specific component. Numbered embodiment 87 comprises the method of any one of embodiments 77 to 86, wherein the episode of incontinence is urinary incontinence and is urge incontinence type. Numbered embodiment 88 comprises the method of any one of embodiments 77 to 87, wherein an intensity or duration of the electrical stimulation that will be provided by the electrical stimulation signal varies according to the value of the parameter that is received. Numbered embodiment 89 comprises the method of any one of embodiments 77 to 88, wherein the parameter is an EMG signal. Numbered embodiment 90 comprises the method of embodiment 89, wherein the EMG signal determines that a contraction of at least one pelvic muscle has occurred. Numbered embodiment 91 comprises the method of embodiment 90, wherein a strength of the EMG signal is proportional to the strength of the contraction of at least one pelvic muscle. Numbered embodiment 92 comprises the method of any one of embodiments 77 to 91, wherein the electrical stimulation signal comprises first and second signals for the stimulation of a first pudendal nerve and a second pudendal nerve respectively. Numbered embodiment 93 comprises the method of any one of embodiments 77 to 92, further comprising recording the signal previously measured by the sensor electrode. Numbered embodiment 94 comprises the method of embodiment 93, further comprising synthesizing an adjustment signal to adjust the sensor electrode in response to the recorded signal.

EXAMPLES

Example 1: EMG Measurement Reproducibility

Using the systems, methods, and devices, described herein, patient EMG signals were measured and processed as patients performed muscle contractions, coughing, and Valsalva maneuvers, as can be seen in FIGS. 11A-11E. For each patient, raw EMG data 1102 was recorded and amplified, as described elsewhere herein. Subsequently, the raw EMG data was filtered 1106, rectified, and smoothed 1104.

Figure 11A:
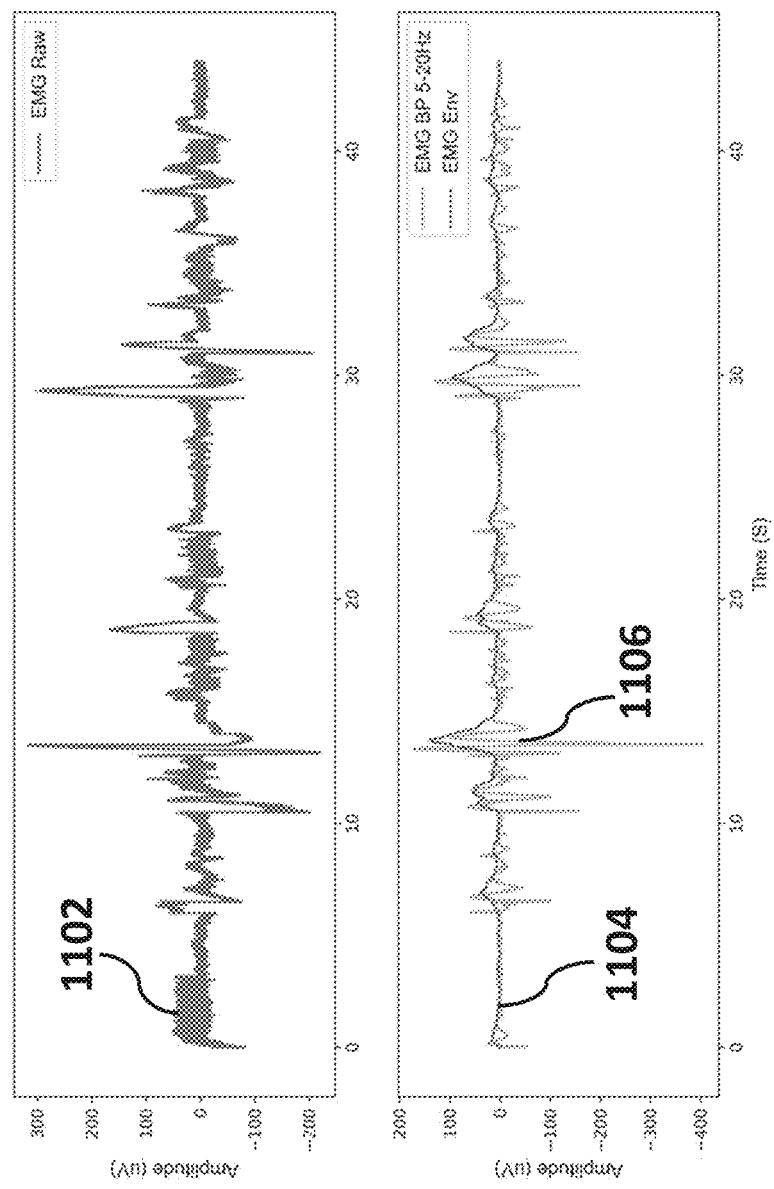
FIGS. 11A-11E show patient purposeful muscle contraction, Valsalva maneuver, and coughing EMG data acquired and processed with the methods of the disclosure, as described in some embodiments herein.
Figure 11B:
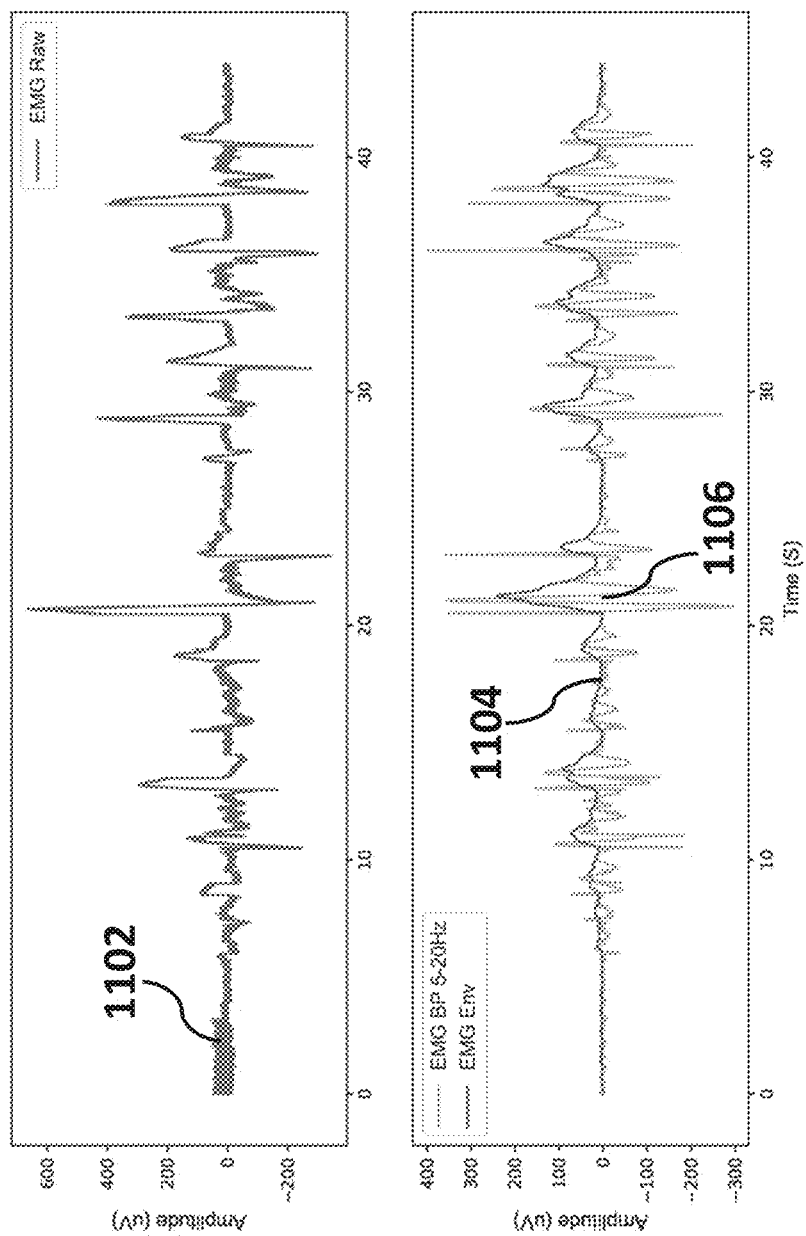
Figure 11C:
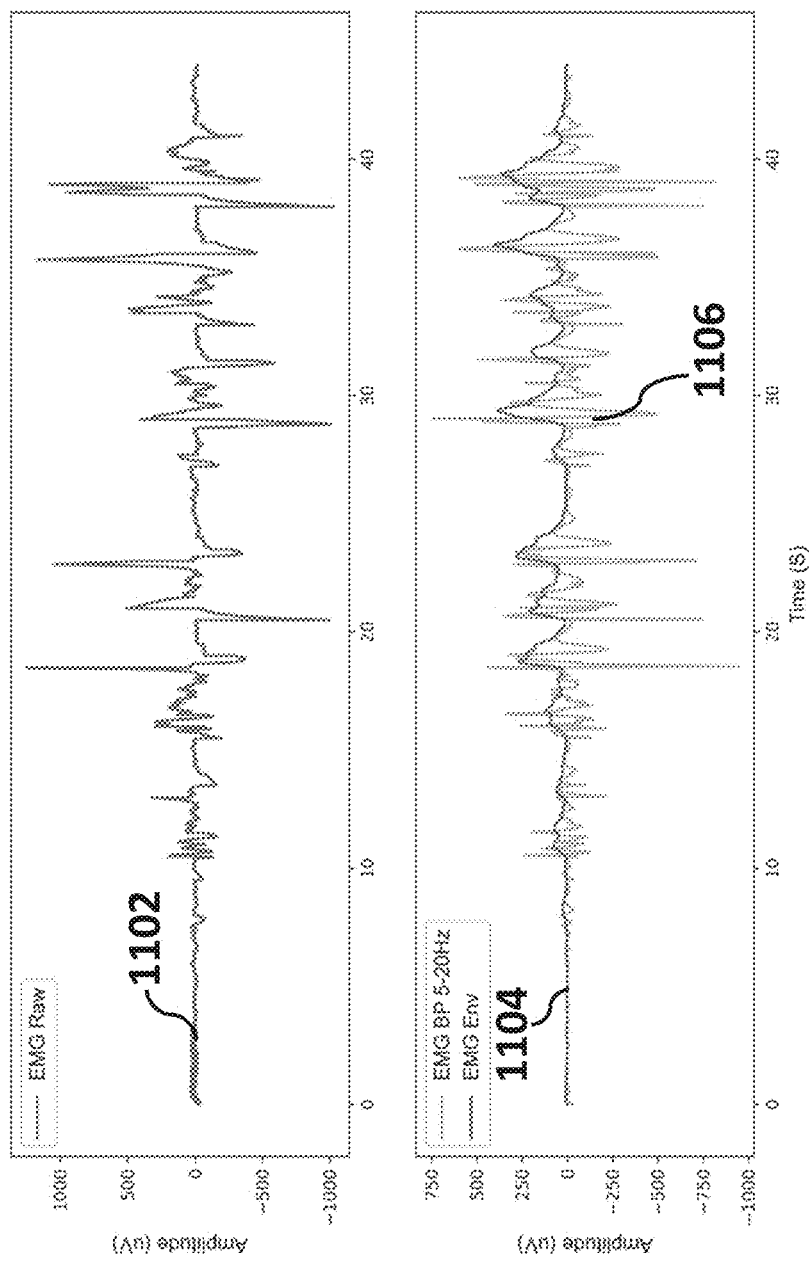
Figure 11D:
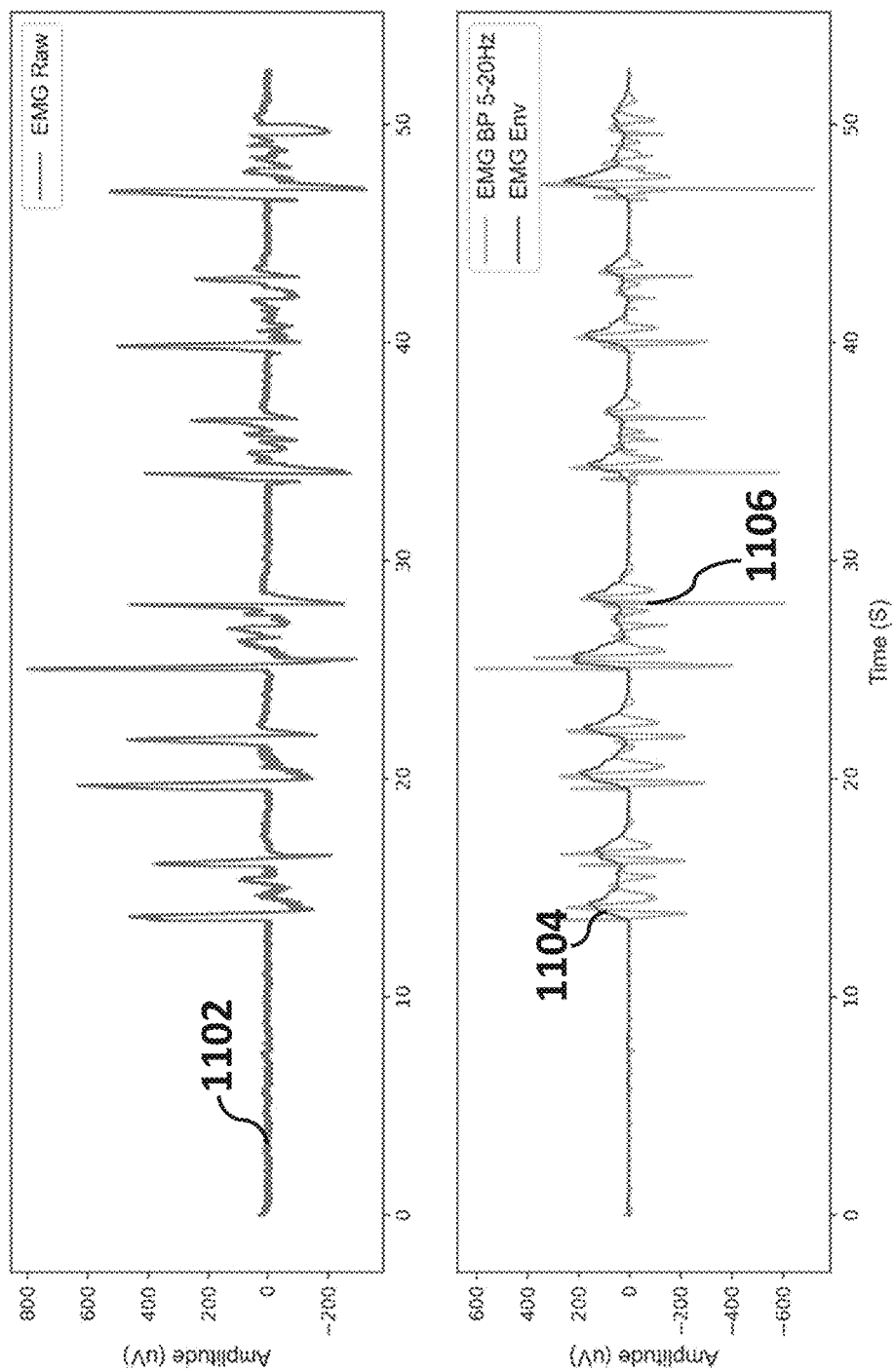
Figure 11E:
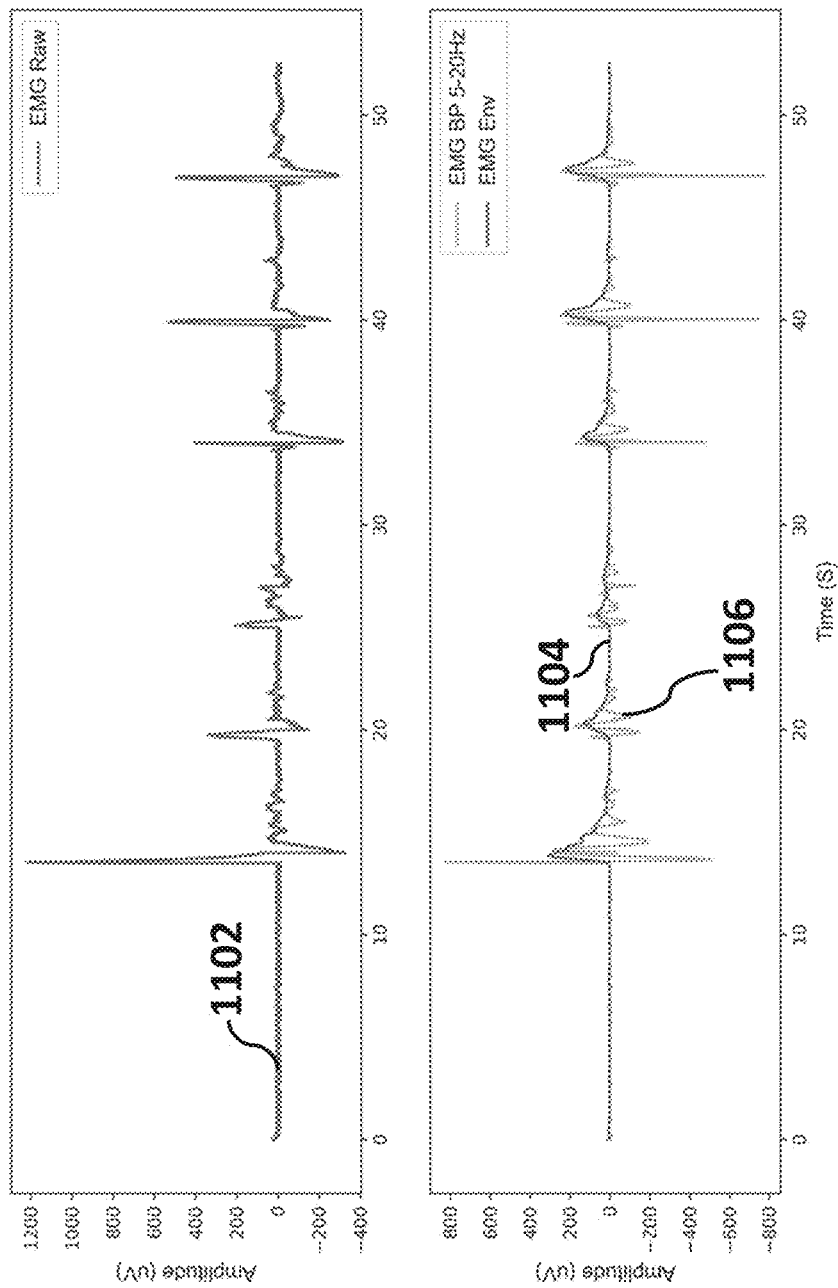

From the data shown in FIGS. 11A-11C, where a single patient iteratively performed the same sequence of muscle contractions three times, a distinct group of three signals may be observed in the temporal EMG data. Such a finding supports the reproducibility of the sensor electrodes of the devices and systems described herein and the potential ability of a trained classifier to distinguish EMG signals temporally. Similarly data for a different patient shown in FIGS. 11D-11E shows similar results as the patient in FIGS. 11A-11C.

What is claimed is:

1. A system for preventing an episode of incontinence of a patient, the system comprising:
    a first lead and a second lead configured to be implanted bilaterally proximate a pudendal nerve;
    a first sensor electrode and a second sensor electrode configured to detect a parameter indicative of the patient's effort to prevent an episode of incontinence;
    a first stimulator electrode and a second stimulator electrode configured to provide an electrical stimulation at or near the pudendal nerve;
    wherein the first lead comprises the first sensor electrode and the first stimulator electrode;
    wherein the second lead comprises the second sensor electrode and the second stimulator electrode; and
    an implantable pulse generator operably coupled to the first and second stimulator electrodes and the first and second sensor electrodes;
    wherein the implantable pulse generator is configured to provide a base stimulation level;
    wherein in response to detecting the parameter indicative of the patient's effort to prevent the episode of incontinence, the implantable pulse generator is configured to provide an activated electrical stimulation level configured to prevent the episode of incontinence;
    wherein the activated electrical stimulation level is higher than the base stimulation level; and
    wherein the implantable pulse generator is further configured to provide the activated electrical stimulation level to the same lead that detected the parameter indicative of the patient's effort to prevent the episode of incontinence.

2. The system of claim 1, wherein each of the first sensor electrode and the second sensor electrode is configured to detect an EMG signal.

3. The system of claim 2, wherein the EMG signal is indicative of a contraction of a sphincter or a pelvic muscle.

4. The system of claim 2, wherein the EMG signal is indicative of a purposeful contraction of a pelvic muscle.

5. The system of claim 1, wherein the activated electrical stimulation level is higher than the base stimulation level in one or more of frequency, amplitude, or current.

6. The system of claim 1, further comprising an external input device configured to adjust parameters of the activated electrical stimulation level.

7. The system of claim 1, wherein the activated electrical stimulation level is based at least in part on a real-time clock scheduler.

8. A system for ameliorating an episode of incontinence of a patient, the system comprising:
    a first sensor electrode configured to detect an EMG signal indicative of the patient's effort to ameliorate an episode of incontinence;
    a second sensor configured to sense a second parameter indicative of the patient's effort to prevent the episode of incontinence;
    at least one stimulator electrode configured to provide an electrical stimulation at or near a pudendal nerve; and
    an implantable pulse generator operably coupled to the at least one stimulator electrode and the first sensor electrode;
    wherein the implantable pulse generator is configured to provide a base stimulation level;
    wherein in response to detecting the EMG signal indicative of the patient's effort to prevent the episode of incontinence and the second parameter, the implantable pulse generator is configured to provide an activated electrical stimulation level configured to ameliorate the episode of incontinence;
    wherein the activated electrical stimulation level is higher than the base stimulation level.

9. The system of claim 8, wherein the EMG signal is indicative of a contraction of a sphincter or a pelvic muscle.

10. The system of claim 8, wherein the EMG signal is indicative of a purposeful contraction of a pelvic muscle.

11. The system of claim 8, wherein an intensity of the activated electrical stimulation level is higher than an intensity of the base stimulation level.

12. The system of claim 8, wherein the activated electrical stimulation level is based at least in part on a real-time clock scheduler.

13. A system for ameliorating an episode of incontinence of a patient, the system comprising:
    a first sensor electrode configured to detect an EMG signal indicative of the patient's effort to ameliorate an episode of incontinence;
    at least one stimulator electrode configured to provide an electrical stimulation at or near a pudendal nerve; and an implantable pulse generator operably coupled to the at least one stimulator electrode and the first sensor electrode;

wherein the implantable pulse generator is configured to provide a base stimulation level, wherein the base stimulation level has a constant frequency;

wherein in response to detecting the EMG signal indicative of the patient's effort to prevent the episode of incontinence, the implantable pulse generator is configured to provide an activated electrical stimulation level configured to ameliorate the episode of incontinence;

wherein the activated electrical stimulation level is higher than the base stimulation level.

14. The system of claim 13, wherein the base stimulation level further has a constant amplitude or a constant current.

15. The system of claim 13, wherein the EMG signal is indicative of a contraction of a sphincter or a pelvic muscle.

16. The system of claim 13, wherein the EMG signal is indicative of a purposeful contraction of a pelvic muscle.

17. The system of claim 13, wherein an intensity of the activated electrical stimulation level is higher than an intensity of the base stimulation level.

18. The system of claim 13, wherein in response to detecting the EMG signal indicative of the patient's effort to prevent the episode of incontinence, the activated electrical stimulation level changes: a pulse width of electrical stimulation, a frequency of electrical stimulation, or an amplitude of electrical stimulation.

19. The system of claim 13, further comprising a second sensor configured to sense a second parameter indicative of the patient's effort to prevent the episode of incontinence, wherein in response to detecting the EMG signal and the second parameter, the implantable pulse generator is configured to provide the activated electrical stimulation level configured to ameliorate the episode of incontinence.

20. The system of claim 19, the second sensor is configured to sense physical movement of the patient.

21. The system of claim 19, wherein the second sensor comprises an accelerometer or a pressure sensor.

22. The system of claim 13, wherein the activated electrical stimulation level is based at least in part on a real-time clock scheduler.

23. A system for ameliorating an episode of incontinence of a patient, the system comprising:
a first sensor electrode configured to detect an EMG signal indicative of the patient's effort to ameliorate an episode of incontinence;
at least one stimulator electrode configured to provide an electrical stimulation at or near a pudendal nerve; and
an implantable pulse generator operably coupled to the at least one stimulator electrode and the first sensor electrode;
wherein the implantable pulse generator is configured to provide a base stimulation level, wherein the base stimulation level has a constant amplitude;
wherein in response to detecting the EMG signal indicative of the patient's effort to prevent the episode of incontinence, the implantable pulse generator is configured to provide an activated electrical stimulation level configured to ameliorate the episode of incontinence;
wherein the activated electrical stimulation level is higher than the base stimulation level.

24. The system of claim 23, wherein the base stimulation level further has a constant current.

25. The system of claim 23, wherein the EMG signal is indicative of a contraction of a sphincter or a pelvic muscle.

26. The system of claim 23, wherein the EMG signal is indicative of a purposeful contraction of a pelvic muscle.

27. The system of claim 23, wherein an intensity of the activated electrical stimulation level is higher than an intensity of the base stimulation level.

28. The system of claim 23, wherein in response to detecting the EMG signal indicative of the patient's effort to prevent the episode of incontinence, the activated electrical stimulation level changes: a pulse width of electrical stimulation, a frequency of electrical stimulation, or a frequency of electrical stimulation.

29. The system of claim 23, further comprising a second sensor configured to sense a second parameter indicative of the patient's effort to prevent the episode of incontinence, wherein in response to detecting the EMG signal and the second parameter, the implantable pulse generator is configured to provide the activated electrical stimulation level configured to ameliorate the episode of incontinence.

30. The system of claim 29, the second sensor is configured to sense physical movement of the patient.

31. The system of claim 29, wherein the second sensor comprises an accelerometer or a pressure sensor.

32. The system of claim 23, wherein the activated electrical stimulation level is based at least in part on a real-time clock scheduler.

33. A system for ameliorating an episode of incontinence of a patient, the system comprising:
a first sensor electrode configured to detect an EMG signal indicative of the patient's effort to ameliorate an episode of incontinence;
at least one stimulator electrode configured to provide an electrical stimulation at or near a pudendal nerve; and
an implantable pulse generator operably coupled to the at least one stimulator electrode and the first sensor electrode;
wherein the implantable pulse generator is configured to provide a base stimulation level, wherein the base stimulation level has a constant current;
wherein in response to detecting the EMG signal indicative of the patient's effort to prevent the episode of incontinence, the implantable pulse generator is configured to provide an activated electrical stimulation level configured to ameliorate the episode of incontinence;
wherein the activated electrical stimulation level is higher than the base stimulation level.

34. The system of claim 33, wherein the EMG signal is indicative of a contraction of a sphincter or a pelvic muscle.

35. The system of claim 33, wherein the EMG signal is indicative of a purposeful contraction of a pelvic muscle.

36. The system of claim 33, wherein an intensity of the activated electrical stimulation level is higher than an intensity of the base stimulation level.

37. The system of claim 33, wherein in response to detecting the EMG signal indicative of the patient's effort to prevent the episode of incontinence, the activated electrical stimulation level changes: a pulse width of electrical stimulation, a frequency of electrical stimulation, or an amplitude of electrical stimulation.

38. The system of claim 33, further comprising a second sensor configured to sense a second parameter indicative of the patient's effort to prevent the episode of incontinence, wherein in response to detecting the EMG signal and the second parameter, the implantable pulse generator is configured to provide the activated electrical stimulation level configured to ameliorate the episode of incontinence.

39. The system of claim 38, the second sensor is configured to sense physical movement of the patient.

40. The system of claim 38, wherein the second sensor comprises an accelerometer or a pressure sensor.

41. The system of claim 33, wherein the activated electrical stimulation level is based at least in part on a real-time clock scheduler.

42. A system for ameliorating an episode of incontinence of a patient, the system comprising:
 a first sensor electrode configured to detect an EMG signal indicative of the patient's effort to ameliorate an episode of incontinence;
 at least one stimulator electrode configured to provide an electrical stimulation at or near a pudendal nerve; and
 an implantable pulse generator operably coupled to the at least one stimulator electrode and the first sensor electrode;
 wherein the implantable pulse generator is configured to provide a base stimulation level;
 wherein in response to detecting the EMG signal indicative of the patient's effort to prevent the episode of incontinence, the implantable pulse generator is configured to provide an activated electrical stimulation level configured to ameliorate the episode of incontinence and the activated electrical stimulation level changes a pulse width of electrical stimulation;
 wherein the activated electrical stimulation level is higher than the base stimulation level.

43. The system of claim 42, wherein the EMG signal is indicative of a contraction of a sphincter or a pelvic muscle.

44. The system of claim 42, wherein the EMG signal is indicative of a purposeful contraction of a pelvic muscle.

45. The system of claim 42, wherein an intensity of the activated electrical stimulation level is higher than an intensity of the base stimulation level.

46. The system of claim 42, wherein in response to detecting the EMG signal indicative of the patient's effort to prevent the episode of incontinence, the activated electrical stimulation level further changes a frequency of electrical stimulation or an amplitude of electrical stimulation.

47. The system of claim 42, further comprising a second sensor configured to sense a second parameter indicative of the patient's effort to prevent the episode of incontinence, wherein in response to detecting the EMG signal and the second parameter, the implantable pulse generator is configured to provide the activated electrical stimulation level configured to ameliorate the episode of incontinence.

48. The system of claim 47, the second sensor is configured to sense physical movement of the patient.

49. The system of claim 47, wherein the second sensor comprises an accelerometer or a pressure sensor.

50. The system of claim 42, wherein the activated electrical stimulation level is based at least in part on a real-time clock scheduler.

51. A system for ameliorating an episode of incontinence of a patient, the system comprising:
 a first sensor electrode configured to detect an EMG signal indicative of the patient's effort to ameliorate an episode of incontinence;
 at least one stimulator electrode configured to provide an electrical stimulation at or near a pudendal nerve; and
 an implantable pulse generator operably coupled to the at least one stimulator electrode and the first sensor electrode;
 wherein the implantable pulse generator is configured to provide a base stimulation level;
 wherein in response to detecting the EMG signal indicative of the patient's effort to prevent the episode of incontinence, the implantable pulse generator is configured to provide an activated electrical stimulation level configured to ameliorate the episode of incontinence and the activated electrical stimulation level changes a frequency of electrical stimulation;
 wherein the activated electrical stimulation level is higher than the base stimulation level.

52. The system of claim 51, wherein the EMG signal is indicative of a contraction of a sphincter or a pelvic muscle.

53. The system of claim 51, wherein the EMG signal is indicative of a purposeful contraction of a pelvic muscle.

54. The system of claim 51, wherein an intensity of the activated electrical stimulation level is higher than an intensity of the base stimulation level.

55. The system of claim 51, wherein in response to detecting the EMG signal indicative of the patient's effort to prevent the episode of incontinence, the activated electrical stimulation level further changes an amplitude of electrical stimulation.

56. The system of claim 51, further comprising a second sensor configured to sense a second parameter indicative of the patient's effort to prevent the episode of incontinence, wherein in response to detecting the EMG signal and the second parameter, the implantable pulse generator is configured to provide the activated electrical stimulation level configured to ameliorate the episode of incontinence.

57. The system of claim 56, the second sensor is configured to sense physical movement of the patient.

58. The system of claim 56, wherein the second sensor comprises an accelerometer or a pressure sensor.

59. The system of claim 51, wherein the activated electrical stimulation level is based at least in part on a real-time clock scheduler.

60. A system for ameliorating an episode of incontinence of a patient, the system comprising:
 a first sensor electrode configured to detect an EMG signal indicative of the patient's effort to ameliorate an episode of incontinence;
 at least one stimulator electrode configured to provide an electrical stimulation at or near a pudendal nerve; and
 an implantable pulse generator operably coupled to the at least one stimulator electrode and the first sensor electrode;
 wherein the implantable pulse generator is configured to provide a base stimulation level;
 wherein in response to detecting the EMG signal indicative of the patient's effort to prevent the episode of incontinence, the implantable pulse generator is configured to provide an activated electrical stimulation level configured to ameliorate the episode of incontinence and the activated electrical stimulation level changes an amplitude of electrical stimulation;
 wherein the activated electrical stimulation level is higher than the base stimulation level.

61. The system of claim 60, wherein the EMG signal is indicative of a contraction of a sphincter or a pelvic muscle.

62. The system of claim 60, wherein the EMG signal is indicative of a purposeful contraction of a pelvic muscle.

63. The system of claim 60, wherein an intensity of the activated electrical stimulation level is higher than an intensity of the base stimulation level.

64. The system of claim 60, further comprising a second sensor configured to sense a second parameter indicative of the patient's effort to prevent the episode of incontinence, wherein in response to detecting the EMG signal and the second parameter, the implantable pulse generator is configured to provide the activated electrical stimulation level configured to ameliorate the episode of incontinence.

65. The system of claim 64, the second sensor is configured to sense physical movement of the patient.

66. The system of claim 64, wherein the second sensor comprises an accelerometer or a pressure sensor.

67. The system of claim 64, wherein the activated electrical stimulation level is based at least in part on a real-time clock scheduler.

68. A system for ameliorating an episode of incontinence of a patient, the system comprising:
- a first sensor electrode configured to detect an EMG signal indicative of the patient's effort to ameliorate an episode of incontinence;
- a second sensor configured to sense a second parameter indicative of the patient's effort to prevent the episode of incontinence, the second sensor configured to sense physical movement of the patient;
- at least one stimulator electrode configured to provide an electrical stimulation at or near a pudendal nerve; and
- an implantable pulse generator operably coupled to the at least one stimulator electrode and the first sensor electrode;
- wherein the implantable pulse generator is configured to provide a base stimulation level;
- wherein in response to detecting the EMG signal indicative of the patient's effort to prevent the episode of incontinence and the second parameter, the implantable pulse generator is configured to provide an activated electrical stimulation level configured to ameliorate the episode of incontinence;
- wherein the activated electrical stimulation level is higher than the base stimulation level.

69. The system of claim 68, wherein the base stimulation level has: a constant frequency, a constant amplitude, or a constant current.

70. The system of claim 68, wherein the EMG signal is indicative of a contraction of a sphincter or a pelvic muscle.

71. The system of claim 68, wherein the EMG signal is indicative of a purposeful contraction of a pelvic muscle.

72. The system of claim 68, wherein an intensity of the activated electrical stimulation level is higher than an intensity of the base stimulation level.

73. The system of claim 68, wherein in response to detecting the EMG signal indicative of the patient's effort to prevent the episode of incontinence, the activated electrical stimulation level changes: a pulse width of electrical stimulation, a frequency of electrical stimulation, or an amplitude of electrical stimulation.

74. The system of claim 68, wherein the second sensor comprises an accelerometer or a pressure sensor.

75. The system of claim 68, wherein the activated electrical stimulation level is based at least in part on a real-time clock scheduler.

76. A system for ameliorating an episode of incontinence of a patient, the system comprising:
- a first sensor electrode configured to detect an EMG signal indicative of the patient's effort to ameliorate an episode of incontinence;
- a second sensor configured to sense a second parameter indicative of the patient's effort to prevent the episode of incontinence, wherein the second sensor comprises an accelerometer;
- at least one stimulator electrode configured to provide an electrical stimulation at or near a pudendal nerve; and
- an implantable pulse generator operably coupled to the at least one stimulator electrode and the first sensor electrode;
- wherein the implantable pulse generator is configured to provide a base stimulation level;
- wherein in response to detecting the EMG signal indicative of the patient's effort to prevent the episode of incontinence and the second parameter, the implantable pulse generator is configured to provide an activated electrical stimulation level configured to ameliorate the episode of incontinence;
- wherein the activated electrical stimulation level is higher than the base stimulation level.

77. The system of claim 76, wherein the base stimulation level has: a constant frequency, a constant amplitude, or a constant current.

78. The system of claim 76, wherein the EMG signal is indicative of a contraction of a sphincter or a pelvic muscle.

79. The system of claim 76, wherein the EMG signal is indicative of a purposeful contraction of a pelvic muscle.

80. The system of claim 76, wherein an intensity of the activated electrical stimulation level is higher than an intensity of the base stimulation level.

81. The system of claim 76, wherein in response to detecting the EMG signal indicative of the patient's effort to prevent the episode of incontinence, the activated electrical stimulation level changes: a pulse width of electrical stimulation, a frequency of electrical stimulation, or an amplitude of electrical stimulation.

82. The system of claim 76, wherein the second sensor further comprises a pressure sensor.

83. The system of claim 76, wherein the activated electrical stimulation level is based at least in part on a real-time clock scheduler.

84. A system for ameliorating an episode of incontinence of a patient, the system comprising:
- a first sensor electrode configured to detect an EMG signal indicative of the patient's effort to ameliorate an episode of incontinence;
- a second sensor configured to sense a second parameter indicative of the patient's effort to prevent the episode of incontinence, wherein the second sensor comprises a pressure sensor;
- at least one stimulator electrode configured to provide an electrical stimulation at or near a pudendal nerve; and
- an implantable pulse generator operably coupled to the at least one stimulator electrode and the first sensor electrode;
- wherein the implantable pulse generator is configured to provide a base stimulation level;
- wherein in response to detecting the EMG signal indicative of the patient's effort to prevent the episode of incontinence and the second parameter, the implantable pulse generator is configured to provide an activated electrical stimulation level configured to ameliorate the episode of incontinence;
- wherein the activated electrical stimulation level is higher than the base stimulation level.

85. The system of claim 84, wherein the base stimulation level has: a constant frequency, a constant amplitude, or a constant current.

86. The system of claim 84, wherein the EMG signal is indicative of a contraction of a sphincter or a pelvic muscle.

87. The system of claim 84, wherein the EMG signal is indicative of a purposeful contraction of a pelvic muscle.

88. The system of claim 84, wherein an intensity of the activated electrical stimulation level is higher than an intensity of the base stimulation level.

89. The system of claim 84, wherein in response to detecting the EMG signal indicative of the patient's effort to prevent the episode of incontinence, the activated electrical stimulation level changes: a pulse width of electrical stimulation, a frequency of electrical stimulation, or an amplitude of electrical stimulation.

90. The system of claim 84, wherein the activated electrical stimulation level is based at least in part on a real-time clock scheduler.

\* \* \* \* \*